United States Patent
Villoslada et al.

(10) Patent No.: US 9,453,047 B2
(45) Date of Patent: Sep. 27, 2016

(54) AGONISTS OF NEUROTROPHIN RECEPTORS AND THEIR USE AS MEDICAMENTS

(71) Applicant: Bionure Farma, S.L., Barcelona (ES)

(72) Inventors: Pablo Villoslada, Barcelona (ES); Angel Messeguer, Barcelona (ES)

(73) Assignees: BIONURE FARMA, S.L., Barcelona (ES); INSTITUT D'INVESTIGACIONS BIOMEDIQUES AUGUST PII SUNYER (IDIBAPS) (undivided 30% interest), Barcelona (ES); CONSEJO SUPERIOR DE INVESTIGACIONES CIENTIFICAS (CSIC) (individed 20% interest), Madrid (ES)

( * ) Notice: Subject to any disclaimer, the term of this patent is extended or adjusted under 35 U.S.C. 154(b) by 0 days.

(21) Appl. No.: 14/301,981

(22) Filed: Jun. 11, 2014

(65) Prior Publication Data
US 2015/0005239 A1 Jan. 1, 2015

Related U.S. Application Data

(62) Division of application No. 13/223,166, filed on Aug. 31, 2011, now Pat. No. 8,791,076.

(60) Provisional application No. 61/378,823, filed on Aug. 31, 2010.

(51) Int. Cl.
C07K 5/083 (2006.01)
A61K 38/06 (2006.01)
(Continued)

(52) U.S. Cl.
CPC .............. *C07K 5/0806* (2013.01); *A61K 38/06* (2013.01); *C07D 207/04* (2013.01); *C07D 207/27* (2013.01); *C07K 5/0821* (2013.01); *C07K 5/0827* (2013.01)

(58) Field of Classification Search
None
See application file for complete search history.

(56) References Cited

U.S. PATENT DOCUMENTS

| 4,731,376 A | 3/1988 | Hideg et al. |
| 6,124,361 A | 9/2000 | Chenard |

(Continued)

FOREIGN PATENT DOCUMENTS

| CA | 2427072 A1 | 4/2003 |
| EP | 1 338 604 A1 | 8/2003 |

(Continued)

OTHER PUBLICATIONS

Farmer 2015 "Hematopoietic cytokines as therapeutic players in early stages Parkinson's disease" fronteirs aging neurosci 7(126): 1-5.*

(Continued)

*Primary Examiner* — Kimberly A. Ballard
*Assistant Examiner* — Adam M Weidner
(74) *Attorney, Agent, or Firm* — Sterne, Kessler, Goldstein & Fox P.L.L.C.

(57) ABSTRACT

The invention relates to compounds of Formula I:

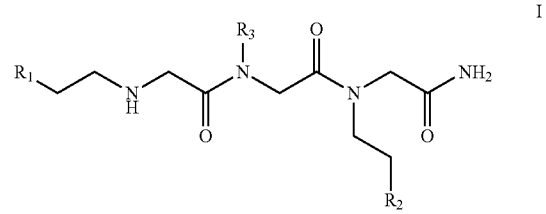

and pharmaceutically acceptable salts and prodrugs thereof, wherein $R_1$, $R_2$, and $R_3$ are defined as set forth in the specification. The compounds are agonists of neurotrophin (such as nerve growth factor) receptors.

17 Claims, 20 Drawing Sheets
(1 of 20 Drawing Sheet(s) Filed in Color)

(51) Int. Cl.

| | |
|---|---|
| C07D 207/04 | (2006.01) |
| C07K 5/097 | (2006.01) |
| C07D 207/27 | (2006.01) |
| C07K 5/08 | (2006.01) |

(56) References Cited

U.S. PATENT DOCUMENTS

| | | | |
|---|---|---|---|
| 6,271,205 | B1 | 8/2001 | Ross et al. |
| 6,384,069 | B1 | 5/2002 | Feuerstein et al. |
| 6,391,871 | B1 | 5/2002 | Olney et al. |
| 6,534,492 | B2 | 3/2003 | Carlsen et al. |
| 6,992,064 | B2 | 1/2006 | Orts et al. |
| 8,791,076 | B2 | 7/2014 | Villoslada et al. |
| 2004/0029811 | A1 | 2/2004 | Orts et al. |
| 2004/0033958 | A1 | 2/2004 | Ferrer Montiel et al. |
| 2004/0219207 | A1 | 11/2004 | Rohnert et al. |
| 2005/0009847 | A1 | 1/2005 | Bertilsson et al. |
| 2011/0052603 | A1 | 3/2011 | Bouillet et al. |
| 2011/0251266 | A1 | 10/2011 | Jin et al. |
| 2012/0237552 | A1 | 9/2012 | Moreno et al. |

FOREIGN PATENT DOCUMENTS

| | | | |
|---|---|---|---|
| EP | 2 289 886 | A1 | 3/2011 |
| WO | WO 96/40747 | A1 | 12/1996 |
| WO | WO 02/28885 | A1 | 4/2002 |
| WO | WO 2008/141762 | A2 | 11/2008 |
| WO | WO 2011/024078 | A2 | 3/2011 |
| WO | WO 2011/024079 | A2 | 3/2011 |
| WO | WO 2012/028959 | A2 | 3/2012 |

OTHER PUBLICATIONS

Aloe, L. "Nerve growth factor, human skin ulcers and vascularization. Our experience," in *NGF and Related Molecules in Health and Disease*, vol. 146 (Progress in Brain Research), Chapter 32, pp. 515-522, Elsevier B.V., Netherlands (2004).
Bonizzi, G. and Karin, M., "The two NF-κB activation pathways and their role in innate and adaptive immunity," *Trends Immunol.* 25(6):280-288, Elsevier Science Ltd., England (2004).
Elliott, J.L., "Experimental Models of Amyotrophic Lateral Sclerosis," *Neurobiol. Dis.* 6(5):310-320, Academic Press, United States (1999).
Gibbons, J.A., et al., "Pharmacologic Characterization of CHIR 2279, an N-Substituted Glycine Peptoid with High-Affinity Binding for $\alpha_1$-Adenoceptors," *J. Pharmacol. Exp. Ther.* 277(2):885-899, American Society for Pharmacology and Experimental Therapeutics, United States (1996).
Lindvall, O., et al., "Neurotrophins and brain insults," *TINS* 17(11):490-496, Elsevier Science Ltd., England (1994).
Liu, H., et al., "Nerve growth factor induces anti-apoptotic heme oxygenase-1 in rat pheochromocytoma PC12 cells," *J. Neurochem.* 86(6):1553-1563, Blackwell Science, England (2003).
Longo, F.M., et al., "Small Molecule Neurotrophin Receptor Ligands: Novel Strategies for Targeting Alzheimer's Disease Mechanisms," *Curr. Alzheimer Res.* 4(5):503-506, Bentham Science Publishers, United Arab Emirates (2007).
Lykissas, M.G., et al., "The Role of Neurotrophins in Axonal Growth, Guidance, and Regeneration," *Curr. Neurovasc. Res.* 4:143-151, Bentham Science Publishers, Ltd., Netherlands (2007).
Martinez-Forero, I., et al., "1L-10 suppressor activity and ex vivo TR1 cell function are impaired in multiple sclerosis," *Eur. J. Immunol.* 38(2):576-586, Wiley-VCH, Germany (2008).
O'Reilly, A.M., et al., "HspB1 (Hsp 27) Expression and Neuroprotection in the Retina," *Mol. Neurobiol.* 42(2):124-132, Humana Press, United States (Jun. 2010).
Saragovi, H.U. and Zaccaro, M.C., "Small Molecule Peptidomimetic Ligands of Neurotrophin Receptors, Identifying Binding Sites, Activation Sites and Regulatory Sites," *Curr. Pharm. Des.* 8(24):2201-2206, Bentham Science Publishers, Netherlands (2002).

Schulte-Herbrüggen, O., et al., "Neurotrophin Factors—A Tool for Therapeutic Strategies in Neurological, Neuropsychiatric and Neuroimmunological Diseases?" *Curr. Med. Chem.* 14(22):2318-2329, Bentham Science Publishers Ltd., Netherlands (2007).
Sen, S.E. and Roach, S.L., "A Convenient Two-step Procedure for the Synthesis of Substituted Allylic Amines from Allylic Alcohols," *Synthesis*, pp. 756-758, United States (July 1995).
Shi, Z., et al., "Neurotrophic Rationale in Glaucoma: a TrkA Agonist, but Not NGF or a p75 Antagonist, Protects Retinal Ganglion Cells In Vivo," *Dev. Neurobiol.* 67(7):884-894, Wiley Subscription Services, Inc., United States (2007).
Tanaka, M., et al., "Intrathecal Upregulation of Granulocyte Colony Stimulating Factor and Its Neuroprotective Actions on Motor Neurons in Amyotrophic Lateral Sclerosis," *J. Neuropathol. Exp. Neurol.* 65(8):816-825, American Association of Neuropathologists, United States (2006).
Tuszynski, M.H. and Gage, F.H., "Bridging grafts and transient nerve growth factor infusions promote long-term central nervous system neuronal rescue and partial functional recovery," *Proc. Natl. Acad. Sci. USA* 92:4621-4625, National Aademy of Sciences, United States (1995).
Wu, C.W., et al., "Peptoid Oligomers with α-Chiral, Aromatic Side Chains: Effects of Chain Length on Secondary Structure," *J. Am. Chem. Soc.* 123(13):2958-2963, American Chemical Society, United States (2001).
Yuan, Y., et al., "The homeostasis of iron and suppression of HO-1 involved in the protective effects of nimodipine on neurodegeneration induced by aluminum overloading in mice," *Eur. J. Pharmacol.* 586(1-3):100-105, Elsevier Science, Netherlands (2008).
Zuckermann, R.N., et al., "Discovery of Nanomolar Ligands for 7-Transmembrane G-Protein-Coupled Receptors from a Diverse N-(Substituted)glycine Peptoid Library," *J. Med. Chem.* 37(17):2678-2685, American Chemical Society, United States (1994).
Restriction Requirement mailed Mar. 12, 2013, in U.S. Appl. No. 13/223,166, Villoslada et al., filed Aug. 31, 2011.
Office Action mailed Apr. 24, 2013, in U.S. Appl. No. 13/223,166, Villoslada et al., filed Aug. 31, 2011.
Office Action mailed Dec. 4, 2013, in U.S. Appl. No. 13/223,166, Villoslada et al., filed Aug. 31, 2011.
Notice of Allowability mailed Mar. 12, 2014, in U.S. Appl. No. 13/223,166, Villoslada et al., filed Aug. 31, 2011.
Office Action mailed Sep. 12, 2013, in U.S. Appl. No. 13/393,458, Moreno et al., having a §371(c) date of May 16, 2012.
Abad-Merin, M.J., et al., "Trimers of N-Alkylglycines Are Potent Modulators of the Multidrug Resistance Phenotype," *J. Pharmacol. Exp. Ther.* 313(1):112-120, American Society for Pharmacology and Experimental Therapeutics, United States (2005).
Anand, P. "Neurotrophic factors and their receptors in human sensory neuropathies," *Prog. Brain Res.* 146:477-492, Elsevier, Netherlands (2004).
Apfel, S.C., "Nerve growth factor for the treatment of diabetic neuropathy: what went wrong, what went right, and what does the future hold?" *Int. Rev. Neurobiol.* 50:393-413, Elsevier Science, Netherlands (2002).
Barker, P.A., "p75$^{NTR}$: A study in contrasts," *Cell Death Differ.* 5(5):346-356, Nature Publishing Group, England (1998).
Bhakar, A.L., et al., "A popotosis induced by p75NTR Overexpression Requires Jun Kinase-Dependent Phosphorylation of Bad," *J. Neurosci.* 23(36):11373-11381, Society for Neuroscience, United States (2003).
Burstein, D.E. and Green, L.A., "Evidence for RNA snthesis-dependent and -independent pathways in stimulation of neurite outgrowth by nerve growth factor," *Proc. Natl. Acad. Sci. USA* 75(12):6059-6063, National Academy of Sciences, United States (1978).
Chao, M.V., "Neurotrophins and Their Receptors: A Convergence Point for Many Signalling Pathways," *Nat. Rev. Neurosci.* 4(4):299-309, Nature Publishing Group, England (2003).
Faden, A.I. and Stoica, B., "Neuroprotection: Challenges and Opportunities," *Arch. Neurol.* 64(6):794-800, American Medical Assn., United States (2007).

(56) References Cited

OTHER PUBLICATIONS

Figliozzi, G.M., et al., "Synthesis of N-Substituted Glycine Peptoid Libraries" *Methods Enzymol.* 267:437-447,Academic Press, United States (1996).
Foehr, E.D., et al., "NF-κB Signaling Promotes Both Cell Survival and Neurite Process Formation in nerve Growth Factor-Stimulated PC12 Cells," *J. Neurosci.* 20(20): 7556-7563, Society for Neuroscience, United States (2000).
Frade, J.M., "Nuclear Translocation of the P75 Neurotrophin Receptor Cytoplasmic Domain in Response to Neurotrophin Binding," *J. Neurosci.* 25(6):1407-1411, Society for Neuroscience, United States (2005).
Gentry, J.J., et al., "Nerve Growth Factor Activation of Nuclear Factor κB through Its P75 Receptor is an Anti-apoptotic Signal in RN22 Schwannoma Cells," *J. Biol. Chem.* 275(11):7558-7565, American Society for Biochemistry and Molecular Biology, United States (2000).
Ghosh, S., et al., "NF-κB and Rel Proteins: Evolutionarily Conserved Mediators of Immune Responses," *Annu. Rev. Immunol.* 16:225-260, Annual Reviews Inc., United States (1998).
Goodson. B., et al., "Characterization of Novel Antimicrobial Peptoids," *Antimicrob. Agents Chemother.* 43(6):1429-1434, American Society for Microbiology, United States (1999).
Greene, L.A., and Tischler, A.S., "Establishment of an noradrenergic clonal line of rat adrenal pheochromocytoma cells which respond to nerve growth factor," *Proc. Natl. Acad. Sci. USA* 73(7):2424-2428, National Academy of Sciences, United States (1976).
Hellweg, R., et al., "Serum Concentrations of Nerve Growth Factor and Brain-Derived Neurotrophic Factor in Depressed Patients Before and After Antidepressant Treatment," *Pharmacopsychiatry* 41(2):66-71, Georg Thieme Verlag, Germany (2008).
Huang, E.J. and Reichardt, L.F., "Trk Receptors: Roles in Neuronal Signal Transduction," *Annu. Rev. Biochem:* 72:609-642, Annual Reviews, United States (2003).
Humet, M., et al., "A Positional Scanning Combinatorial Library of Peptoids as a Source of Biological Active Molecules: Identification of Antimicrobials," *J. Comb. Chem.* 5(5):597-605, American Chemical Society, United States (2003).
Kaplan, D.R. and Miller, F.D., "Neurotrophin signal transduction in the nervous system," *Curr. Opin. Neurobiol.* 10(3):381-391, Elsevier Science, England (2000).
Kirshenbaum, K., et al., "Sequence-specific polypeptoids: A diverse family of heteropolymers with stable secondary structure," *Proc. Natl. Acad. Sci. USA* 95(8):4303-4308, National Academy of Sciences, United States (1998).
Levi-Montalcini, R., "The Nerve Growth Factor 35 Years Later," *Science* 237(4819):1154-1162, American Association for the Advancement of Science, United States (1987).
Lewin, G.R. and Barde, Y.-A., "Physiology of the Neurotrophins," *Annu. Rev. Neurosci.* 19:289-317, Annual Reviews, Inc., United States (1996).
Longo, F.M., et al., "Synthetic NGF Peptide Derivatives Prevent Neuronal Death Via a P75 Receptor-Dependent Mechanism," *J. Neurosci. Res.* 48(1):1-17, Wiley Interscience, United States (1997).
Majdan, M. and Miller, F.D., "Neuronal Life and Death Decisions: Functional Antagonism Between the Trk and P75 Neurotrophin Receptors," *Int. J. Devl. Neuroscience* 17(3):153-161, Elsevier Science, England (1999).
Maliartchouk, S., et al., "Genuine Monovalent Ligands of Trka Nerve Growth Factor Receptors Reveal a Novel Pharmacological Mechanism of Action," *J. Biol. Chem.* 275(14):9946-9956, American Society for Biochemistry and Molecular Biology, United States (2000).
Maliartchouk, S., et al., "A designed peptidomimetic agonistic ligand of TrkA nerve growth factor receptors," *Mol. Pharmacol.* 57(2):385-391, American Society for Pharmacology and Experimental Therapeutics, United States (2000) (publication year incorrectly printed as 2007 on face page).
Masip, I., et al., "Synthesis of a Library of 3-Oxopiperazinium and Perhydro-3-oxo-1,4-diazepinium Derivatives and identification of Bioactive Compounds," *J. Comb. Chem.* 6(1):135-141, American Chemical Society, United States (2004).
Masip, I., et al., "Design and synthesis of an optimized positional scanning library of peptoids: identification of novel multidrug resistance reversal agents," *Bioorg, Med. Chem.* 13(6):1923-1929, Elsevier Science, England (2005).
Miller, S.M., et al., "Proteolytic studies of homologous peptides and N-substituted glycine peptoid oligomers," *Bioorg. Med. Chem. Lett.* 4(22):2657-2662, Elsevier Science, Great Britain (1994).
Montoliu, C., et al. "Prevention of in Vivo Excitotoxicity by a Family of Trialkylglycines, a Novel Class of Neuroprotectants," *J. Pharmacol. Exp. Ther.* 301(1):29-36, American Society for Pharmacology and Experimental Therapeutics, United States (2002).
Moreno, B., et al., "Methylthioadenosine Reverses Brain Autoimmune Disease," *Ann. Neurol.* 60(3):323-334, Wiley-Liss, United States (2006).
Palacios, R., et al., "A Network Analysis of the Human T-Cell Activation Gene Network Identifies Jagged1 as a Therapeutic Target for Autoimmune Diseases," *PLoS One* 2(11):e1222 1-15, Public Library of Science, United States (2007).
Palacios, R., et al., "Genomic regulation of CTLA4 and multiple sclerosis," *J. Neuroimmunol.* 203(1):108-115, Elsevier/North-Holland, Netherlands (2008).
Peleshok, J., and Saragovi, H.U., "Functional mimetics of neurotrophins and their receptors," *Biochem. Soc. Trans.* 34(Pt 4):612-617, Portland Press on The Behalf of The Biochemical Society, England (2006).
Planells-Cases, R., et al., "A Novel N-Methyl-D-Aspartate Receptor Open Channel Blocker with in Vivo Neuroprotectant Activity," *J. Pharmacol. Exp. Ther.* 302(1):163-713, American Society for Pharmacology and Experimental Therapeutics, United States (2002).
Poduslo, J.F. and Curran, G.L., "Permeability at the blood-brain and blood-nerve barriers of the neurotrophic factors: NGF, CNTF, NT-3, BDNF," *Mol. Brain Res.* 36(2):280-286, Elsevier Science Publishers, Netherlands (1996).
Price, R.D., et al., "Advances in small molecules promoting neurotrophic function," *Pharmacol. Ther.* 115(2):292-306, Pergamon press, England (2007).
Rabizadeh, S., et al., "Neurotrophin dependence mediated by p75$^{NTR}$: contrast between rescue by BDNF and NGF," *Cell Death Differ.* 6(12):1222-1227, Nature Publishing Group, England (1999).
Shoval, G., and Weizman, A., "The possible role of neurotrophins in the pathogenesis and therapy of schizophrenia," *Eur. Neuropsychopharmacol.* 15(3):319-329, Elsevier, Netherlands (2005).
Vajda, F.J., "Neuroprotection and neurodegenerative disease," *J. Clin. Neurosci.* 9(1):4-8, Humana Press, United States (2002).
Valera, E., et al., "Neuroprotection Against Excitotoxicity by N-Alkylglycines in Rat Hippocampal Neurons," *Neuromolecular Med.* 2(3):271-280, Humana Press, United States (2002).
Vicent, M.J. and Perez-Paya, E., "Poly-L-glutamic acid (PGA) Aided Inhibitors of Apoptotic Protease Activating Factor 1 (Apaf-1): An Antiapoptotic Polymeric Nanomedicine," *J. Med. Chem.* 49(13):3763-3765, American Chemical Society, United States (2006).
Villoslada, P., et al., "Human Nerve Growth Factor Protects Common Marmosets against Autoimmune Encephalomyelitis by Switching the Balance of T Helper Cell Type 1 and 2 Cytokines within the Central Nervous System," *J. Exp. Med.* 191(10:1799-1806, Rockefeller University Press, United States (2000).
Villoslada, P. et al., "Frequency, heterogeneity, and encephalitogenicity of T cells specific for myelin oligodendrocyte glycoprote in naïve outbred primates," *Eur. J. Immunol.* 31(10):2942-2950, Wiley-VCH, Germany (2001).
Villoslada, P. and Genain, C.P., "Role of nerve growth factor and other trophic factors in brain inflammation," *Prog. Brain Res.* 146:403-414, Elsevier, Netherlands (2004).
Williams, B. J., et al., "Nerve growth factor in treatment and pathogenesis of Alzheimer's disease," *Prog. Neurobiol.* 80(3):114-128, Pergamon Press, England (2006).

(56) References Cited

OTHER PUBLICATIONS

Youdim, M.B. and Buccafusco, J.J., "Multi-functional drugs for various CNS targets in the treatment of neurodegenerative disorders," *Trends Pharmacol. Sci.* 26(1):27-35, Elsevier in Association With The International Union of Pharmacology, England (2005).

Yoon, S.O., et al., "Competitive Signaling Between Trka and P75 Nerve Growth Factor Receptors Determines Cell Survival," *J. Neurosci.* 18(9):3273-3281, Society for Neuroscience, United States (1998).

Zaccaro, M.C., et al., "p75 Co-Receptors Regulatae Ligand-dependent and Ligand-independent Trk Receptor Activation, in Part by Altering Trk Docking Subdomains," *J. Biol. Chem.* 276(33):31023-31029, American Society for Biochemistry and Molecular Biology, United States (2001).

Zuckermann, R.N., et al., "Efficient Method for the Preparation of Peptoids [oligo(N-substituted glycines)]by Submonomer Solid-Phase Synthesis," *J. Am. Chem. Soc.* 114:10646-10647, American Chemical Society, United States (1992).

International Search Report and Written Opinion for International Application No. PCT/IB2010/002351, mailed Apr. 4, 2011, The European Patent Office, Rijswijk, The Netherlands.

International Preliminary Report on Patentability for International Application No. PCT/IB2010/002351, issued Mar. 6, 2012, The International Bureau of WIPO, Geneva, Switzerland.

International Search Report and Written Opinion for International Application No. PCT/IB2011/002562, mailed Jan. 23, 2012, The European Patent Office, Rijswijk, The Netherlands.

International Search Report for International Application No. PCT/ES 01/00369, mailed Jan. 16, 2002, along with English translation, The S.P.T.O., Madrid, Spain.

International Preliminary Examination Report for International Application No. PCT/ES01/00369, mailed Jan. 13, 2003, The European Patent Office, München, Germany.

European Search Report and Annex to European Search Report for European Patent Application No. EP 09 16 9045.3, mailed May 14, 2010, The European Patent Office, Berlin, Germany.

Montolio, M., et al., "A Semaphorin 3 A Inhibitor Blocks Axonal Chemorepulsion and Enhances Axon Regeneration," *Chem. Biol.* 16(7):691-701, Elsevier Ltd., United States (Jul. 2009).

Restriction Requirement mailed Nov. 7, 2012 in U.S. Appl. No. 13/393,458, Moreno et al., having a §371 (c) date of May 16, 2012.

Office Action mailed Jan. 25, 2013 in U.S. Appl. No. 13/393,458, Moreno et al., having a §371 (c) date of May 16, 2012.

\* cited by examiner

A:G79

B:G80

C:G81

D

A

B ized state that activates
AGONISTS OF NEUROTROPHIN RECEPTORS AND THEIR USE AS MEDICAMENTS This application claims the benefit of the earlier filing date of U.S. Provisional Application No. 61/378,823, filed Aug. 31, 2010, the entirety of which is incorporated by reference herein.

BACKGROUND OF THE INVENTION

1. Field of Invention

This invention applies to the area of therapeutics for neurological, psychiatric disorders, and ageing. In particular, it relates to the neuroprotective effect of small molecule agonists of neurotrophin (Nerve Growth Factor (NGF) or Brain-Derived Neurotrophic Factor (BDNF)) receptors and the use of those agonists as medicaments.

2. Background Art

Ageing, neurological and psychiatric disorders cause death and damage to nerve cells. Frequent and relevant damage to the nervous system can result from neuronal degeneration, ischemia, inflammation, immune responses, trauma, and cancer, among other things. As a consequence of these, nerve cells can die within minutes or hours or survive this initial damage in an impaired state that activates neurodegeneration, ending equally in cellular death.

Given the importance of the nervous system in enabling basic motor skills and sensing, there exists an interest in finding therapeutic weapons to protect the nervous system.

Neuroprotection is focused on the preservation, recovery, cure, or regeneration of the nervous system, its cells, structure, and function (Vajda et al., 2002). A goal of neuroprotection is to prevent or minimize the effects of an original damage to the nervous system, or to prevent or minimize the consequences of endogenous or exogenous noxious processes causing damage to axons, neurons, synapses, and dendrites.

Treatment strategies in general are frequently based on the modulation of a single proposed injury factor. Although such treatments can be shown to be beneficial in highly constrained animal models, they are less likely to prove efficacious in the more complex human disorder that involves more variable degrees of injury severity in a genetically diverse population (Faden and Stoica, 2007). Importantly, since the presumed mechanisms of neuronal death are both complex and varied, such as oxidative stress, mitochondrial dysfunction, protein aggregation, apoptosis, and inflammation (Youdim et al., 2005), single compounds having multipotential effects on multiple injury mechanisms are desirable.

Several neuroprotective drugs are under investigation including the following classes: anti-inflammatory agents, N-methyl D-aspartate (NMDA) antagonists, α-amino-3-hydroxy-5-methyl-4-isoxazole propionic acid (AMPA) antagonists, dexanabinol, sodium channel blockers, thyrotropin-releasing hormone (TRH), growth factors, glucocorticoids, caffeinol, opioid antagonists, apoptosis inhibitors, free radical trappers/scavengers, erythropoietin, calcium channel blockers, magnesium sulfate, and statins.

The ability of these pharmacological agents to limit secondary biochemical damage and cell death has been disappointing (Faden and Stoica, 2007).

Neurotrophins are growth factors that regulate the development and maintenance of the peripheral and the central nervous systems (Lewin and Barde, 1996). Nerve growth factor (NGF) is the first discovered and best characterized member of the neurotrophin family, which includes other structurally related proteins, such as brain-derived neurotrophic factor (BDNF). Nerve growth factor (NGF) is a homodimeric protein from the neurotrophin family that plays a crucial role in neuronal survival, differentiation and growth (Levi-Montalcini, 1987) and binds two distinct cellular receptors: the tyrosine kinase receptor TrkA and the p75 receptor (Chao, 2003). NGF-TrkA binding activates the intrinsic tyrosine kinase of the receptor, causing tyrosine phosphorylation of TrkA and associated signalling partners and therefore activating promotion of cell survival or differentiation (Kaplan and Miller, 2000). The p75 receptor is a member of the tumor necrosis factor receptor superfamily. Depending on the cellular environment and the type of ligand, p75 can act as transducer of pro-survival, pro-apoptotic, or pro-differentiation signals (Barker, 1998; Rabizadeh et al., 1999; Zaccaro et al., 2001; Saragovi and Zaccaro, 2002). Accordingly, depending on the metabolic route, binding to either TrkA or p75 receptors may trigger signals, depending on the cell type considered, linked to, indistinctly, differentiation and/or cell survival. Neurotrophins act through two main signaling pathways: the phosphatidylinositol 3-kinase (PI3K)-AKT pathway and the mitogen-activated protein kinase (MAPK)-MEK pathway (both pathways are involved in the inhibition of apoptosis). Neurotrophic factors are known to act also on mature neurons and in particular on injured and degenerative cells (Lindvall et al. 1994; Tuszynski and Gage 1995; Lykissas et al. 2007; Song et al. 2009).

The potential of NGF as a therapeutic agent for several diseases has been indicated by several investigators. Such diseases include neurodegenerative disorders, nerve inflammation and certain types of cancers, multiple sclerosis, neuromyelitis optica, amyotrophic lateral sclerosis (ALS), Parkinson's disease, Alzheimer's disease, Friedreich's ataxia, Huntington's disease, Dementia with Lewy bodies, spinal muscular atrophy, major depressive disorder, schizophrenia, glaucoma or peripheral neuropathies (diabetic or AIDS neuropathy) (Longo et al, 2007; Schulte-Herbrüggen, 2007; Shi, 2007; Hellveg, 2008; Shoval, 2005; Apfel, 2002; Anand, 2004). NGF has significant immunoregulatory properties during CNS inflammation to contribute to the maintenance of the CNS privilege (Villoslada and Genain, 2004). During Experimental Autoimmune Encephalomyelitis (EAE) in marmoset, NGF was able to inhibit the development of the clinical symptoms when administered intracerebroventricularly by continuous infusion apparently because of its ability to induce an immunosuppressive microenvironment in the CNS which leads to decreased CNS infiltration (Villoslada et al., 2000). The finding that NGF induces immunosuppression during autoimmune demyelination in addition to its neuroprotective properties in neurons and oligodendrocytes makes it a very good candidate for the treatment of CNS inflammatory diseases like MS. However, NGF is not the ideal drug candidate due to its inability to cross the blood-brain barrier (BBB) (Poduslo and Curran, 1996), its short half life and its side effects (Apfel, 2002). Much effort has been made in the search for small molecules with NGF agonist activity, with better pharmacokinetics and less side effects. To achieve this goal, different approaches have been attempted (Poduslo and Curran, 1996; Longo et al., 1997; Maliartchouk et al., 2000a; Maliartchouk et al., 2000b; Peleshok and Saragovi, 2006).

As such, there is an ongoing need for providing drugs, particularly NGF mimetics, with neuroprotective properties, which have preferably multipotential effects, but without the drawbacks of NGF. The present inventors have developed a family of compounds distinct from those disclosed in the art. The family of compounds of the invention are peptidomimetics of neurotrophins (NGF, BDNF), and agonists to TrkA, TrkB, and p75 specific receptors. Some of the compounds of the invention promote, as a way of example, cell survival to an extent even higher than NGF itself. The compounds of the invention are considered peptide-mimetics of neurotrophin and they all share a structure of N-alkylglycine trimers.

SUMMARY OF THE INVENTION

The present invention is related to the use of peptoid compounds of Formulae I-V, below, and the pharmaceutically acceptable salts and prodrugs thereof, as agonists of neurotrophin receptors, and specifically nerve growth factor (NGF) receptors and brain-derived neurotrophic factor (BDNF) receptors.

Compounds useful in the present invention have not been heretofore reported. Thus, one aspect of the present invention is directed to novel compounds of Formulae I-V, as well as their pharmaceutically acceptable salts and prodrugs.

Another aspect of the invention is directed to the use of compounds of any of Formulae I-V, and their pharmaceutically acceptable salts and prodrugs, as agonists of NGF receptors. Another aspect of the invention is directed to the use of compounds of any of Formulae I-V, and their pharmaceutically acceptable salts and prodrugs, as agonists of BDNF receptors.

A further aspect of the invention is to provide a compound of any of Formulae I-V, or a pharmaceutically acceptable salt or prodrug thereof, for use as a medicament. In one aspect of the invention, the medicament is for use in preventing or treating nerve cell death or damage. In one aspect of the invention, the medicament is for use in neuroprotection. In one aspect of the invention, the medicament is for use in regeneration of nerve cells. In one aspect of the invention, the medicament is for use in neuroenhancing. In one aspect, the medicament is for use in preventing or treating a neurological or a psychiatric disease. In one aspect of the invention, the medicament is for use in preventing or treating a disease selected from the group consisting of a neurological disease, a preferentially neurodegenerative disorder (such as amyotrophic lateral sclerosis (ALS), Parkinson's disease, Alzheimer's disease, Friedreich's ataxia, Huntington's disease, Dementia with Lewy bodies, and spinal muscular atrophy), nerve inflammation (such as multiple sclerosis and neuromyelitis optica), major depressive disorder, schizophrenia, glaucoma, peripheral neuropathy (such as diabetic or AIDS neuropathy), and cancer (such as glioblastoma, astrocytoma, meduloblastoma, neurinoma, neuroblastoma, meningioma, colon cancer, pancreatic cancer, breast cancer, prostate cancer, leukemia, acute lymphocytic leukemia, osteosarcoma, hepatocellular carcinoma, ovarian carcinoma, lung adenocarcinoma, and esophagic carcinoma).

A further aspect of the invention is to provide a compound of any of Formulae I-V, or a pharmaceutically acceptable salt or prodrug thereof, for use as a medicament for treating multiple sclerosis.

A further aspect of the invention is to provide a compound of any of Formulae I-V, or a pharmaceutically acceptable salt or prodrug thereof, for use as a medicament, wherein the medicament is a neuroregenerative drug.

A further aspect of the invention is to provide a compound of any of Formulae I-V, or a pharmaceutically acceptable salt or prodrug thereof, for use as a medicament, wherein the medicament is an immunomodulator.

A further aspect of the invention is to provide a compound of any of Formulae I-V, or a pharmaceutically acceptable salt or prodrug thereof, for use as a medicament, wherein the medicament has a combination of neuroprotective and immunomodulatory effects.

A further aspect of the present invention is to provide a pharmaceutical composition, comprising a therapeutically effective amount of at least one compound of any of Formulae I-V, or a pharmaceutically acceptable salt or prodrug thereof, and a pharmaceutically acceptable carrier.

A further aspect of the invention is to provide the use of a compound of any of Formulae I-V, or a pharmaceutically acceptable salt or prodrug thereof, in the manufacture of a medicament for preventing or treating nerve cell death or damage.

A further aspect of the invention is to provide the use of a compound of any of Formulae I-V, or a pharmaceutically acceptable salt or prodrug thereof, in the manufacture of a medicament for providing neuroprotection.

A further aspect of the invention is to provide the use of a compound of any of Formulae I-V, or a pharmaceutically acceptable salt or prodrug thereof, in the manufacture of a medicament for the regeneration of nerve cells.

A further aspect of the invention is to provide the use of a compound of any of Formulae I-V, or a pharmaceutically acceptable salt or prodrug thereof, in the manufacture of a medicament for preventing or treating a neurological disease or a psychiatric disease.

A further aspect of the invention is to provide the use of a compound of any of Formulae I-V, or a pharmaceutically acceptable salt or prodrug thereof, in the manufacture of a medicament for preventing or treating a disease selected from the group consisting of a neurological disease, a preferentially neurodegenerative disorder (such as amyotrophic lateral sclerosis (ALS), Parkinson's disease, Alzheimer's disease, Friedreich's ataxia, Huntington's disease, Dementia with Lewy bodies, and spinal muscular atrophy), nerve inflammation (such as multiple sclerosis and neuromyelitis optica), major depressive disorder, schizophrenia, glaucoma, peripheral neuropathy (such as diabetic or AIDS neuropathy), and cancer (such as glioblastoma, astrocytoma, meduloblastoma, neurinoma, neuroblastoma, meningioma, colon cancer, pancreatic cancer, breast cancer, prostate cancer, leukemia, acute lymphocytic leukemia, osteosarcoma, hepatocellular carcinoma, ovarian carcinoma, lung adenocarcinoma, and esophagic carcinoma).

A further aspect of the invention is to provide the use of a compound of any of Formulae I-V, or a pharmaceutically acceptable salt or prodrug thereof, in the manufacture of a medicament for preventing or treating multiple sclerosis.

A further aspect of the invention is to provide the use of a compound of any of Formulae I-V, or a pharmaceutically acceptable salt or prodrug thereof, in the manufacture of a neuroregenerative drug.

A further aspect of the invention is to provide the use of a compound of any of Formulae I-V, or a pharmaceutically acceptable salt or prodrug thereof, in the manufacture of an immunomodulator.

A further aspect of the invention is to provide the use of a compound of any of Formulae I-V, or a pharmaceutically acceptable salt or prodrug thereof, in the manufacture of a medicament having a combination of neuroprotective and immunomodulatory effects.

A further aspect of the invention is to provide the use of a compound of any of Formulae I-V, or a pharmaceutically acceptable salt or prodrug thereof, in the manufacture of a neuroenhancing drug.

A further aspect of the invention is to provide a method for preventing or treating nerve cell death or damage, comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method for providing neuroprotection, comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method for providing immunomodulation, comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method for regenerating nerve cells, comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method for preventing or treating a disease selected from the group consisting of a neurological disease, a preferentially neurodegenerative disorder (such as amyotrophic lateral sclerosis (ALS), Parkinson's disease, Alzheimer's disease, Friedreich's ataxia, Huntington's disease, Dementia with Lewy bodies, and spinal muscular atrophy), nerve inflammation (such as multiple sclerosis and neuromyelitis optica), major depressive disorder, schizophrenia, glaucoma, peripheral neuropathy (such as diabetic or AIDS neuropathy), and cancer (such as glioblastoma, astrocytoma, meduloblastoma, neurinoma, neuroblastoma, meningioma, colon cancer, pancreatic cancer, breast cancer, prostate cancer, leukemia, acute lymphocytic leukemia, osteosarcoma, hepatocellular carcinoma, ovarian carcinoma, lung adenocarcinoma, and esophagic carcinoma), comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method for preventing or treating multiple sclerosis, Alzheimer's disease, Parkinson's disease, or glaucoma, comprising administering to a subject in need thereof an effective amount of a compound of any of Formulae I-V, or a pharmaceutically acceptable salt or prodrug thereof, or an effective amount of a pharmaceutical composition comprising a compound of any of Formulae I-V, or a pharmaceutically acceptable salt or prodrug thereof.

A further aspect of the invention is to provide a method of treating a disease responsive to the stimulation of the activity of neurotrophin, or a neurotrophin receptor, in a mammal suffering from lack of stimulation thereof, comprising administering an effective amount a compound of any of Formulae I-V, or a pharmaceutically acceptable salt or prodrug thereof.

A further aspect of the invention is to provide a compound of any of Formulae I-V, or a pharmaceutically acceptable salt or prodrug thereof, for use in stimulating the activity of neurotrophin, or a neurotrophin receptor.

A further aspect of the present invention is to provide a method of stimulating neurotrophin receptor activity in a subject in need thereof, comprising administering a compound of any of Formulae I-V, or a pharmaceutically acceptable salt or prodrug thereof, to the subject. In one embodiment, the neurotrophin receptor is TrkA receptor, TrkB receptor, or p75 receptor.

A further aspect of the invention is to provide a method of treating a disease responsive to the stimulation of the activity of nerve growth factor, or a nerve growth factor receptor, in a mammal suffering from lack of stimulation thereof, comprising administering an effective amount a compound of any of Formulae I-V, or a pharmaceutically acceptable salt or prodrug thereof.

A further aspect of the invention is to provide a compound of any of Formulae I-V, or a pharmaceutically acceptable salt or prodrug thereof, for use in stimulating the activity of nerve growth factor, or a nerve growth factor receptor.

A further aspect of the present invention is to provide a method of stimulating nerve growth factor receptor activity in a subject in need thereof, comprising administering a compound of any of Formulae I-V, or a pharmaceutically acceptable salt or prodrug thereof, to the subject. In one embodiment, the nerve growth factor receptor is TrkA receptor or p75 receptor.

A further aspect of the invention is to provide a method of treating a disease responsive to the stimulation of the activity of brain-derived neurotrophic factor, or a brain-derived neurotrophic factor receptor, in a mammal suffering from lack of stimulation thereof, comprising administering an effective amount a compound of any of Formulae I-V, or a pharmaceutically acceptable salt or prodrug thereof.

A further aspect of the invention is to provide a compound of any of Formulae I-V, or a pharmaceutically acceptable salt or prodrug thereof, for use in stimulating the activity of brain-derived neurotrophic factor, or a brain-derived neurotrophic factor receptor.

A further aspect of the present invention is to provide a method of stimulating brain-derived neurotrophic factor receptor activity in a subject in need thereof, comprising administering a compound of any of Formulae I-V, or a pharmaceutically acceptable salt or prodrug thereof, to the subject. In one embodiment, the nerve growth factor receptor is TrkB receptor or p75 receptor.

A further aspect of the present invention is to provide a method of preparing a pharmaceutical composition, comprising admixing an effective amount of a compound of any of Formulae I-V, or a pharmaceutically acceptable salt or prodrug thereof, with a pharmaceutically acceptable carrier.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and not restrictive of the invention as claimed.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

FIG. 1A-1E depict the results of Example 2 on G79, G80, and G81 in the dose response differentiation assay in PC12 cell line. FIG. 1A. depicts images of PC12 cells differentiated in the presence of G79. FIG. 1B depicts images of PC12 cells differentiated in the presence of G80. FIG. 1C depicts images of PC12 cells differentiated in the presence of G81. FIG. 1D shows the number of differentiated cells in the dose response differentiation assay. FIG. 1E shows the percentage of differentiated cells calculated relative to NGF induced differentiation. Data are the mean±SEM of at least three experiments, each in duplicate.

FIG. 2 shows effects of G79, G80, and G81 in promotion of RN22 cell survival. Depicted are the means±S.E. of three experiments, each in duplicate. *p<0.05, **p<0.01 (ANOVA) respect to stress control.

FIG. 3A-3E depict the effects of G79, G80, and G81 in secretagogue activity assay (FIG. 3A), in synergistic activity assay (FIG. 3B), in TrkA activation assay (FIG. 3C), in signalling inhibition assay in the presence of LY294002 (FIG. 3D), and in signalling inhibition assay in the presence of PD98059 (FIG. 3E). FIG. 3F-3J show the effects depicted in FIG. 3A-3E, respectively, as percentages of differentiated cells calculated relative to NGF induced differentiation.

FIG. 4 depicts the results of G79 in a glaucoma model. FIG. 4A shows the count of the retinal ganglion cells for control, placebo, 200 µg/ml NGF, 200 µg/ml G79, and 400 µg/ml G79. FIG. 4B shows retina sections after treatment with control, placebo, 200 µg/ml NGF, 200 µg/ml G79, and 400 µg/ml G79. FIG. 4C shows the count of the retinal ganglion cells for control, placebo, 200 µg/ml G79, Timolol, and 200 µg/ml G79 and Timolol.

Figure 9:
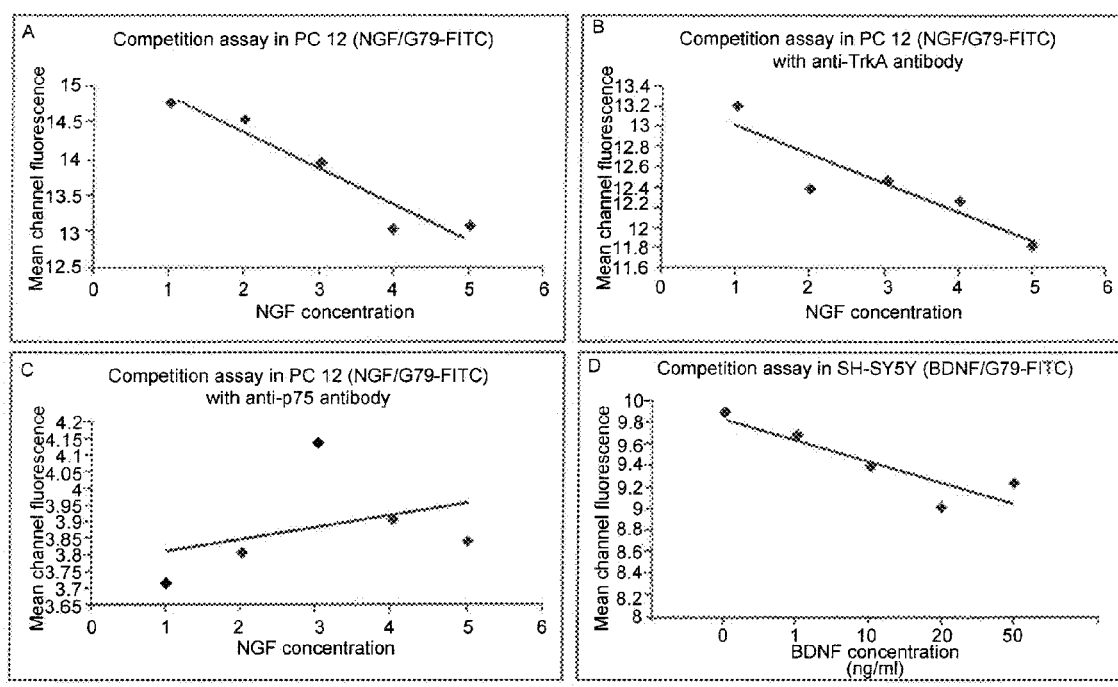

FIG. 9 depicts the effects of G79 in the cytometry binding assay of Example 13. FIG. 9A shows the mean channel fluorescence (MCF) in the competition assay in PC12 (NGF/G79-FITC). FIG. 9B shows the MCF in the competition assay in PC12 (NGF/G79-FITC) with anti-TrkA antibody. FIG. 9C shows the MCF in the competition assay in PC12 (NGF/G79-FITC) with anti-p76 antibody. FIG. 9D shows the MCF in the competition assay in SH-SY5Y (BDNF/G79-FITC).

Figure 10:
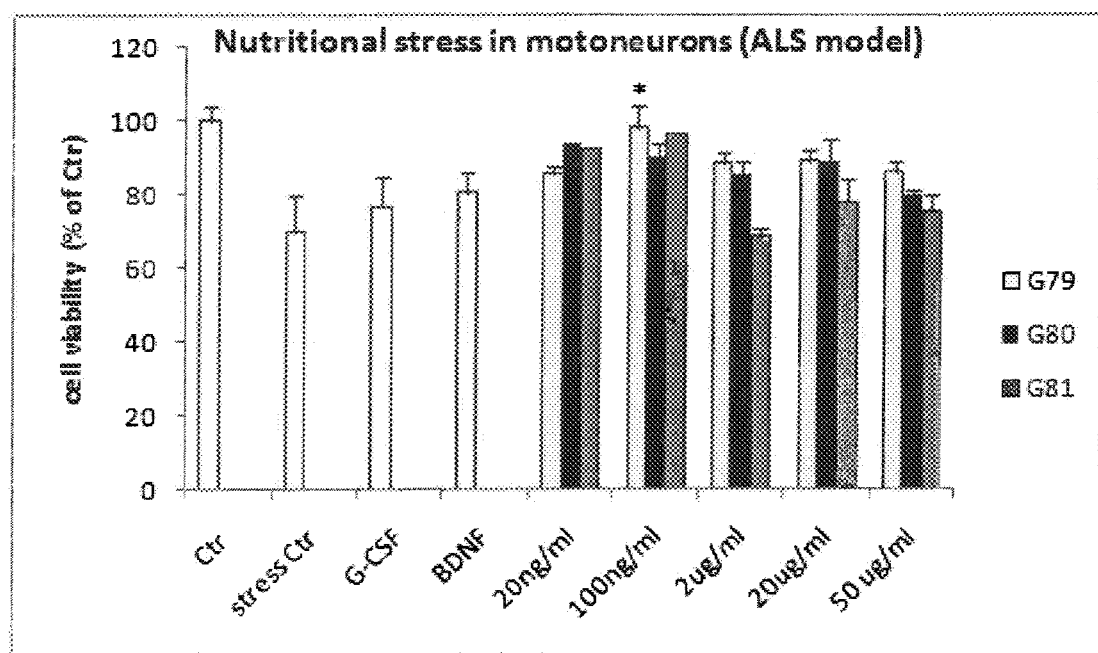

FIG. 10 depicts the results of G79, G80, and G81 in in vitro model of amyotrophic lateral sclerosis (ALS).

Figure 11A:
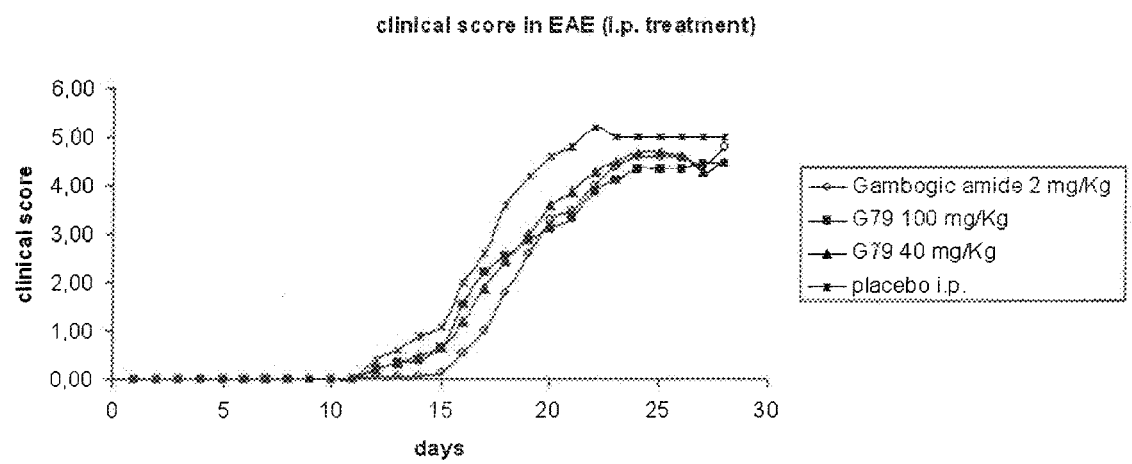
Figure 11B:
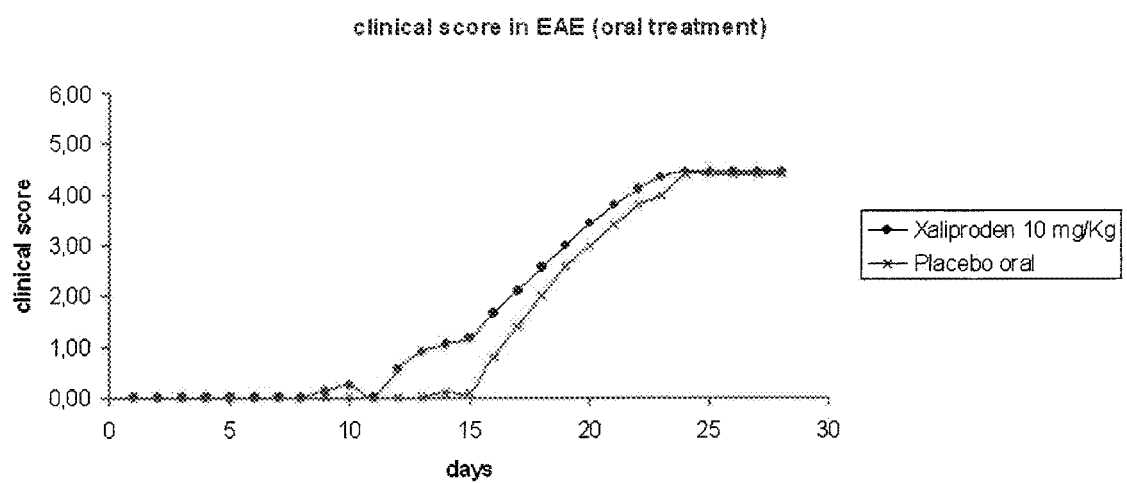

FIG. 11A-11B show the results of G79, Gambogic amide and Xaliproden in the preventative application in in vivo model of MS after i.p. administration of G79 or Gambogic amide (FIG. 11A) and after oral administration of Xaliproden (FIG. 11B).

Figure 12:
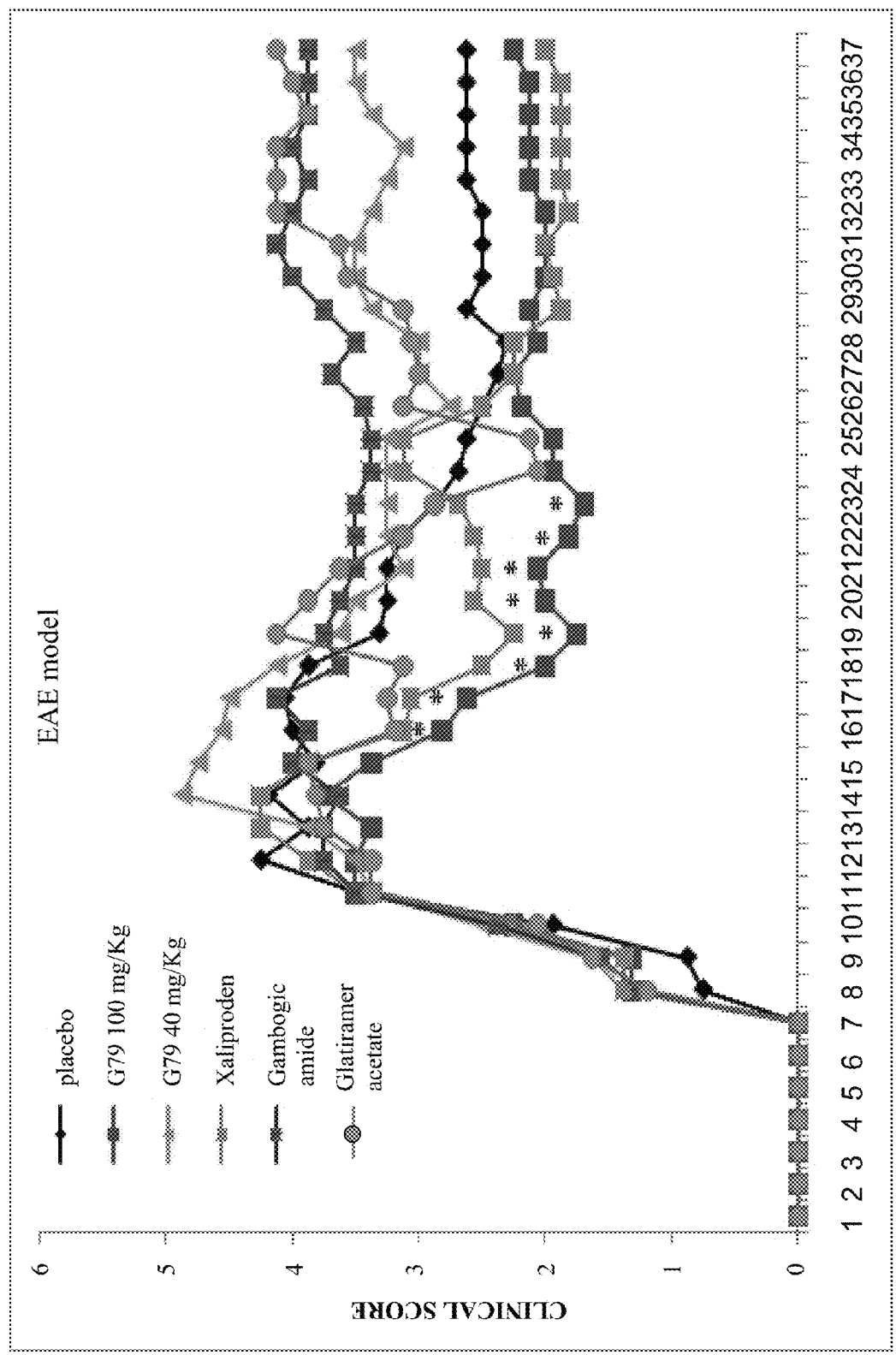

FIG. 12 shows the results of G79, Gambogic amide, Xaliproden, and Glatiramer acetate in the curative application in in vivo model of MS after i.p. administration.

Figure 13:
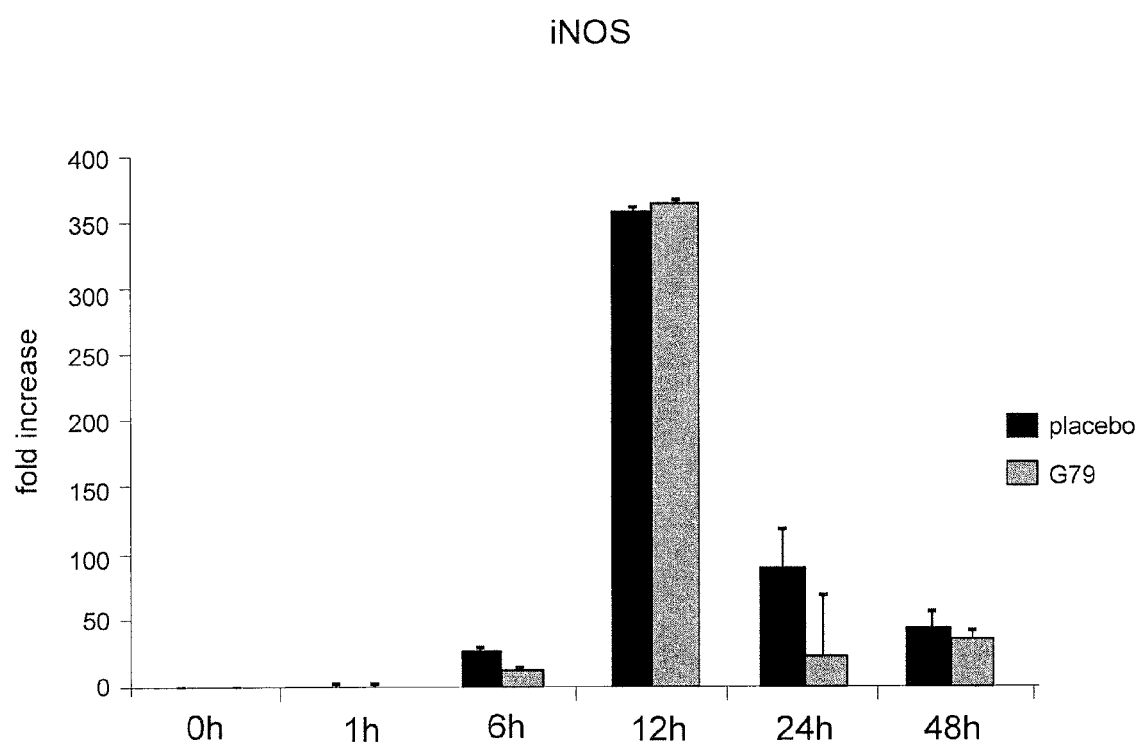

FIG. 13 depicts the results of the effect of G79 in the induction of the enzyme iNOS over 48 hours.

Figure 14A:
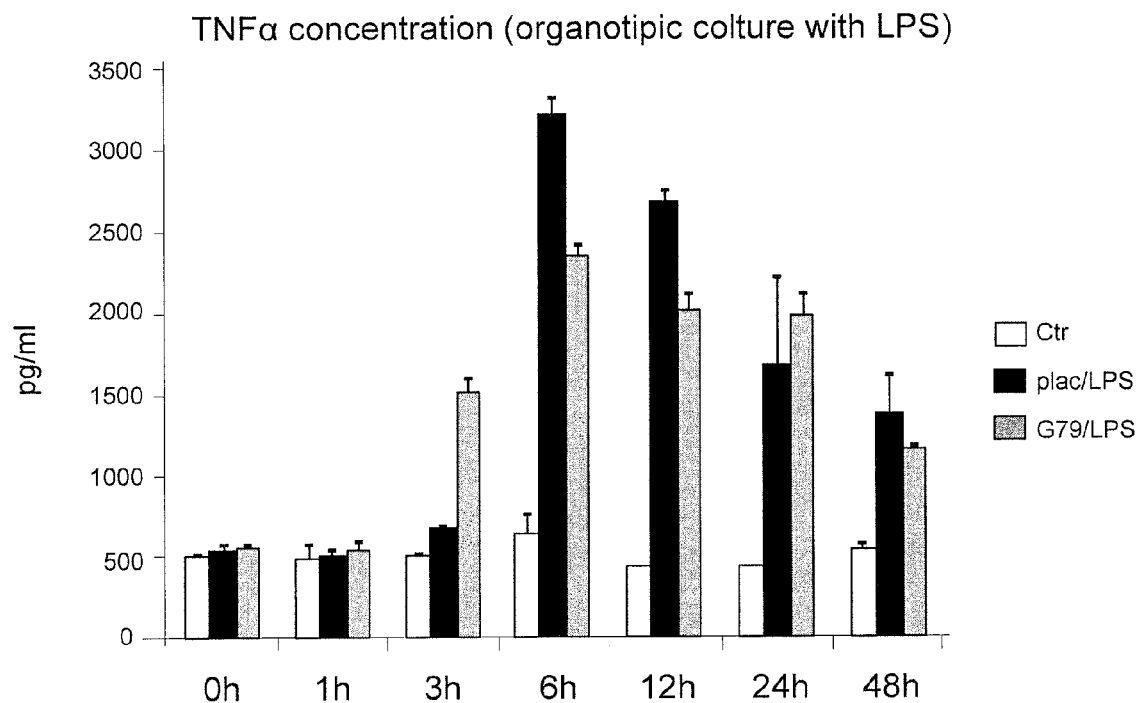
Figure 14B:
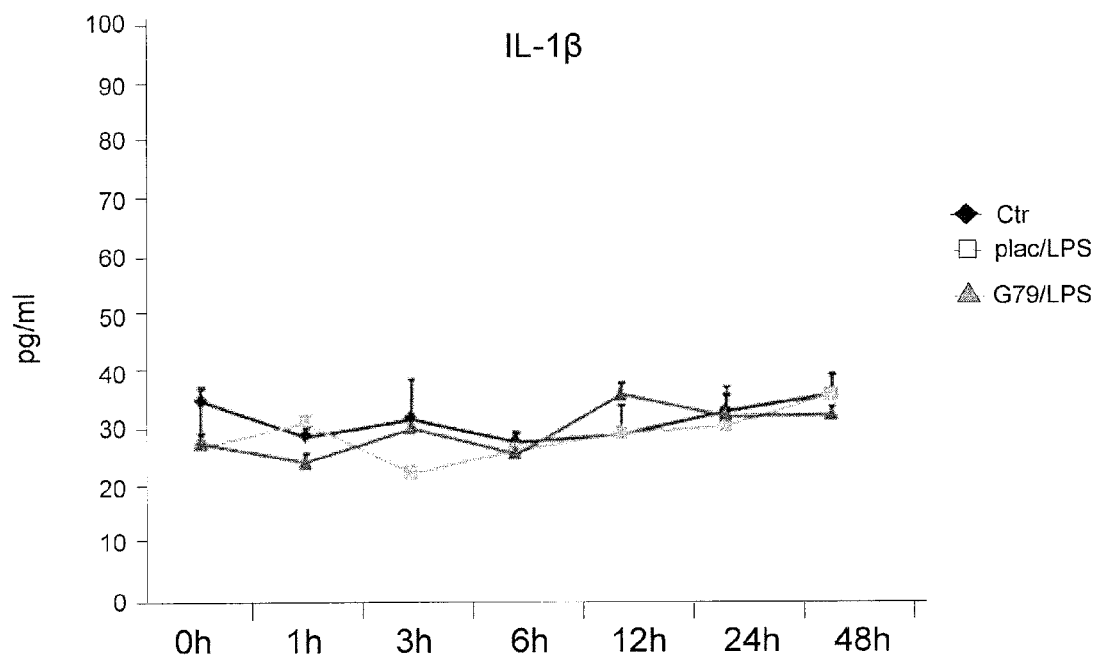

FIG. 14A-14B depict the results of G79 in the in vitro model for neuroinflammation. FIG. 14A shows the production of TNFα in cerebellar organitypic culture and FIG. 14B shows the production of IL-1β in organotypic cerebellar culture.

DETAILED DESCRIPTION OF THE INVENTION

One aspect of the invention is based on the use of compounds of Formulae I-V, and the pharmaceutically acceptable salts and prodrugs thereof, as agonists of neurotrophin receptors, and especially agonists of nerve growth factor (NGF) receptors and brain-derived neurotrophic factor (BDNF) receptors. In view of this property, compounds of Formulae I-V, and the pharmaceutically acceptable salts and prodrugs thereof, are useful for preventing or treating diseases responsive to the stimulation of neurotrophin receptors, and especially nerve growth factor or a nerve growth factor receptor, or brain-derived neurotrophic factor or a brain-derived neurotrophic factor receptor.

Compounds of any of Formula I-V show a good NGF like activity "in vitro" by inducing differentiation of PC12 cells and promoting cell survival of RN22 cells and, therefore, have neuroprotective properties.

The compounds useful in this aspect of the invention are compounds represented by Formula I:

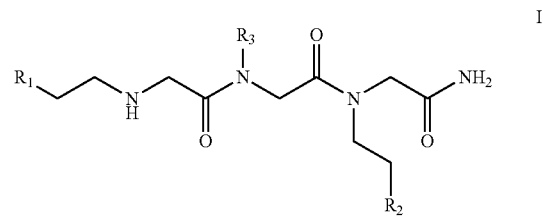

and pharmaceutically acceptable salts and prodrugs thereof, wherein $R_1$ is phenyl substituted with halogen or trifluoromethyl, and further optionally substituted with one or two substituents selected from the group consisting of halogen, $C_{1-6}$ alkyl, $(C_{1-6})$alkoxy, and halo$(C_{1-6})$alkyl; or $R_1$ is pyrrolidin-1-yl;

$R_2$ is 2-oxo-pyrrolidin-1-ylmethyl or sulfamoylphenyl; and $R_3$ is chosen from propyl, 1-methylethyl, butyl, 2-methylpropyl, pentyl, 1-methylbutyl, 2-methylbutyl, hexyl, 4-methylpentyl, 3-methylpentyl, 2-methylpentyl, and 1-methylpentyl.

In one embodiment, compounds useful in the present invention are compounds of Formula I, wherein $R_1$ is fluorophenyl. In one embodiment, the fluorophenyl group is 2-fluorophenyl, 3-fluorophenyl or 4-fluorophenyl. Preferably, $R_1$ is 2-fluorophenyl. In one embodiment, the fluorophenyl group is further substituted with one or two substituents selected from the group consisting of halogen, $C_{1-6}$ alkyl, $(C_{1-6})$alkoxy, and halo$(C_{1-6})$alkyl; preferably one or two substituents selected from the group consisting of halogen, $C_{1-4}$ alkyl, $(C_{1-4})$alkoxy, and halo$(C_{1-4})$alkyl; more preferably one or two substituents selected from the group consisting of halogen, methyl, ethyl, propyl, isopropyl, methoxy, ethoxy, fluoromethyl, and trifluoromethyl.

In one embodiment, compounds useful in the present invention are compounds of Formula I, wherein $R_1$ is chlorophenyl. In one embodiment, the chlorophenyl group is 2-chlorophenyl, 3-chlorophenyl or 4-chlorophenyl. In one embodiment, $R_1$ is 2-chlorophenyl. In one embodiment, the chlorophenyl group is further substituted with one or two substituents selected from the group consisting of halogen, $C_{1-6}$alkyl, $(C_{1-6})$alkoxy, and halo$(C_{1-4})$alkyl; preferably one or two substituents selected from the group consisting of halogen, $C_{1-4}$ alkyl, $(C_{1-4})$alkoxy, and halo$(C_{1-4})$alkyl; more preferably one or two substituents selected from the group consisting of halogen, methyl, ethyl, propyl, isopropyl, methoxy, ethoxy, fluoromethyl, and trifluoromethyl.

In one embodiment, compounds useful in the present invention are compounds of Formula I, wherein $R_1$ is bromophenyl. In one embodiment, the bromophenyl group is 2-bromophenyl, 3-bromophenyl or 4-bromophenyl. In one embodiment, $R_1$ is 2-bromophenyl. In one embodiment, the bromophenyl group is further substituted with one or two substituents selected from the group consisting of halogen, $C_{1-6}$ alkyl, $(C_{1-6})$alkoxy, and halo$(C_{1-6})$alkyl; preferably one or two substituents selected from the group consisting of halogen, $C_{1-4}$ alkyl, $(C_{1-4})$alkoxy, and halo$(C_{1-4})$alkyl; more preferably one or two substituents selected from the group consisting of halogen, methyl, ethyl, propyl, isopropyl, methoxy, ethoxy, fluoromethyl, and trifluoromethyl.

In one embodiment, compounds useful in the present invention are compounds of Formula I, wherein $R_1$ is iodophenyl. In one embodiment, the iodophenyl group is 2-iodophenyl, 3-iodophenyl or 4-iodophenyl. In one embodiment, $R_1$ is 2-iodophenyl. In one embodiment, the iodophenyl group is further substituted with one or two substituents selected from the group consisting of halogen, $C_{1-6}$alkyl, $(C_{1-6})$alkoxy, and halo$(C_{1-6})$alkyl; preferably one or two substituents selected from the group consisting of halogen, $C_{1-4}$ alkyl, $(C_{1-4})$alkoxy, and halo$(C_{1-4})$alkyl; more preferably one or two substituents selected from the group consisting of halogen, methyl, ethyl, propyl, isopropyl, methoxy, ethoxy, fluoromethyl, and trifluoromethyl.

In one embodiment, compounds useful in the present invention are compounds of Formula I, wherein $R_1$ is trifluoromethylphenyl. In one embodiment, the trifluoromethylphenyl group is 2-trifluoromethylphenyl, 3-trifluoromethylphenyl or 4-trifluoromethylphenyl. Useful compounds include those where $R_1$ is 2-trifluoromethylphenyl. In one embodiment, the trifluoromethylphenyl group is further substituted with one or two substituents selected from the group consisting of halogen, $C_{1-6}$alkyl, $(C_{1-6})$alkoxy, and halo$(C_{1-6})$alkyl; preferably one or two substituents selected from the group consisting of halogen, $C_{1-4}$alkyl, $(C_{1-4})$alkoxy, and halo$(C_{1-4})$alkyl; more preferably one or two substituents selected from the group consisting of halogen, methyl, ethyl, propyl, isopropyl, methoxy, ethoxy, fluoromethyl, and trifluoromethyl.

In one embodiment, compounds useful in the present invention are compounds of Formula I, wherein $R_1$ is pyrrolidin-1-yl.

In one embodiment, compounds useful in the present invention are compounds of Formula I, wherein $R_2$ is 2-oxo-pyrrolidin-1yl-methyl.

In one embodiment, compounds useful in the present invention are compounds of Formula I, wherein $R_2$ is sulfamoylphenyl. In one embodiment, the sulfamoylphenyl group is 2-sulfamoylphenyl, 3-sulfamoylphenyl, or 4-sulfamoylphenyl. Preferably, $R_2$ is 4-sulfamoylethyl.

In one embodiment, compounds useful in the present invention are compounds of Formula I, where $R_3$ is 2-methylpropyl, having the Formula II:

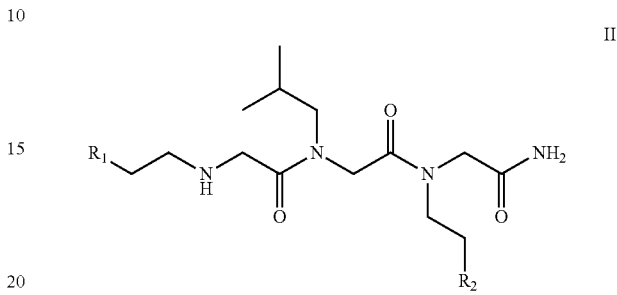

and pharmaceutically acceptable salts and prodrugs thereof, wherein $R_1$ is and $R_2$ are as defined above for Formula I.

In one embodiment, compounds useful in the present invention are compounds of Formulae I-II, and pharmaceutically acceptable salts and prodrugs thereof, wherein $R_1$ is 2-fluorophenyl or pyrrolidin-1-yl, and $R^2$ is 2-oxo-pyrrolidin-1-ylmethyl or 4-sulfamoylphenyl as follows:

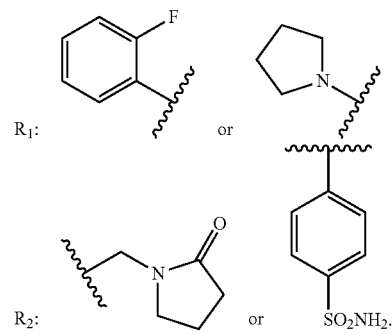

Preferred compounds according to present invention are compounds of Formula I, represented by any of the following Formulae III-V, and their pharmaceutically acceptable salts and prodrugs:

Formula III:

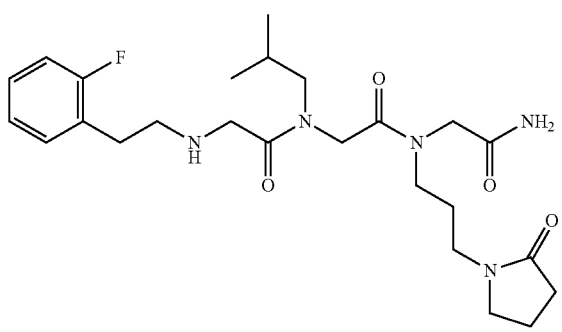

[N-(2-(2'-Fluorophenyl)ethyl)glycyl]-[N-(2-methylpropyl)glycyl]-N-[3-(2'-oxopyrrolidinyl)propyl]glycinamide (G79);

Formula IV:

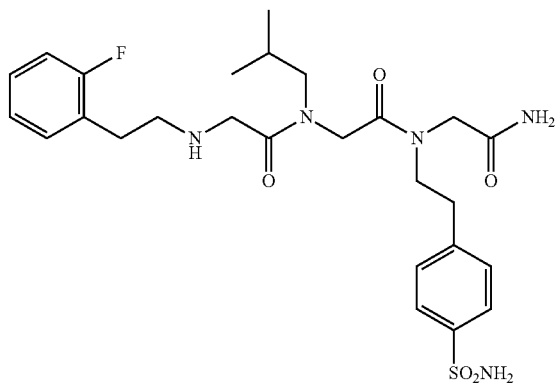

[N-(2-(2'-Fluorophenyl)ethyl)glycyl]-N-[2-(4'-sulfamoylphenyl)ethyl]glycinamide (G80); and Formula V:

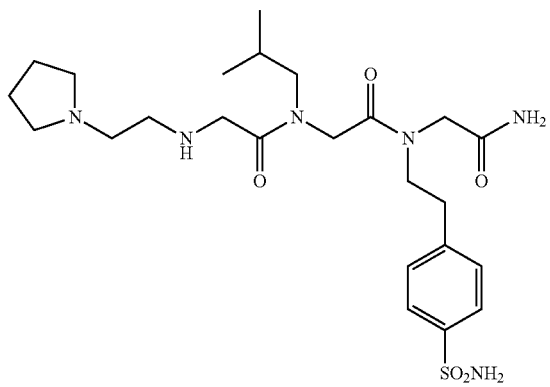

[N-(2-(1-Pyrrolidinyl)ethyl)glycyl]-[N-(2-methylpropyl)glycyl]-N-[2-(4'-sulfamoylphenyl)ethyl]glycinamide (G81),
and pharmaceutically acceptable salts and prodrugs thereof.

In one embodiment, the compound of Formula I is the compound of Formula III, or a pharmaceutically acceptable salt or prodrug thereof.

In one embodiment, the compound of Formula I is the compound of Formula IV, or a pharmaceutically acceptable salt or prodrug thereof.

In one embodiment, the compound of Formula I is the compound of Formula V, or a pharmaceutically acceptable salt or prodrug thereof.

Useful halogen groups include fluorine, chlorine, bromine and iodine.

Useful alkyl groups are selected from straight-chained and branched $C_{1-6}$ alkyl groups, and more preferably straight chain $C_{1-4}$ alkyl groups and branched chain $C_{1-4}$ alkyl groups. Typical $C_{1-6}$ alkyl groups include methyl, ethyl, propyl, isopropyl, butyl, sec-butyl, tert-butyl, iso-butyl, 3-pentyl, hexyl, among others.

Useful halo($C_{1-6}$)alkyl groups include any of the above-mentioned $C_{1-6}$ alkyl groups substituted by one or more fluorine, chlorine, bromine or iodine atoms (e.g., fluoromethyl, difluoromethyl, trifluoromethyl, pentafluoroethyl, 1,1-difluoroethyl and trichloromethyl groups). Preferably, the halo($C_{1-6}$)alkyl group is trifluoromethyl.

Useful $C_{1-6}$ alkoxy groups include oxygen substituted by one of the $C_{1-6}$ alkyl groups mentioned above (e.g., methoxy, ethoxy, propoxy, iso-propoxy, butoxy, tert-butoxy, iso-butoxy, sec-butoxy, and pentyloxy).

It has been found that the compounds of Formula III-V induce differentiation in PC12 cells and survival of RN22 cells after stress induction. The mechanism of action of the compounds of Formulae III-V has been investigated. Accordingly, the effect of the compounds of Formulae III-V together with NGF in culture was tested. If the compounds work as ligands or interfere in the pathway induced by NGF, they may inhibit the activity of NGF. Otherwise if the compounds produce an additive effect, they may work through a parallel mechanisms. As a result, we found that G79, G80 and G81 do not produce an additive effect in combination with NGF. There is not a big difference in the number of differentiated cells in the treatment with only the compound compared to the combination treatment. It means that the compounds of Formulae III-V act in the same pathway of NGF. The reduction in the NGF neurotrophic response correspond to a profile of a partial agonist of NGF.

To better understand the binding of the compounds of Formulae III-V to the cell surface, PC12 cells were treated with NGF or the compounds in the presence of the antibody anti-TrkA that blocks the binding site of TrkA for NGF in the extracellular domain. Therefore, if peptidomimetics exert their activity by activating the binding site, the presence of this antibody will prevent their activity. Otherwise, if the activity on NGF pathway is maintained, it will indicate that neurotrophin peptidomimetics exert their activity by activating TrkA in other point of the molecule different of the binding site of TrkA. The results shows that while NGF neurotrophic activity was reduced by adding into the culture the antibody anti-TrkA, the percentage of differentiation between the treatment with the compounds alone or the compounds in combination with the antibody was not very different. It may suggest that the activity of the compounds is not mediated by the binding to the extracellular portion of the TrkA receptor. However, this result does not exclude that the compounds of Formulae III-V bind either the intracellular portion of the TrkA or other members of intracellular signalling pathway. It was also found that G79 competes with NGF and BDNF for the binding to neurotrophin receptors. This effect may be due to the competition on the p75 receptor, which is much higher expressed on the cell surface of the cell lines that were used in the experiments.

The possibility that the compounds of Formulae III-V may act as secretagogues, inducing their effects through the up-regulation of the synthesis of NGF was also considered. It was found that while the treatment of NGF together with the antibody anti-NGF induces a reduction in the differentiation of PC12 cells, there is no difference in the percentage of differentiation induced by G79, G80 and G81 in the presence of the same antibody compared to the treatment with the compounds alone. For this reason, G79, G80, and G81 do not act as secretagogues.

To study the mechanism of action of the compounds of Formulae III-V, it was investigated if the neurotrophic activity of the molecules depends on AKT and ERK activation, the two main pathways of TrkA signaling. It was found that as the treatment with NGF in combination with the inhibitors LY294002 or PD98059 reduces the percentage of differentiation in PC12 cells compared to the treatment with only NGF, also the percentage of differentiation with G79, G80 and G81 in combination with the inhibitors is reduced compared to the treatment with the compounds alone.

As a conclusion, the NGF-like small molecules of the present invention induce differentiation without activating the synthesis of NGF. They also act through the activation of PI3K/AKT and MAPK/ERK TrkA pathways without binding to the extracellular portion of TrkA.

The ability of the compounds of Formula III-V to activate the neurotrophin pathways was tested in differentiation assays in the presence of inhibitors of Pi3K and MAPkinase pathways together with Luminex assays. According to the results, compounds G79, G80, and G81 activate the neurotrophin pathway. For example, heat-shock proteins such as HSP-27, can be activated by different agents and neurotrophic factors (Liu H. et al, J. Neurochem., 86, 1553-1563, 2003; Yuan Y et al, Eur. J. Pharmacol. 586, 100-105, 2008; O'Reilly A M et al, Mol Neurobiol, 42, 124-132, 2010). The conducted tests show that HSP-27 is significantly activated after G79 in vitro stimulation, similarly to NGF.

The effect of the compounds of Formula III-V on in vivo and in vitro models of neurodegenerative disease was also tested. The neuroprotective effect of G79 in the in vitro models of PD, ALS and neuroinflammation was shown. Also, G79 showed beneficial effect in vivo in the animal models of both MS and glaucoma ameliorating the clinical score of the animals affected by EAE, and reducing cell death of RGC in glaucomatous eyes. The penetration through blood-brain-barrier (BBB) of the compounds of Formula III-V was also tested. According to the results, G79 shows better penetration through the BBB by active transport, explaining its better profile than G80 and G81. This form of transport guarantees a more specific delivery of the drug and permanence inside the brain, compared to the passive transport.

In conclusion, the results show that neurotrophin-like molecules can provide a good therapeutic strategy to overcome the problem of delivery of neurotrophins into the brain, preserving, and even enhancing, the beneficial effects of neurotrophins themselves for the treatment of neurodegenerative diseases.

The term "prodrug", as used herein, includes any compound derived from the compounds of any of Formulae I-V, for example, the ester, amide, phosphate, etc., which, upon being administered to an individual, is capable of providing the compounds of any of Formulae I-V or the pharmaceutically acceptable salt thereof, directly or indirectly, to said individual. Preferably, said derivative is a compound that increases the bioavailability of the compounds of any of Formulae I-V when administered to an individual or that promotes the release of the compounds of any of Formulae I-V in a biological compartment. The nature of said derivative is not critical, provided that it may be administered to an individual and that it provides the compounds of any of Formulae I-V in an individual's biological compartment. The preparation of said prodrug may be performed by conventional methods known by those skilled in the art. Conventional procedures for the selection and preparation of suitable prodrug derivatives are described in, for example, *Design of Prodrugs*, H. Bundgaard ed., Elsevier (1985). An example of prodrug of the compounds of any of Formulae I-V can be their encapsulation into liposomes. By this procedure, the peptoid is treated with the appropriate liposome precursor (combination of a phospholipid like lecithin, cholesterol and water) in order to be encapsulated. Depending upon the lipophilicity of the peptoid, the compound will be retained at the lipophilic part of the liposome or at the aqueous inner portion. Regarding the therapeutic polymer, the peptoid could be attached to the polymer by covalent bonds created after regioselective hydrolysis of the terminal carboxamide. This hydrolysis renders a free carboxylic acid that can be condensed with an amino or hydroxyl activated group of the polymer.

The term "pharmaceutically acceptable" means that a compound or combination of compounds is sufficiently compatible with the other ingredients of a formulation, and not deleterious to the patient up to those levels acceptable by the industry standards.

For therapeutic use, salts of the compounds of any of Formulae I-V are those wherein the counter-ion is pharmaceutically acceptable.

The term "salt" as mentioned herein is meant to comprise any stable salts, which the compounds of any of Formulae I-V are able to form. Preferred are the pharmaceutically acceptable salts. Salts that are not pharmaceutically acceptable are also embraced in the scope of the present invention, since they refer to intermediates that may be useful in the preparation of compounds with pharmacological activity.

The salts can conveniently be obtained by treating the base form of the compounds of any of Formulae I-V with such appropriate acids as inorganic acids such as hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

The pharmaceutically acceptable salts can be obtained by treating the base form of the compounds of any of Formulae I-V with such appropriate pharmaceutically acceptable acids like inorganic acids, for example, including hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propane-tricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and the like acids.

Conversely the salt form can be converted by treatment with alkali into the free base form.

The term "pharmaceutical composition" means for the purpose of the present invention any composition which comprises as an active compound, to which is attributed, fully or in part, the therapeutic (e.g. pharmaceutical) effect, at least one of the compounds of the invention or combinations thereof and that may optionally further comprise at least one pharmaceutically acceptable non-active ingredient, as an excipient, carrier or so.

The term "preventing" refers to keep from happening, existing, or alternatively delaying the onset or recurrence of a disease, disorder, or condition to which such term applies, or of one or more symptoms associated with a disease, disorder, or condition. The term "prevention" refers to the act of preventing, as "preventing" is defined immediately above.

The term "treating", as used herein, refers to reversing, alleviating, or inhibiting the progress of the disorder or condition to which such term applies, or one or more symptoms of such disorders or condition. The term "treatment" refers to the act of treating, as "treating" is defined immediately above.

The term "subject" means animals, in particular mammals such as dogs, cats, cows, horses, sheep, geese, and humans. Particularly preferred subjects are mammals, including humans of both sexes.

An "effective amount" of the compounds of any of Formulae I-V and pharmaceutically acceptable salts or prodrugs thereof, may be in the range from 0.01 mg to 50 g per day, from 0.02 mg to 40 g per day, from 0.05 mg to 30 g per day, from 0.1 mg to 20 g per day, from 0.2 mg to 10 g per day, from 0.5 mg to 5 g per day, from 1 mg to 3 g per day, from 2 mg to 2 g per day, from 5 mg to 1.5 g per day, from 10 mg to 1 g per day, from 10 mg to 500 mg per day.

Nerve cells include those cells from any region of the brain, spinal cord, optic nerve, retina, and peripheral ganglia. Neurons include those in embryonic, fetal, or adult neural tissue, including tissue from the hippocampus, cerebellum, spinal cord, cortex (e.g., motor or somatosensory cortex), striatum, basal forebrain (cholinergic neurons), ventral mesencephalon (cells of the substantia nigra), and the locus ceruleus (neuroadrenaline cells of the central nervous system).

The invention also covers the use of the compounds of any of Formulae I-V, and pharmaceutically acceptable salts and prodrugs thereof, as active ingredients in the manufacture of medicaments for the prevention or treatment of nerve cell death or damage. In other words, the present invention relates to the compounds of any of Formulae I-V, and pharmaceutically acceptable salts and prodrugs thereof, for use in the prevention or treatment of nerve cell death or damage. Similarly, the present invention relates to a method of neuroprotection comprising administering to a subject in need thereof an effective amount of a compound of any of Formulae I-V, or a pharmaceutically acceptable salt or a prodrug thereof.

In one embodiment of the present invention, compounds of any of Formulae I-V, and pharmaceutically acceptable salts and prodrugs thereof, may be used for the prevention or treatment of one or more, preferably two or more, pathological or harmful conditions related to nerve cell death or damage selected from, but not being limited to, chemical substances such as oxidative stress conditions, toxic substances, infectious organisms, radiation, traumatic injury, hypoxia, ischemia, abnormal misfolded proteins, excitotoxins, free radicals, endoplasmic reticulum stressors, mitochondrial stressors including but not limited to inhibitors of the electron transport chain, Golgi apparatus antagonists, axonal damage or loss, demyelination, inflammation, pathological neuronal burst (seizures). Also preferably, the uses and methods of the present invention are directed to preventing or treating nerve cell death or damage, regardless of cause.

The terms "neuroprotection", "neuroprotective", or "neuroprotective effect" refer to the ability to prevent or reduce death or damage to nerve cells, including neurons and glia, or rescuing, resuscitating or reviving nerve cells, e.g., following in pathological or harmful conditions to the brain, central nervous system or peripheral nervous system. Thus, this neuroprotective effect comprises the conferred ability of neuronal cells to maintain or recover their neuronal functions. It stabilizes the cell membrane of a neuronal cell or helps in the normalization of neuronal cell functions. It prevents the loss of viability or functions of neuronal cells. It comprises the inhibition of progressive deterioration of neurons that leads to cell death. It refers to any detectable protection of neurons from stress. Neuroprotection includes the regeneration of nerve cells, i.e. the re-growth of a population of nerve cells after disease or trauma.

Currently the majority of the neurological and psychiatric diseases lacks specific treatments aimed to stop or ameliorate the course of the disease, which are called "disease modifying drugs". This contrasts with the symptomatic therapies which are common for such diseases but do not change the course of the disease. A neuroprotective drug is a Disease Modifying Drug (DMD) for the treatment of brain diseases.

As such, in one embodiment, the present invention relates to the use of the compounds of any of Formulae I-V, and pharmaceutically acceptable salts and prodrugs thereof, as active ingredients in the manufacture of a medicament for the regeneration of nerve cells. In other words, the present invention relates to the compounds of any of Formulae I-V, and pharmaceutically acceptable salts and prodrugs thereof, for use for the regeneration of nerve cells. Similarly, the present invention relates to a method of regenerating nerve cells, comprising administering to a subject in need thereof an effective amount of a compound of any of Formulae I-V, or a pharmaceutically acceptable salt or prodrug thereof.

Neuroprotection may be determined directly by, for example, measuring the delay or prevention of neuronal death, such as, for example, by a reduction in the number of apoptotic neurons in cerebrocortical cultures following a stress. Neuroprotection may also be determined directly by, for example, measuring the severity or extent of damage to, or functional loss by, a tissue or organ of the nervous system following such a stress, such as, for example, by measuring a decrease in the size of brain infarcts after occlusion of the middle cerebral artery (MCAO) or reperfusion injury. Also, neuroprotection can be identified by magnetic resonance imaging (measuring brain volume, tractography, levels of N-acetyl-aspartate by spectroscopy, optic coherent tomography). Alternatively, neuroprotection may be determined indirectly by detecting the activation of one or more biological mechanisms for protecting neurons, including, but not limited to, detecting activation of the Keap1/Nrf2 pathway or induction of one or more phase 2 enzymes, including but not limited to hemeoxygenase-1 (HO-1). Methods of detecting and measuring neuronal protection are provided in the Examples below, and other such methods are known in the art.

The various uses and methods employing the compounds of any of Formulae I-V, and pharmaceutically salts and/or prodrugs thereof, in the present invention comprise acute administration, i.e. occurring within several minutes to about several hours from injury, or chronic administration, suitable for chronic neurological or psychiatric diseases.

In one embodiment of the present invention, in the various uses and methods of neuroprotection or of prevention or treatment of nerve cell death or damage, the compounds of any of Formulae I-V, and pharmaceutically acceptable salts and prodrugs thereof, are administered to a subject with a neurological or psychiatric disease.

Neurological diseases are those disorders of the central and peripheral nervous system, including disorders of the brain, spinal cord, cranial nerves, peripheral nerves, nerve roots, autonomic nervous system, neuromuscular junction, and muscle.

Diseases of the central and peripheral nervous system, which may be subject of prevention and/or treatment according to present invention include, without being limited to, as knowledge in clinical manifestations advances, Absence of the Septum Pellucidum, Acid Lipase Disease, Acid Maltase Deficiency, Acquired Epileptiform Aphasia, Acute Disseminated Encephalomyelitis, Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications. Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder (ADHD), Autism, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain infarction, Brain ischemia, Brain Injury, Brown-Sequard Syndrome, Bulbospinal Muscular Atrophy, CADASIL, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysm, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome, Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome. COFS, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy, familial infantile, with intracranial calcification and chronic cerebrospinal fluid lymphocytosis; Cree encephalitis; Pseudo-Torch syndrome; Pseudotoxoplasmosis syndrome, Encephalotrigeminal Angiomatosis, Epilepsy, Epileptic Hemiplegia, Erb-Duchenne and Dejerine-Klumpke Palsies, Erb's Palsy, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gangliosidoses, Gaucher's Disease, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia. Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly. Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mild Cognitive Impairment, Mini-Strokes, Mitochondrial Myopathies, Moebius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis. Myoclonic Encephalopathy of Infants, Myoclonus, Myopathy, Myopathy—Congenital, Myopathy—Thyrotoxic, Myotonia, Myotonia Congenita, Narcolepsy. Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Ohtahara Syndrome, Olivopontocerebellar Atrophy. Opsoclonus Myoclonus, Orthostatic Hypotension, O'Sullivan-McLeod Syndrome, Overuse Syndrome, Pain—Chronic, Pantothenate Kinase-Associated Neurodegeneration, Paraneoplastic Syndromes, Parcsthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudotumor Cerebri, Ramsay Hunt Syndrome I (formerly known as dyssynergia cerebellaris myoclonica, dyssynergia cerebellaris progressiva, dentatorubral degeneration, or Ramsey Hunt cerebellar syndrome), Ramsay Hunt Syndrome II (formerly known as herpes zoster oticus), Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, Wolman's Disease, X-Linked Spinal and Bulbar Muscular Atrophy, Zellweger Syndrome, optic neuritis, Chronic fatigue syndrome, fibromialgia, psychiatric diseases such as mood disorders, major depression, bipolar syndrome, psycosis, eschizophrenia, obsessive-compulsive-syndrome, etc., Toxic or drug abuse diseases such as alcoholism and drug abuse, Encephalopathy like hepatic encephalopathy.

Psychiatric disorders, which may be the subject of prevention and/or treatment according to the present invention include those listed by the Diagnostic and Statistical Manual of Mental Disorders, Fourth Edition (DSM-IV) published by the American Psychiatric Association, and covers all mental health disorders for both children and adults. In particular, psychiatric disorders include a disorder selected from Acute Stress Disorder; Adjustment Disorder Unspecified; Adjustment Disorder with Anxiety; Adjustment Disorder with Depressed Mood; Adjustment Disorder with Disturbance of Conduct; Adjustment Disorder with Mixed Anxiety and Depressed Mood; Adjustment Disorder with Mixed Disturbance of Emotions and Conduct; Agoraphobia without History of Panic Disorder; Anorexia Nervosa; Antisocial Personality Disorder; Anxiety Disorder Due to Medical Condition; Anxiety Disorder, NOS; Avoidant Personality Disorder; Bipolar Disorder NOS; Bipolar I Disorder. Most Recent Episode Depressed, In Full Remission; Bipolar I Disorder, Most Recent Episode Depressed. In Partial Remission; Bipolar I Disorder, Most Recent Episode Depressed, Mild; Bipolar I Disorder, Most Recent Episode Depressed, Moderate; Bipolar I Disorder, Most Recent Episode Depressed, Severe With Psychotic Features; Bipolar I Disorder, Most Recent Episode Depressed, Severe Without Psychotic Features; Bipolar I Disorder, Most Recent Episode Depressed, Unspecified; Bipolar I Disorder, Most Recent Episode Manic, In Full Remission; Bipolar I Disorder, Most Recent Episode Manic, In Partial Remission; Bipolar I Disorder, Most Recent Episode Manic, Mild; Bipolar I Disorder, Most Recent Episode Manic, Moderate; Bipolar I Disorder, Most Recent Episode Manic, Severe With Psychotic Features; Bipolar I Disorder, Most Recent Episode Manic. Severe Without Psychotic Features; Bipolar I Disorder, Most Recent Episode Manic, Unspecified; Bipolar I Disorder, Most Recent Episode Mixed, In Full Remission; Bipolar I Disorder, Most Recent Episode Mixed, In Partial Remission; Bipolar I Disorder, Most Recent Episode Mixed, Mild; Bipolar I Disorder, Most Recent Episode Mixed, Moderate; Bipolar I Disorder, Most Recent Episode Mixed, Severe With Psychotic Features; Bipolar I Disorder, Most Recent Episode Mixed, Severe Without Psychotic Features; Bipolar I Disorder, Most Recent Episode Mixed, Unspecified; Bipolar I Disorder, Most Recent Episode Unspecified; Bipolar I Disorder, Most Recent Episode Hypomanic; Bipolar I Disorder, Single Manic Episode, In Full Remission; Bipolar I Disorder, Single Manic Episode, In Partial Remission; Bipolar I Disorder, Single Manic Episode, Mild; Bipolar I Disorder, Single Manic Episode, Moderate; Bipolar I Disorder, Single Manic Episode, Severe With Psychotic Features; Bipolar I Disorder, Single Manic Episode, Severe Without Psychotic Features; Bipolar I Disorder, Single Manic Episode, Unspecified; Bipolar II Disorder; Body Dysmorphic Disorder; Borderline Personality Disorder; Breathing-Related Sleep Disorder; Brief Psychotic Disorder; Bulimia Nervosa; Circadian Rhythm Sleep Disorder; Conversion Disorder; Cyclothymic Disorder; Delusional Disorder; Dependent Personality Disorder; Depersonalization Disorder; Depressive Disorder NOS; Dissociative Amnesia; Dissociative Disorder NOS; Dissociative Fugue; Dissociative Identity Disorder; Dyspareunia; Dyssomnia NOS; Dyssomnia Related to Another Disorder; Dysthymic Disorder; Eating Disorder NOS; Exhibitionism; Female Dyspareunia Due to Medical Condition; Female Hypoactive Sexual Desire Disorder Due to Medical Condition; Female Orgasmic Disorder; Female Sexual Arousal Disorder; Fetishism; Frotteurism; Gender Identity Disorder in Adolescents or Adults; Gender Identity Disorder in Children; Gender Identity Disorder NOS; Generalized Anxiety Disorder; Histrionic Personality Disorder; Hypoactive Sexual Desire Disorder; Hypochondriasis; Impulse-Control Disorder NOS; Insomnia Related to Another Disorder; Intermittent Explosive Disorder; Kleptomania; Major Depressive Disorder, Recurrent, In Full Remission; Major Depressive Disorder, Recurrent, In Partial Remission; Major Depressive Disorder, Recurrent, Mild; Major Depressive Disorder, Recurrent, Moderate; Major Depressive Disorder, Recurrent, Severe With Psychotic Features; Major Depressive Disorder, Recurrent, Severe Without Psychotic Features; Major Depressive Disorder, Recurrent, Unspecified; Major Depressive Disorder, Single Episode, In Full Remission; Major Depressive Disorder, Single Episode, In Partial Remission; Major Depressive Disorder, Single Episode, Mild; Major Depressive Disorder, Single Episode, Moderate; Major Depressive Disorder, Single Episode, Severe With Psychotic Features; Major Depressive Disorder, Single Episode, Severe Without Psychotic Features; Major Depressive Disorder, Single Episode, Unspecified; Male Dyspareunia Due to Medical Condition; Male Erectile Disorder; Male Erectile Disorder Due to Medical Condition; Male Hypoactive Sexual Desire Disorder Due to Medical Condition; Male Orgasmic Disorder; Mood Disorder Due to Medical Condition; Narcissistic Personality Disorder; Narcolepsy; Nightmare Disorder; Obsessive Compulsive Disorder; Obsessive-Compulsive Personality Disorder; Other Female Sexual Dysfunction Due to Medical Condition; Other Male Sexual Dysfunction Due to Medical Condition Pain Disorder Associated with both Psychological Factors and Medical Conditions; Pain Disorder Associated with Psychological Features; Panic Disorder with Agoraphobia; Panic Disorder without Agoraphobia; Paranoid Personality Disorder; Paraphilia, NOS; Parasomnia NOS; Pathological Gambling; Pedophilia; Personality Disorder NOS; Posttraumatic Stress Disorder; Premature Ejaculation; Primary Hypersomnia; Primary Insomnia; Psychotic Disorder Due to Medical Condition, with Delusions; Psychotic Disorder Due to Medical Condition, with Hallucinations; Psychotic Disorder, NOS; Pyromania; Schizoaffective Disorder; Schizoid Personality Disorder; Schizophrenia, Catatonic Type; Schizophrenia, Disorganized Type; Schizophrenia, Paranoid Type; Schizophrenia, Residual Type; Schizophrenia, Undifferentiated Type; Schizophreniform Disorder; Schizotypal Personality Disorder; Sexual Aversion Disorder; Sexual Disorder NOS; Sexual Dysfunction NOS; Sexual Masochism; Sexual Sadism; Shared Psychotic Disorder; Sleep Disorder Due to A Medical Condition, Hypersomnia Type; Sleep Disorder Due to A Medical Condition, Insomnia Type; Sleep Disorder Due to A Medical Condition, Mixed Type; Sleep Disorder Due to A Medical Condition, Parasomnia Type; Sleep Terror Disorder; Sleepwalking Disorder; Social Phobia; Somatization Disorder; Somatoform Disorder NOS; Specific Phobia; Transvestic Fetishism; Trichotillomania; Undifferentiated Somatoform Disorder; Vaginismus; and Voyeurism.

Preferably, the compounds of any of Formulae I-V, and pharmaceutically acceptable salts and prodrugs thereof, can be used in the treatment of diseases wherein NGF or other neurotrophins have been proven effective in the state of the art, either in vivo or in vitro, due to their improving effects on cell differentiation and cell survival, through either TrkA, TrkB and/or p75 pathways. Therefore, the compounds covered in the present invention can be used in the treatment of neurological diseases selected among: neurodegenerative disorders, such as amyotrophic lateral sclerosis (ALS), Parkinson's disease, Alzheimer's disease, Friedreich's ataxia, Huntington's disease, Dementia with Lewy bodies, spinal muscular atrophy; nerve inflammation, such as multiple sclerosis and neuromyelitis optica; major depressive disorder; schizophrenia; glaucoma; or peripheral neuropathies, such as diabetic or AIDS neuropathy. Moreover, the compounds of the invention can also be indicated for treatment of cancer, by modulating NGF cell differentiation activity and stopping cell proliferation. Among the cancer types in which NGF has been proven effective in the state of the art, either in vivo or in vitro, due to improving effects on cell differentiation and cell survival, through either TrkA and/or p75 pathways, the following may be cited: glioblastoma, astrocytoma, medulloblastoma, neurinoma, neuroblastoma, meningioma, colon cancer, pancreatic cancer, breast cancer, prostate cancer, leukemia, acute lymphocytic leukemia, osteosarcoma, hepatocellular carcinoma, ovarian carcinoma, lung adenocarcinoma or esophagic carcinoma.

In one embodiment of the present invention, in the various uses and methods of neuroprotection or of prevention or treatment of nerve cell death or damage, the compounds of any of Formulae I-V, and pharmaceutically acceptable salts and prodrugs thereof, are administered to a healthy subject, preferably a healthy subject older than 18 years old, more preferably a healthy subject older than 45 years old, even more preferably a healthy subject older than 55, 60, 65, 70, 75, 80, 85, 90, 95, or 100 years old.

The term "healthy subject" is meant to comprise its plain meaning as well as those subjects that may suffer from one or more pathological conditions other than a neurological or psychiatric disease.

The neuroprotective properties of the compounds of any of Formulae I-V, and pharmaceutically salts and prodrugs thereof, have as a consequence the partial or full prevention or treatment of the various disorders in the nervous system functions caused by the neuronal cell death or damage. Therefore, the present invention further relates to the use of the compounds of any of Formulae I-V, and pharmaceutically acceptable salts and prodrugs thereof, as active ingredients in the manufacture of a medicament for the prevention or treatment of a neurological or psychiatric disease. In other words, the present invention also relates to the compounds of any of Formulae I-V, and pharmaceutically acceptable salts and prodrugs thereof, for use in the prevention or treatment of a neurological or psychiatric disease. Similarly, the present invention also relates to a method of prevention or treatment of a neurological or psychiatric disease comprising administering to a subject in need thereof an effective amount of the compound of any of Formulae I-V, or a pharmaceutically acceptable salt or prodrug thereof. The neurological or psychiatric disease may be any one from those listed above.

Preferably, the neurological or psychiatric disease is selected from neurodegenerative disorders, inflammation and certain types of cancers, multiple sclerosis, neuromyelitis optica, amyotrophic lateral sclerosis (ALS), Parkinson's disease. Alzheimer's disease, Friedreich's ataxia, Huntington's disease, Dementia with Lewy bodies, spinal muscular atrophy, major depressive disorder, schizophrenia, glaucoma or peripheral neuropathies (diabetic or AIDS neuropathy).

Another goal of present invention is the use of the compounds of any of Formulae I-V, and pharmaceutically acceptable salts and prodrugs thereof, as neuroenhancing drugs or the use for manufacturing neuroenhancing drugs.

Neuroenhancing drugs include those that improve learning and memory, attention, mood, communicative skills and sexual performance. Examples of neuroenhancing drugs are those that target long-term synaptic potentiation (LTP) or long-term depression (LTD), modulation of calcium channels, or the cAMP response element-binding (CREB) protein. cAMP is the acronym for cyclic adenosine monophosphate. Particular examples of neuroenhancing drugs are phosphodiesterase inhibitors like rolipram; donepezil; agonists of the NMDA glutamate receptor like D-cycloserine; ampakines; modafinil; methylphenidate.

A pharmaceutical composition of the present invention can be administered by any means that achieves its intended purpose. For example, the administration can be oral, parenteral, subcutaneous, intravenous, instramuscular, intraperinoneal, transdermal, intranasal, transmucosal, rectal, or buccal route. In one embodiment, the pharmaceutical composition is administered orally.

The compounds of any of Formulae I-V, and pharmaceutically acceptable salts and prodrugs thereof, may be formulated into various pharmaceutical forms for administration purposes. As appropriate compositions there may be cited all compositions usually employed for systemically administering drugs, for example any solid (e.g. tablets, capsules, granules, etc.) or liquid composition (e.g. solutions, suspensions, emulsions, etc). To prepare the pharmaceutical compositions of the compounds of any of Formulae I-V, an effective amount of the compound of any of Formulae I-V, optionally in a salt form or a prodrug, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, intrathecal, intravenous or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier usually comprises sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent or a suitable wetting agent, or both, optionally combined with suitable additives of any nature in minor proportions, which additives do not introduce a significant deleterious effect on the skin. A review of the different pharmaceutical forms for drug administration and their preparation may be found in the book "Tratado de Farmacia Galénica", de C. Faulí i Trillo, 10th Edition, 1993, Luzán 5, S.A. de Ediciones.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compositions in accordance with this invention, including unit dosage forms, may contain the active ingredient in an amount that is in the range of about 0.1% to 70%, or about 0.5% to 50%, or about 1% to 25%, or about 5% to 20%, the remainder comprising the carrier, wherein the foregoing percentages are w/w versus the total weight of the composition or dosage form.

The dose of the compound of any of Formulae I-V, its pharmaceutically acceptable salt or prodrug thereof, to be administered depends on the individual case and, as customary, is to be adapted to the conditions of the individual case for an optimum effect. Thus it depends, of course, on the frequency of administration and on the potency and duration of action of the compound employed in each case for therapy or prophylaxis, but also on the nature and severity of the disease and symptoms, and on the sex, age, weight co-medication and individual responsiveness of the subject to be treated and on whether the therapy is acute or prophylactic. Doses may be adapted in function of weight and for pediatric applications. Daily doses may be administered q.d. or in multiple quantities such as b.i.d., t.i.d. or q.i.d.

Synthesis of Compounds

The compounds of the present invention can be prepared using methods known to those skilled in the art in view of this disclosure. For example, compounds of the present invention can be prepared as described in Masip, et al., 2005.

Testing of Compounds

In addition to the tests described in the Examples, the compounds of the present invention can be tested for Alzheimer disease in vitro model as follows: The human neuroblastoma cell line SH-SY5Y is used to study the neuroprotective effect of the tested compound in Alzheimer disease. The cells are pre-treated for 3 hours with the tested compound at different concentrations (20 ng/ml, 100 ng/ml, 2 µg/ml, 20 µg/ml and 50 µg/ml) with the tested compound (100 ng/ml). Then Amiloid beta fibrils (100 µM) is added and incubated for 24 hrs. The number of surviving cells is determined the day after by 3-(4,5-dimethylthiazol-2-yl)-2, 5-diphenyltetrazolium bromide (MTT) assay.

Induction of TrkA, IκBα and SAPK/JNK phosphorylation by the compounds of the present invention can be tested as follows. Activation of TrkA is the first event in the signalling cascade leading to differentiation and survival of NGF responsive neurons and PC12 cells (Greene and Tischler, 1976; Chao, 2003; Huang and Reichardt, 2003). To evaluate whether the neurotrophic activity of NGF-like peptoids is mediated by the interaction with TrkA receptor, their capacity to induce TrkA phosphorylation in PC12 cells can be analyzed. The activity of peptoids can be tested in the range of concentrations that were effective on PC12 cells differentiation.

Western Blot Analysis.

Subconfluent cells are grown overnight in medium containing 2% FBS and 1% HS and stimulated with 100 ng/ml NGF or the NGF-like small chemicals for the indicated time points. Cells are then washed with cold phosphate-buffered saline (PBS) and briefly sonicated in SDS sample buffer (containing β-mercaptoethanol and 2 mM PMSF). Lysates (200 µg of total proteins) are separated on SDS-PAGE, and transferred to nitrocellulose (Whatman, Dassel, Germany). After blocking with 5% nonfat milk in TBST buffer (10 mM Tris pH 7.5; 150 mM NaCl/0.2% Tween 20), blots are probed overnight at 4° C. with anti-p-TrkA (Tyr 490) antibody (1:1000), anti TrkA antibody (1:1000), anti-p-IκBα (Ser 32/36)(5A5) mouse antibody (¹⁄₁₀₀₀), anti IκBα (L35A5) mouse antibody (1:1000), anti-p-SAPK/JNK (Thr183/Tyr185) antibody (1:1000) or anti-SAPK/JNK antibody (¹⁄₁₀₀₀)(all of them from Cell Signaling), followed by incubation with HRP-conjugated IgG (Jackson ImmunoResearch) for 1 h at room temperature (RT). Detection of phosphorylated species is performed by using the enhanced chemiluminescence (ECL) system (GE Healthcare Bio-Sciences, Piscataway, N.J.).

To investigate whether the compounds of the present invention activate p75, the activation of the NF-κB pathway (Bonizzi G, Karin M. 2004) and the SAPK/JNK pathway (cell death) in PC12 and RN22 cell lines can be analyzed. RN22 cells express high levels of the p75 receptor message and protein, whereas TrkA expression is undetectable (Gentry et al., 2000). NF-κB is functionally active as a transcriptional regulator in a dimeric form consisting of homo- or heterodimers, the prototypic NF-κB dimmer consisting of the p65 and p50 subunits. The activation of NF-κB occurs primarily through the degradation of the IκB proteins, a family of inhibitory proteins bound to NF-κB dimers. In response to activating stimuli, the inhibitory proteins are phosphorylated, which targets them for ubiquitination and subsequent degradation. One member of the inhibitory family, IκBα, is degraded in response to the majority of the NF-κB activators (Ghosh et al., 1998). To examine NF-κB activation in response to NGF and the different selected peptoids, westerns blots of total cell extracts from RN22 and PC12 cells treated with NGF and the peptoids for varying times are probed with an antibody anti-phospho-IκBα.

In several neuronal systems, JNK activation has been causally linked with the induction of programmed cell death (Bhakar et al., 2003). In culture, NGF signalling through p75 led to activation of both NF-Kb and JNK, resulting ultimately in programmed cell death (Yoon et al., 1998). To examine the activity of JNK in RN22 cells western blots can be done with antibody anti-phospho-SAPK/JNK to assess activation of the pathway.

Effect of neurotrophin peptidomimetics (e.g., NGF-mimetic peptides) in encephalomyelitis autoimmune experimental (EAE) can be assessed as follows:

Animals, Experimental Autoimmune Encephalomyelitis Induction, and Treatment.

Trials are approved by the University of Barcelona Committee on Animal Care. Female C57BL/6 mice from Harlan (8-12 weeks old) are immunized subcutaneously in both hind pads with 300 µg of myelin oligodendrocyte glycoprotein (MOG) peptide 35-55 (Spikem, Firenze) emulsified with 50 µg of *Mycobacterium tuberculosis* (H37Ra strain; Difco, Detroit, Mich.) in incomplete Freund's adjuvant (IFA) as previously described (Palacios et al. 2007). Mice are intraperitoneally injected with Pertussis toxin (Sigma) (500 ng) at the time of immunization and 2 days later. Animals are weighted and inspected for clinical signs of disease on a daily basis by a blinded observer. Disease severity of EAE is assessed according to the following scale: 0=normal; 0.5=mild limp tail; 1=limp tail; 2=mild parapesis of the hind limbs, unsteady gait; 3=moderate parapesis, voluntary movements still possible; 4=paraplegia or tetraparesis; 5=moribund state. Data shown for the clinical studies are representative of two independent experiments performed with the indicated number of animals (Moreno et al., 2006).

The test compounds are prepared in water with 5% DMSO. Animals are treated with the test compound (25, 50 and 100 mg/kg) or placebo (water+5% DMSO) through daily intraperitoneal injection starting after immunization. At the end of the study, mice are anesthetized and perfused intracardially with 4% of paraformaldehyde in 0.1M phosphate buffer (pH 7.6). Brains, spinal cords and spleens are dissected and either fixed or frozen until use. Serum is obtained from all animals included in the study, and transaminases levels are measured.

In order to evaluate the effects of the neurotrophin peptidomimetics (e.g., the NGF-like peptoids) "in vivo", the effect of the neurotrophin peptidomimetics (e.g., the NGF-mimetic peptides) in the animal model of MS can be studied. C57BL/6 mice immunized with MOG35-55 peptide are treated daily with a test compound intraperitoneally from day 0 to day 25 at a different concentrations of the compound. Effect of the compounds of the present invention in CNS and peripheral inflammation can be tested as follows:

Real-Time Quantitative Polymerase Chain Reaction.

Brains and spinal cords from mice obtained at the time of death are homogenized in RNA lysis buffer. Total RNA is extracted using the RNeasy Mini Kit (Qiagen, Chatwworth, Calif.) isolation system, including DNase treatment using the RNase-Free DNase Set (Quiagen). Total RNA (35 µg) is reverse transcribed using the Reverse Transcription System (High Capacity cDNA Archive Kit; Applied Biosystems, Foster City, Calif.). The real time reaction is conducted at 25° C. for 10 minutes, followed by 37° C. for 2 hours, and finally stored at 4° C. Primers and target-specific fluorescence-labeled TaqMan probes can be purchased from Applied Biosystems (TaqMan Gene Expression assays). For example, the TaqMan Universal Master Mix (Applied biosystems) can be used. Amplification of complementary DNA is performed on a DNA Engine Opticon 2 Real-Time System (MJ Research, Watertown, Mass.) using 0.9 µM for each primer and 0.25 µM for the probe and 20 ng complementary DNA. The reaction conditions are an initial 2 minutes at 50° C., followed by 10 minutes at 95° C. and 40 cycles of 15 seconds at 95° C. and 1 minute at 60° C. Each sample is run in triplicate, and in each plate the target and the endogenous control are amplified in different wells. The expression of the gene tested is quantified relative to the level of the housekeeping gene 18rRNA (Palacios et al., 2008).

Immunohistochemistry.

Histological evaluation is done on paraformaldehyde-fixed, paraffin-embedded sections of brain and spinal cord. Sections 10 µm thick) are stained with hematoxylin and Luxol Fast Blue to assess inflammation and demyelination. Semiquantitative histological evaluation for inflammation and demyelination is conducted and scored blindly using the following scale: 0=normal; 1=1 to 3/section perivascular cuffs with minimal demyelination; 2=3 to 10 perivascular cuffs/section accompanied by moderate demyelination; 3=wide-spread perivascular cuffing, extensive demyelination with large confluent lesions (Villoslada et al., 2001).

Immunohistochemical procedures are performed on 10 µm paraffin-embedded sections of brain and spinal cord as described previously (Villoslada et al., 2001). Primary antibodies are added at concentrations of ¹⁄₁₀₀₀ for MCA500 (rat anti-mouse CD3 from Serotec) and ¹⁄₅₀₀ for MCA1107 (rat anti-mouse CD4 from Serotec). Specificity of the immunoreaction is determined by incubating sections without the primary antibodies or using the corresponding isotype controls which yielded no immunoreactivity.

Proliferation Assay.

Splenocytes from naïve, non immunized C57BL/6 mice are obtained for in vitro assessment of the effect of the test compound in cell proliferation. Splenocyte proliferation assay is performed as described previously (Martincz-Forero et al., 2008).

To assess the effect of the test compound in the peripheral immune response, the proliferative response against the immunizing antigen (MOG) in splenocytes of naïve animals and the cytokine profile in spleen cells from placebo and treated animals are evaluated. Gene expression of interleukin2 (IL2), Interferon γ (IFNγ), tumor necrosis factor α (TNFα), inducible nitric oxide synthase (iNOS) and interleukin 10 (IL10) can be investigated by quantitative reverse transcriptase PCR at the end of the experiment in splenocytes from placebo and treated animals.

Statistical Analysis.

Statistical analyses can be performed with the two-tailed Mann-Whitney U test for comparing EAE scores, chi 2 test for comparing disease incidence and Kaplan-Meier curves for differences in day of onset of EAE. p values less than 0.05 are considered to indicate a significant difference. The statistical evaluation is conducted using the SPSS 16.0 statistical program (SPSS, Chicago, Ill.).

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Design of NGF Agonists by Combinatorial Chemistry

General.

Solvents, amines and other reagents were purchased from commercial suppliers and used without further purification. Reactions carried out under microwave irradiation were conducted in a 100 mL round bottomed flask equipped with a Dimroth condenser. The flask was introduced in the monomode cavity of a CEM Model Discover apparatus. The NMR spectra were recorded on a Varian Inova 500 apparatus ($^1$H NMR, 500 MHz; $^{13}$C NMR, 125 MHz) and on a Unity 300 apparatus ($^1$H NMR, 300 MHz; $^{13}$C NMR, 75 MHz). When appropriate, the assignment of $^1$H and $^{13}$C NMR peaks for compounds were confirmed by gDQCOSY and gHSQC experiments. The occurrence of different conformers led to highly complex spectra; the absorptions given below are referred to the major conformer present in the sample. The RP-HPLC analyses were performed with a Hewlett Packard Series 1100 (UV detector 1315A) modular system using a reverse-phase Kromasil 100 C8 (25×0.46 cm, 5 μm) column, with $CH_3CN$-buffer ammonium formate (20 mM, pH=5.0) mixtures at 1 mL/min as mobile phase and monitoring at 220 nm. Semi-preparative RP-HPLC was performed with a Waters (Milford, Mass., U.S.A.) system. High resolution mass spectra (HRMS-FAB) were carried out at the IQAC—Instituto de Química Avanzada de Cataluña—(Spain).

Synthesis of Individual Peptoids.

The synthesis of individual peptoids G79, G80, and G81 for the in vitro and in vivo assays was carried out following the substructure procedure reported by the group of Zuckermann with some modifications (Zuckermann et al, 1992)

The synthesis was carried out on a 1% cross-linked polysterene resin bearing the Fluorenylmethoxycarbonyl (Fmoc)-protected Rink amide linker AM RAM (0.79 mmol/g, Rapp Polymer; Germany). A suspension of 4 g of resin in 50 mL DMF was placed in a 100 mL round bottomed flask provided with a magnetic stirrer. The suspension was stirred for 5 min at 20° C., the solvent was removed by filtration through a 60 mL polypropylene syringe provided with a polyethylene porous plaque. Then, resin was transferred again to the reaction flask.

1. Fmoc Deprotection.

A solution of 60 mL of 20% piperidine in DMF was added to the roundbottomed flask containing the resin. The mixture was allowed to react under microwave activation for 5 min at 60° C. and 150 W. The resin was drained on the 60 mL syringe and washed with 40 mL, DMF. The treatment was carried out in duplicate. Then, the resin was filtered and washed with DMF (3×40 mL), iPrOH (3×40 mL), and $CH_2Cl_2$ (3×40 mL). Finally, it was drained for 2 min and transferred to the reaction flask. The deprotection was monitored by using the TNBS test (red colour as positive).

2. First Acylation.

The resin was treated with a solution of 5 equivalents of bromoacetic acid (2.2 g, 15.8 mmol) and 5 equivalents of N,N-diisopropylcarbodiimide (2.5 mL, 15.8 mmol) in 50 mL of DMF. The acylation was conducted under microwave irradiation (5 min, 60° C., 150 W). Then, the resin was filtered using the syringe, and washed with 40 mL of DMF. The reaction was carried out in duplicate. Afterwards, the resin was filtered and washed with DMF (3×40 mL), iPrOH (3×40 mL), and $CH_2Cl_2$ (4×10 mL). Next, it was drained for 2 min and the absence of primary amine was evaluated by TNBS test.

3. First Amination Coupling.

A suspension of the acylated resin in 50 mL DMF was treated with the suitable primary amine according to the final compound: 5 equivalents (2.2 mL, 15.8 mmol) of 2.2 mL 1-(3-aminopropyl)-2-pyrrolidinone, or 5 equivalents (3.2 g, 15.8 mmol) of 4-(2-aminoethyl)benzenesulfonamide. The reaction was conducted under microwave irradiation (7 min, 80° C., 150 W). The reaction was carried out in duplicate, washing and draining the resin through the syringe between the treatments. Finally, the resin was drained for 2 min and transferred to the flask. The incorporation of the amine was confirmed by the chloranil test (green colour for secondary amines).

4. Second and Third Acylation Steps.

They were carried out similarly to the first acylation step. In this case, two acylation treatments were enough to complete the reaction.

5. Second and Third Amination Coupling Steps.

They were carried out similarly to the first amination step, by using the corresponding primary amines. Thus, 5 equivalents (1.8 ml, 15.8 mmol) of 2-methyl-1-propanamine were used for the second amination coupling. For the third amination, 5 equivalents (2.0 mL, 15.8 mmol) of 2-(2-fluorophenyl)ethanamine or 5 equivalents (2.0 mL, 15.8 mmol) of 2-(1-pyrrolidinyl)ethanamine were used as according to the composition of the corresponding peptoid.

6. Cleavage.

After draining the resin, it was divided into 4 aliquotes and each one was treated with 20 mL of the cleavage cocktail (60:40:2 (v/v/v) TFA/$CH_2Cl_2$/$H_2O$). The mixtures were stirred for 30 min at 20° C. and filtered through a 10 mL polypropylene syringes provided with a polyethylene porous plaque. The filtrates were collected in a 250 mL flask and solvents were removed under reduced pressure. Finally, the yellow oil residue that was obtained for the case of each peptoid was redissolved in $H_2O$/ACN mixture and lyophilized to give 1.25-1.80 g of the expected crude peptoid in purities higher than 85% by HPLC.

7. Purification and Chemical Characterization.

Compounds were purified by semipreparative HPLC using a Waters PrePack®-$C_{18}$ (47×300 mm, 15-20 μm,) column, eluting with $CH_3CN$/$H_2O$ mixtures containing 0.1% TFA as mobile phases, and a flow rate of at 60 mL/min. Final compounds were obtained in purities higher to 98% by HPLC. Quantities obtained were: 10.64 mg of G79 (99% purity; HPLC), 7.55 mg of G80 (99% purity; HPLC), and 12.68 mg of G81 (99% purity; HPLC).

[N-(2-(2'-Fluorophenyl)ethyl)glycyl]-[N-(2-methylpropyl) glycyl]-N-[3-(2'-oxopyrrolidinyl)propyl]glycinamide (G79). Chemical Formula: $C_2H_{38}FN_5O_4$; MW 491, 5987.

[N-(2-(2'-Fluorophenyl)ethyl)glycyl]-[N-(2-methylpropyl) glycyl]-N-[2-(4'-sulfamoylphenyl)ethyl]glycinamide (G80). Chemical Formula: $C_{26}H_{36}FN_5O_5S$; MW 549, 658.

[N-(2-(1-Pyrrolidinyl)ethyl)glycyl]-[N-(2-methylpropyl) glycyl]-N-[2-(4'-sulfamoylphenyl)ethyl]glycinamide (G81). Chemical Formula: $C_{24}H_{40}N_6O_5S$; MW 524, 6766.

Example 2

Dose Response Differentiation Assay in PC12 Cell Line

Cell Culture:

Stock of PC12 cultures were maintained in Ham's F12 medium supplemented with 2.5% fetal bovine serum (FBS), 15% of horse serum (HS) and 1% penicillin/streptomycin. The cell culture was maintained in 5% $CO_2$ at 37° C.

PC12 cell differentiation was assessed by treating the cells with all the test compounds (G79, G80, and G81) at different testing concentration (2-20-100 ng/ml and 2-20-50 μg/ml). The cells were first plated into collagen-coated 24-wells plates with 2.5% FBS in the medium to be de-differentiated. After 72 hrs, the test compounds were added and NGF (Sigma Aldrich; 100 ng/ml) as positive control of differentiation. The number of differentiated cells, with neurite processes greater than two cell bodies in length, is counted after 3 days of treatment. The cell count is done in three randomly selected fields with 100 cells.

Compounds G79, G80 and G81 induce the differentiation of PC12 cells (FIG. 1A-1D). The NGF positive control induce a differentiation of 16.1±1.9 cells in a field of 100 cells. G79 induces significant differentiation, compared to control PC12 untreated cells, in a dose dependent manner (2-20-100 ng/ml and 2-20 μg/ml). The best working concentration is 20 μg/ml (number of cells: 11.3±2.68). At 50 μg/ml the number of differentiated cells decreases.

Figure 1A:
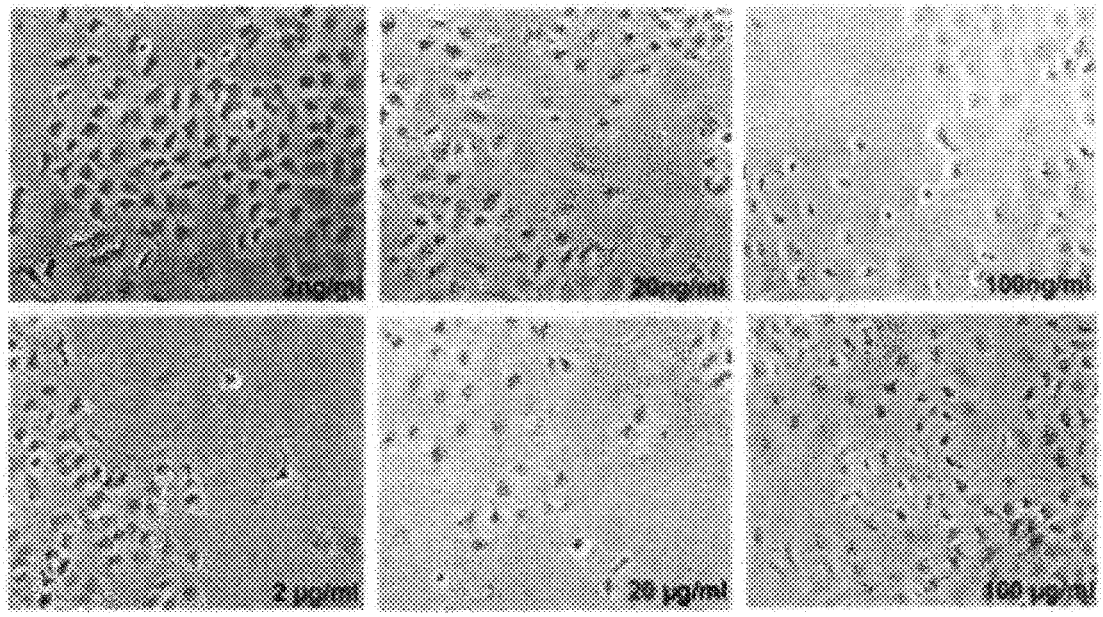
Figure 1B:
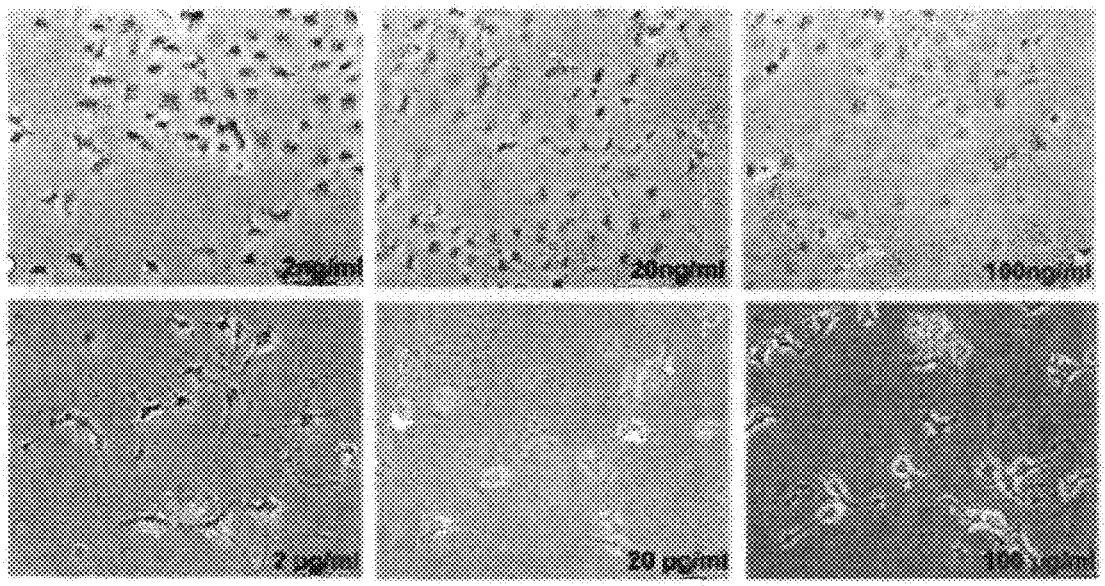
Figure 1C:
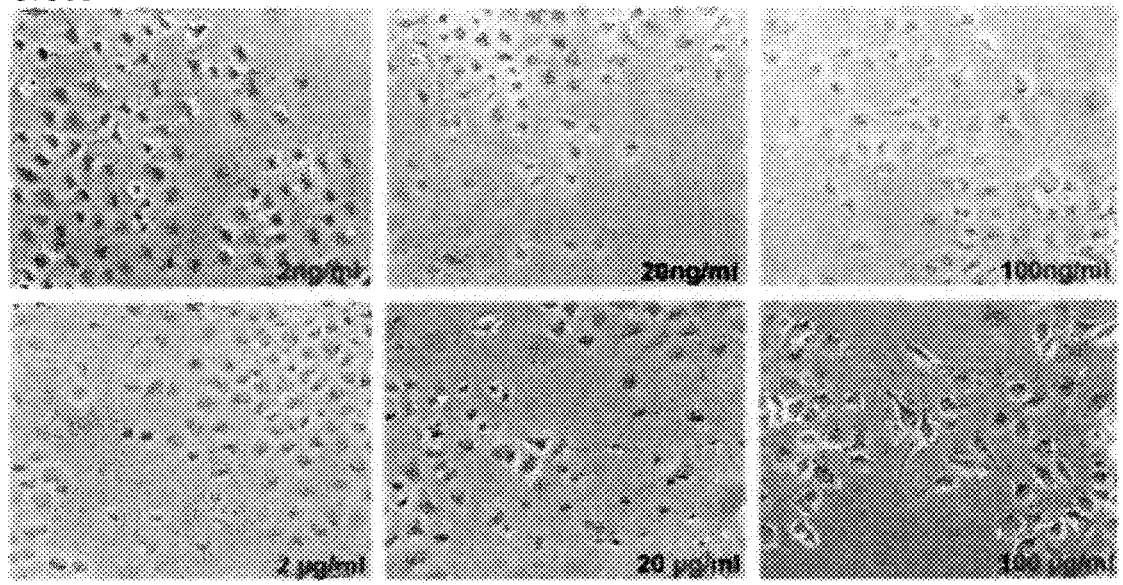
Figure 1D:
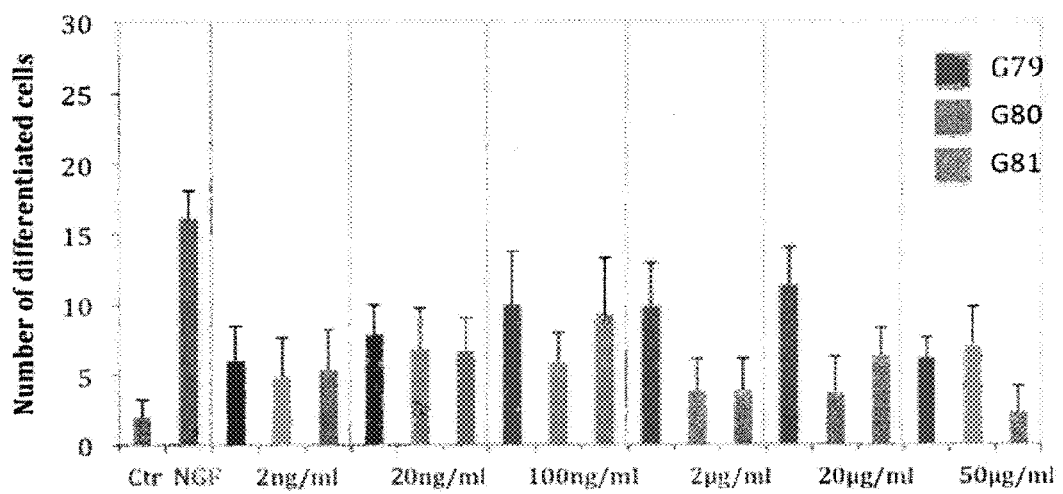
Figure 1E:
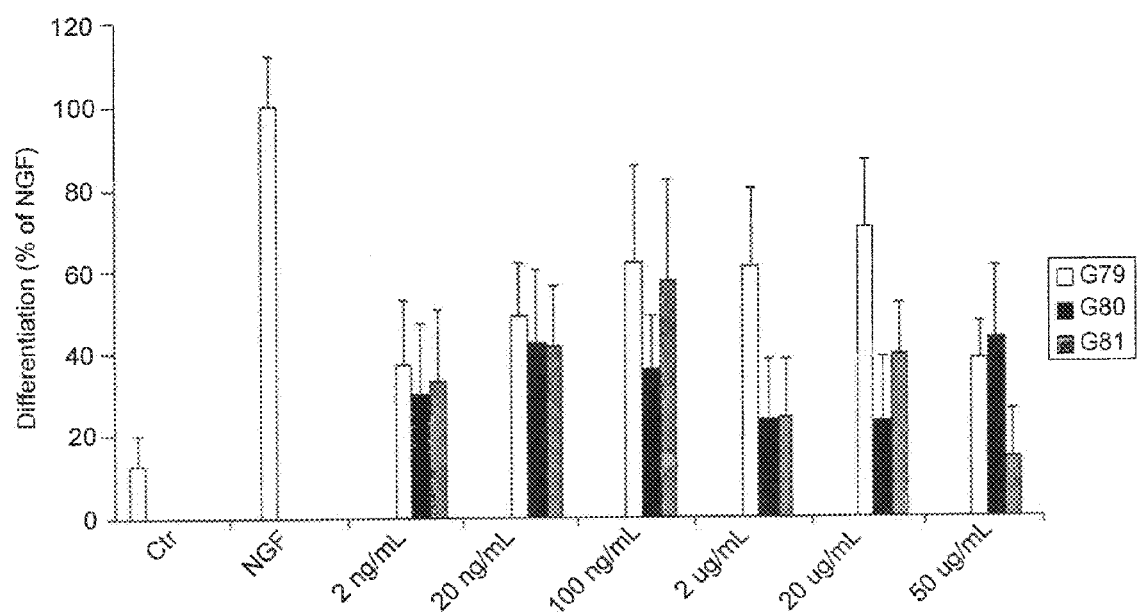

G80 induces good differentiation with very long neurites in PC12 cells. The best working concentration is 20 ng/ml. G81 induces significant differentiation, compared to control PC12 untreated cells, in a dose dependent manner until 100 ng/ml, that is the best working concentration (number of cells: 9.2±3.9). For higher concentration the number of differentiated cells decreases. The percentage of differentiated cells is calculated as relative to NGF induced differentiation (FIG. 1E).

Example 3

Survival Assays

G79, G80 and G81 Neurotrophin Peptidomimetics Promote Cell Survival.

Cell Culture.

The rat schwannome cell line RN22 was cultured in Dulbecco's modified Eagle's medium (DMEM) with 10% FBS and 1% penicillin/streptomycin. The cell culture was maintained in 5% $CO_2$ at 37° C.

RN22 were plated into 24-wells plates at the concentration of 30.000 cells/well in medium without serum. After 24 h, the test compounds G79, G80, and G81 were added at different concentrations (1-10-50 ng/ml and 1-10 μg/ml) and NGF was used as positive control of survival. The cells were so incubated for 2 hrs. Oxidative stress was induced with copper sulphate (CuSO4) at the final concentration of 150 μg/ml. After over-night incubation cell viability was determined by reading the absorbance after adding MTT (Sigma Aldrich).

Figure 2:
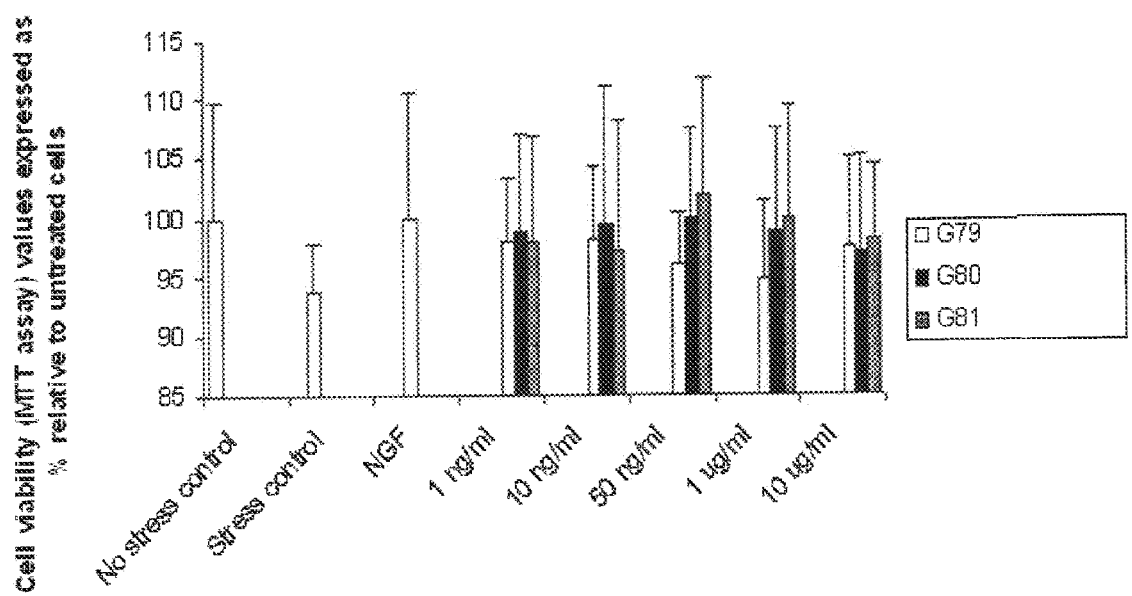

The percentage of surviving cells was calculated as relative to NGF induced differentiation (FIG. 2). G79 increased cell viability at all tested concentrations (1-10-50 ng/ml and 1-10 μg/ml) with a best working concentration at 10 ng/ml (98.11% of cell viability, as % relative to the no-stress control). G80 increased cell viability at all tested concentrations (1-10-50 ng/ml and 1-10 μg/ml) with a best working concentration at 50 ng/ml (99.86% cell viability, as % relative to the no-stress control). G81 increased cell viability at all tested concentrations (1-10-50 ng/ml and 1-10 μg/ml) with a best working concentration at 50 ng/ml (101.86% of cell viability, as % relative to the no-stress control).

Example 4

Secretagogue Activity Assay

G79, G80, and G81 do not Induce NGF Secretion.

To assess if the tested compounds, G79, G80, and G81, act as secretagogues, inducing neurotrophic activity through the synthesis of NGF, PC12 cells were plated into collagen-coated 24-wells plates with only 2.5% FBS and after 72 hrs the cells were treated with the tested compounds (each one at 100 ng/ml) together with antibody anti-NGF (1 μg/ml, AbCam). After three days of treatment, the differentiation was evaluated. The cell count was done in three randomly selected fields with 100 cells.

Figure 3A:
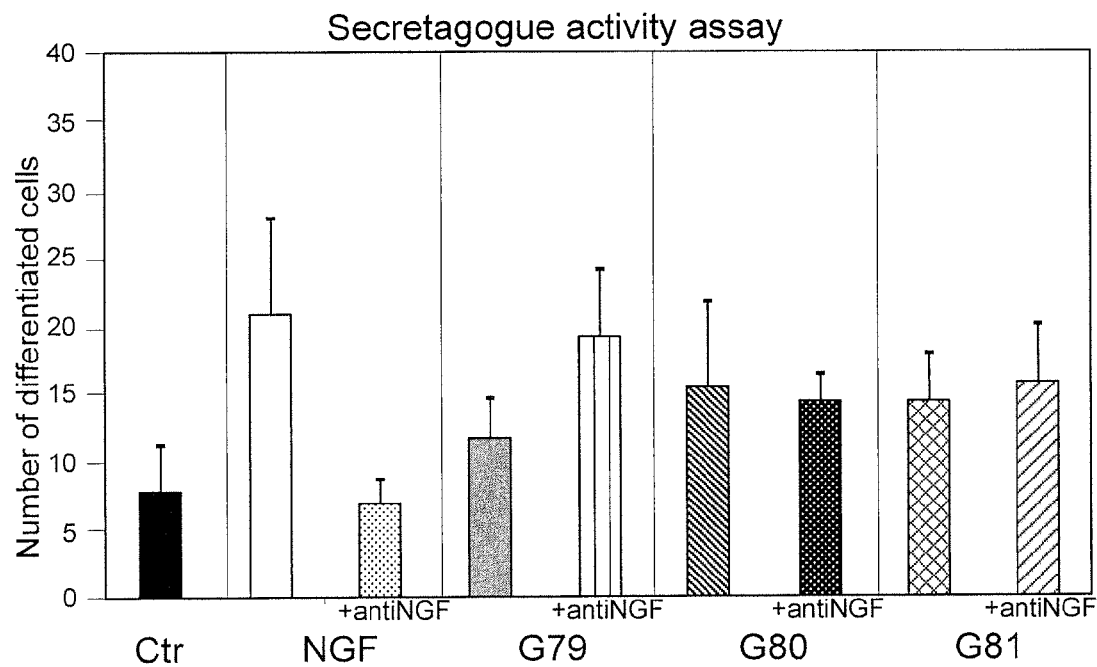

Treatment with G79, G80 or G81 together with antibody anti-NGF induce PC12 differentiation similarly to the differentiation induced by the tested compounds alone (FIG. 3A). Wile the number of differentiated cells by NGF is decreased by adding anti-NGF antibody (12.8±6.3 vs 20.7±7.1), the number of differentiated cells results to be quite similar comparing the treatment with the tested compounds alone with the treatment with this compounds and anti-NGF antibody. The G79/anti-NGF treatment obtained a number of differentiated cells for each field results to be 18.8±4.9 vs 11.5±2.8 for the treatment with only G79; for G80/anti-NGF is 14.1±1.8 vs 15.1±6.3 for the treatment with only G80; for G81/anti-NGF is 15.5±4.1 vs 14.1±3.3.

Figure 3B:
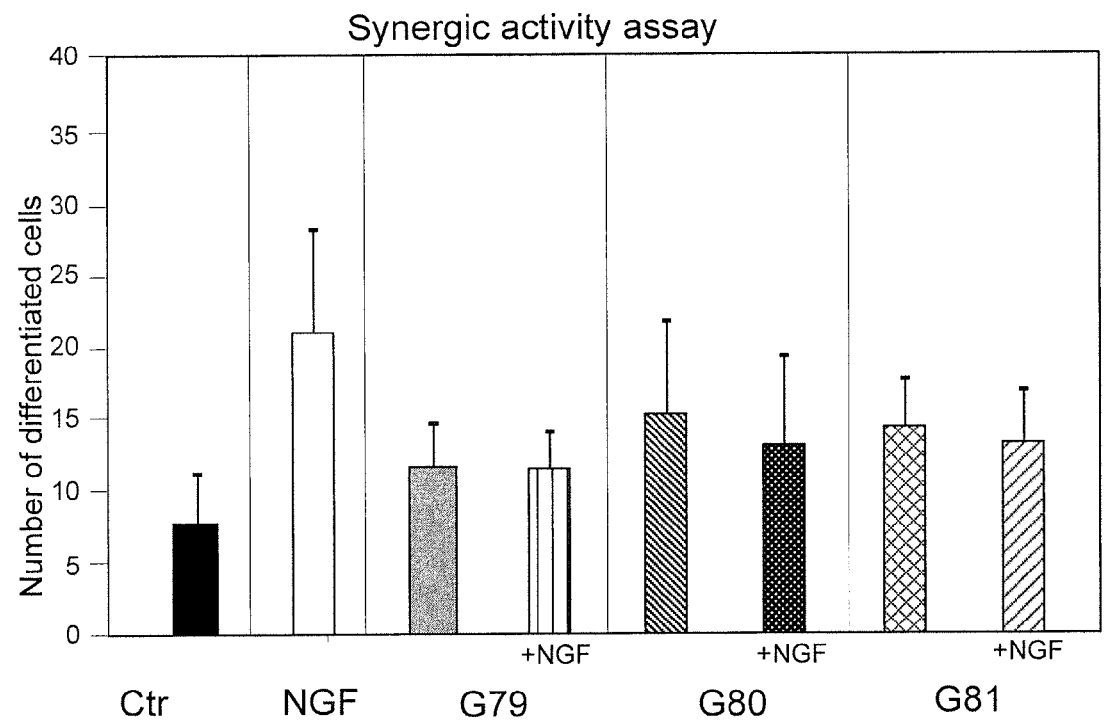
Figure 3C:
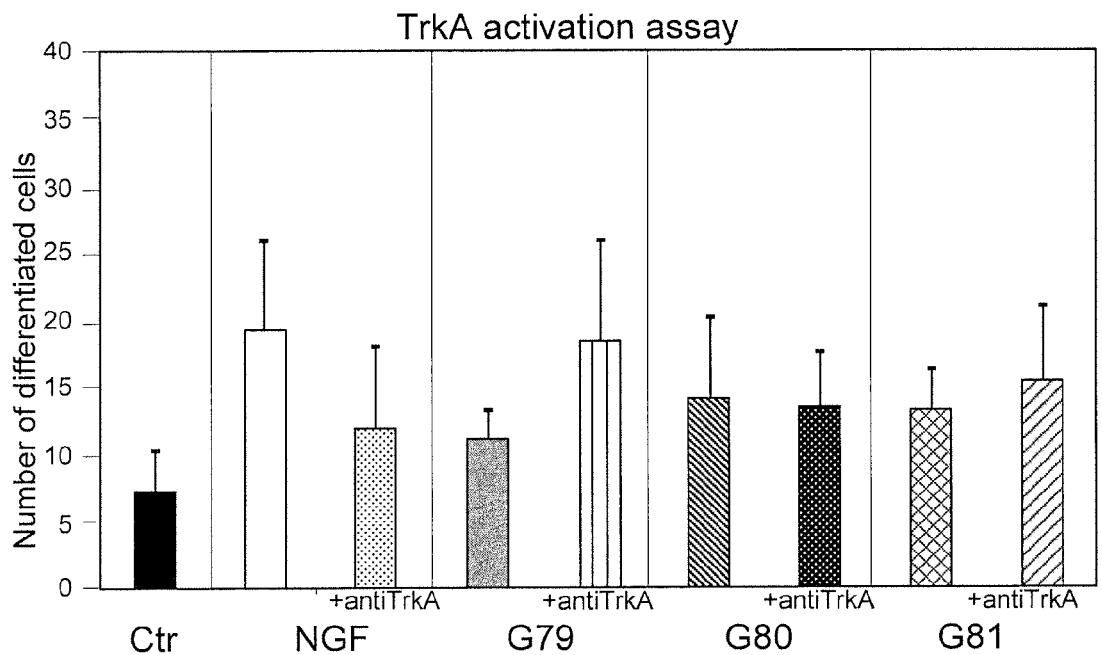
Figure 3D:
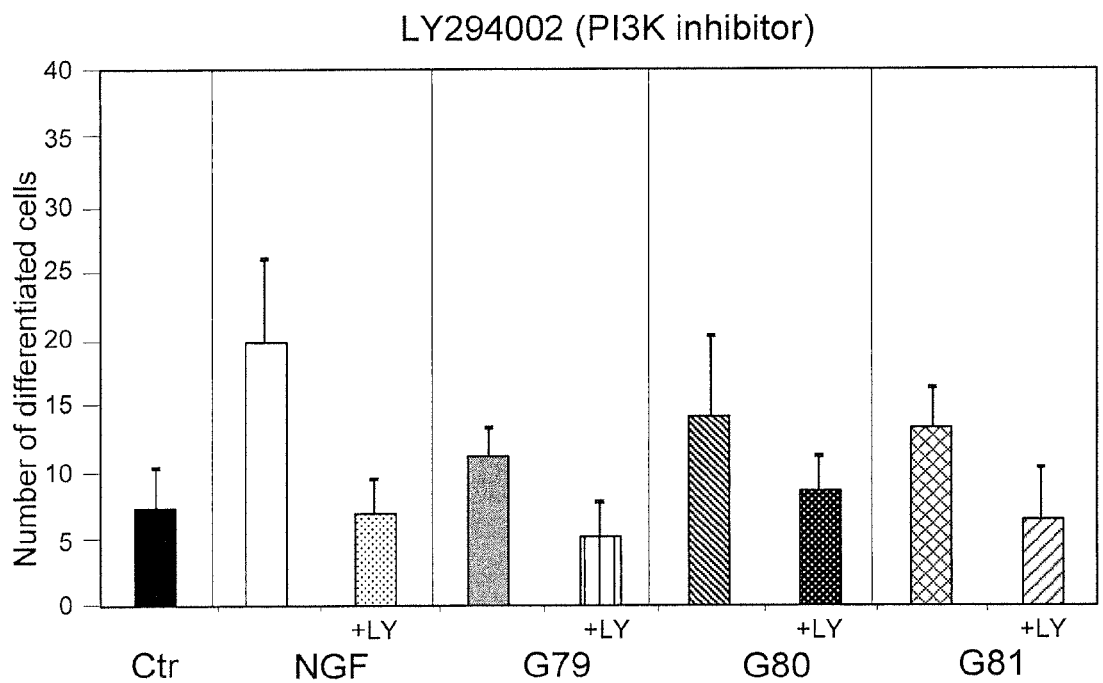
Figure 3E:
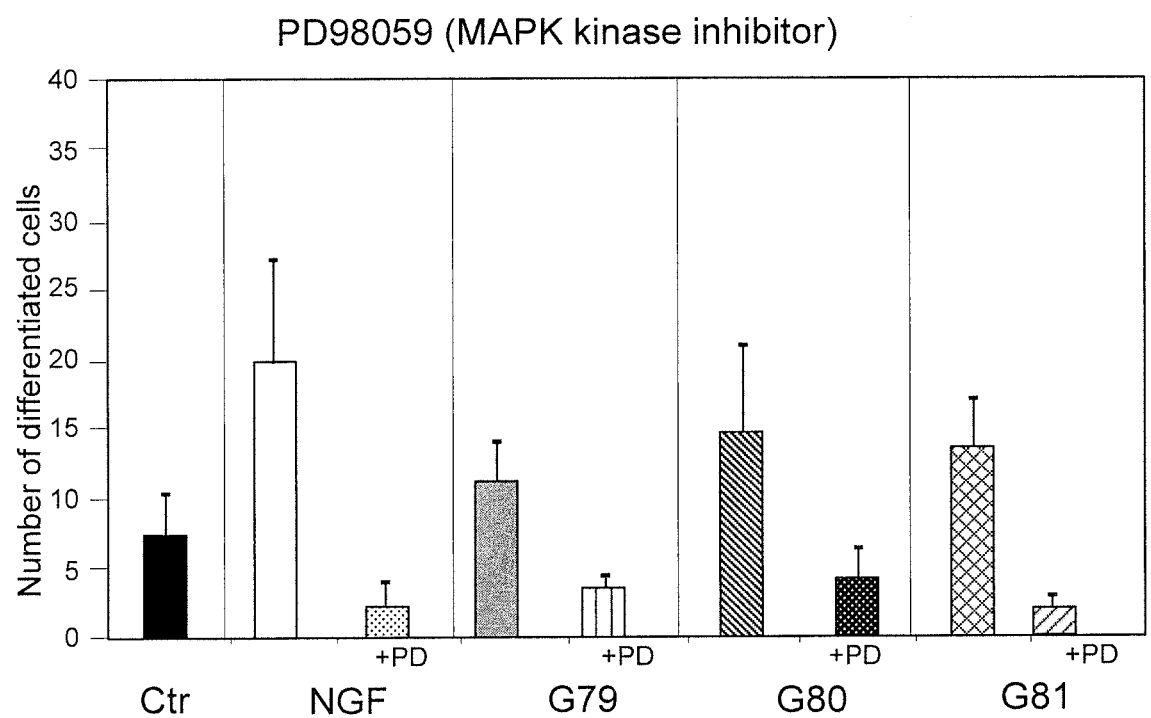
Figures 3F, 3G, 3H, 3I, 3J:
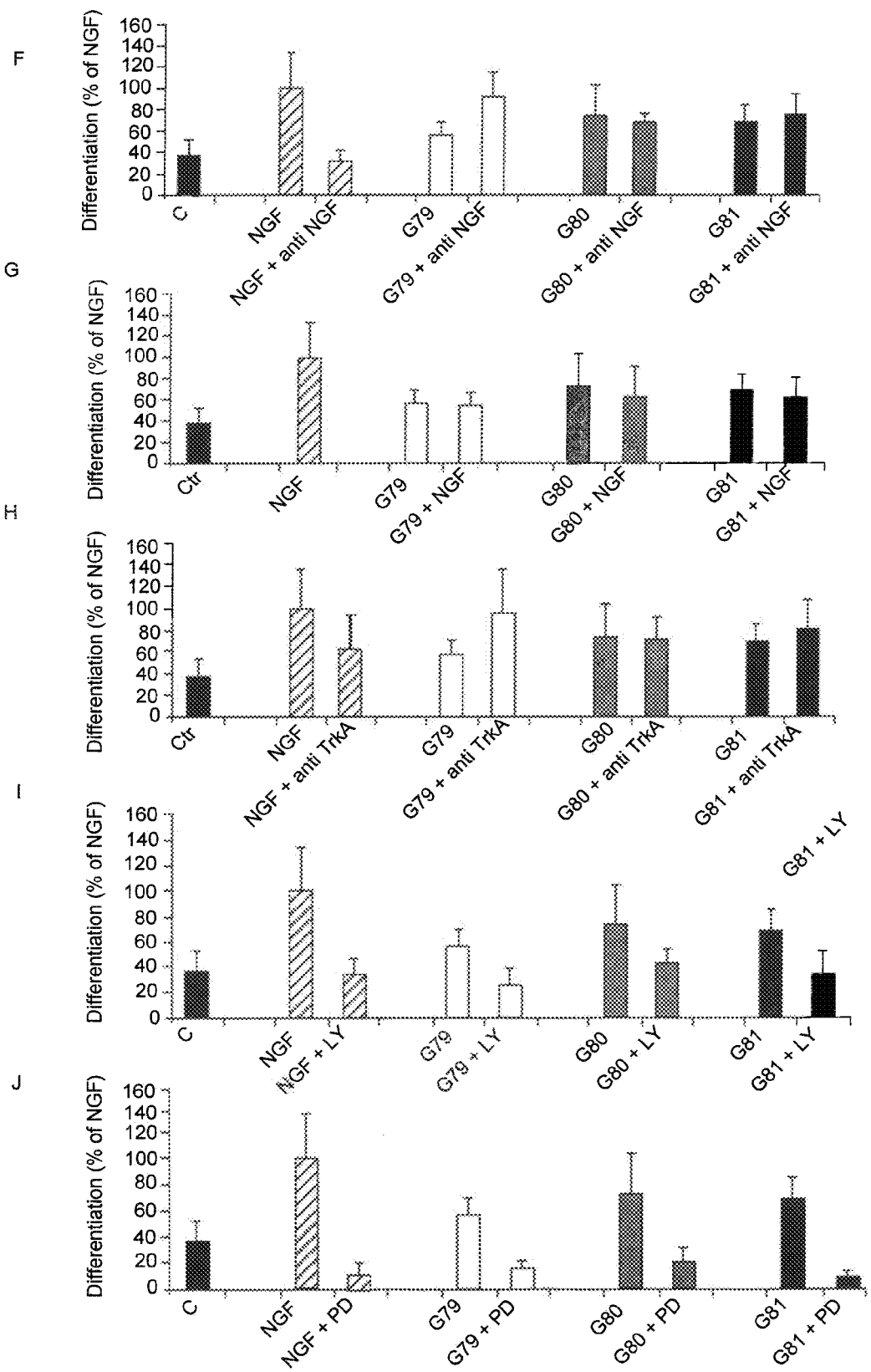

The percentage of differentiated cells is calculated as relative to NGF induced differentiation (FIG. 3F).

Example 5

Synergistic Activity Assay

G79, G80, and G81 do not have a Synergistic Activity with NGF.

To evaluate if the small molecules G79, G80, and G81 interfere with the maximal activity of NGF or lead to additive effects, PC12 cells were plated into collagen-coated 24-wells plates with 2.5% FBS and treated after 72 h with the small chemicals (each one at 100 ng/ml) in combination with NGF at the concentration of 100 ng/ml. In the same experiment PC12 cells were treated with the small molecules or NGF alone, as controls. The number of differentiated cells was evaluated after three days of treatment. The cell count was done in three randomly selected fields with 100 cells.

The results are shown in FIG. 3B. The treatment with G79, G80 or G81 molecules together with NGF decrease the activity of NGF, resulting into a decreased number of differentiated cells in the combination treatment NGF/G79-G80-G81. While the number of NGF differentiated cells in this experiment results to be 20±7.1, the number of differentiated cells obtained by the treatment NGF/G79 results to be 11.3±2.6. With the treatment NGF/G80 the number of differentiated cells obtained is 13±5.9. With the treatment NGF/G81 the number of differentiated cells obtained is 13.3±3.8. Overall, these results rule out that G79, G80 or G81 may have additive, synergistic or antagonistic effect with NGF. The percentage of differentiated cells is calculated as relative to NGF induced differentiation (FIG. 3G).

Example 6

Receptor Activation Assay

The hypothesis that G79, G80, and G81 can act through the binding to the extracellular portion of TrkA (binding site) and activate the tyrosine kinase receptor was tested by treating the PC12 cells with the small chemicals in combination with the antibody anti-TrkA or the K252a, a tyrosine kinase inhibitor. For this purpose PC12 cells were plated into collagen-coated 24-wells plates with 2.5% FBS and after 72 hrs were incubated with the small molecules alone or in combination with anti-TrkA antibody (AbCam, 1:2000) or K252a. NGF (100 ng/ml) was used as control and added alone or in combination with anti-TrkA antibody or K252a. The number of differentiated cells was evaluated after three days of treatment. The cell count was done in three randomly selected fields with 100 cells. The results are shown in FIG. 3C.

Treatment with G79, G80 and G81 molecules together with antibody anti-TrkA did not inhibit the differentiation of PC12 cells. While the number of differentiated cells by NGF is decreased by adding antiTrkA antibody (12.8±6.3 vs 20.7±7.1), the number of differentiated cells results to be similar. The G79/antiTrkA treatment induced the differentiation of PC12 cells: 19.6±8.1 vs 11.5±2.8 for the treatment with only G79; for G80/antiTrkA is 14.6±4.1 15.1±6.3 for the treatment with only G80; for G81/antiTrkA is 16.5±5.9 vs 14.1±3.3. The percentage of differentiated cells is calculated as relative to NGF induced differentiation (FIG. 3H).

Example 7

Signalling Inhibition Assays

G79, G80, and G81 Activate NGF Differentiation Pathway.

To evaluate if the transduction pathway induced by G79, G80, and G81 involves AKT and ERK activation, PC12 cell were treated with the test compounds in the presence of LY294002, an inhibitor of PI3K (an upstream activator of AKT) and PD98059, an inhibitor of MAPK kinase (an upstream activator of ERK). For this purpose, PC12 cells were plated into collagen-coated 24-wells plates with 2.5% FBS and after 72 hrs the cells were treated with the small molecules in combination with LY294002 (Sigma Aldrich, 10 μM) or PD98059 (Sigma Aldrich, 50 μM). NGF (100 ng/ml) was used as control and added alone or in combination with the inhibitors.

In order to assess if G79, G80 or G81 modulate TrkA signalling pathway, inhibitors of AKT and ERK pathway were used. Treatment with NGF plus LY294002 (FIG. 3D) decreased the number of differentiated cells compared to NGF alone (6.8±2.7 vs 20.7±7.1). In the same way, the treatment with G79 plus LY294002 decreased the number of differentiated cells compared to G79 alone (5.28±2.54 vs 11.5±2.8). Treatment with G80 plus LY294002 decreased the number of differentiated cells compared to G80 alone (8.5±2.6 vs 15.1±6.3). Treatment with G81 plus LY294002 decreased the number of differentiated cells compared to G81 alone (6.6±4.02 vs 14.1±3.3). The percentage of differentiated cells is calculated as relative to NGF induced differentiation (FIG. 3I).

Treatment with NGF plus PD98059 (FIG. 3E) decreased the number of differentiated cells compared to NGF alone (2.1±1.9 vs 20.7±7.1). In the same way the treatment with G79 plus PD98059 decreased the number of differentiated cells compared to G79 alone (3.1±1.06 vs 11.5±2.8). Treatment with G80 plus PD98059 decreased the number of differentiated cells compared to G80 alone (4±2.3 vs 15.1±6.3). Treatment with G81 plus PD98059 decreased the number of differentiated cells compared to G81 alone (1.6±1.1 vs 14.1±3.3). The percentage of differentiated cells is calculated as relative to NGF induced differentiation (FIG. 3J).

Example 8

Binding Assay

The binding of the test compounds, G79. G80, and G81, through the TrkA or p75 receptor can be tested by a cell-based competitive ELISA. At first PC12 cells are seeded into 96-well plates (Fisher Scientific) and incubated until 85%-90% of confluency. To test the binding of the test compounds to TrkA receptor, the p75 receptor expressed on PC12 surface is inhibited through the binding of a blocking antibody anti-p75 (AbCam) that binds the extracellular domain of the receptor. Cells are incubated for 45' with NGF at different increasing concentrations (0.01-0.1-1 nM) with or without each one of the small molecules as competitors at constant concentration. After one wash in cool PBS the cells are fixed for 15' with PFA 4%. Then, cells are washed with PBS and incubated with antibody anti-NGF (1 μg/ml) for 1 h a room temperature. Cells are rinsed twice with PBS and incubated with a secondary antibody anti-NGF for 1 h at room temperature (1:500; DyLight 488-conjugated antibody, Jackson ImmunoResearch). Cells are washed and fluorescence is read by a spectrofluorimeter at 488 nm.

Example 9

Glaucoma Model

G79 Prevents Neuronal Death in an Animal Model for Glaucoma.

12 Sprague Dawley rats (4 months of age) were anesthetized with isobutane and subjected to hypertonic saline solution injection into the episcleral vein of the right eye. Intraocular pressure (IOP) was measured before the operation and was monitored one time a week using a TonoLab for 7 weeks. Treatment with G79 was begun one week after glaucoma induction by topical application at the conjunctive. Two different experiments were performed.

In the first experiment, G79 was dissolved into physiological solution and was used at two different concentration (200 µg/ml and 400 µg/ml). NGF was used as positive control (200 µg/ml) and the physiological solution, used to dissolve all the molecules, was subministered as placebo. The animals were divided into 4 groups (3 animals in each group): glaucoma-G79 200 µg/ml; glaucoma-G79 400 µg/ml; glaucoma-NGF; glaucoma-placebo. The left eye was used as the control without glaucoma. In both experiments, seven weeks after glaucoma induction, animals were sacrificed by overdose of anaesthetic and their eyes were taken and fixed in 4% of PFA. The eyes were included in paraffin and cut into 20 µm sections to be used for histological studies (hematoxilin-eosin staining). The cell count of the number of retinal ganglion cells (RGC) was performed randomly in ten different fields for each eye.

Figure 4:
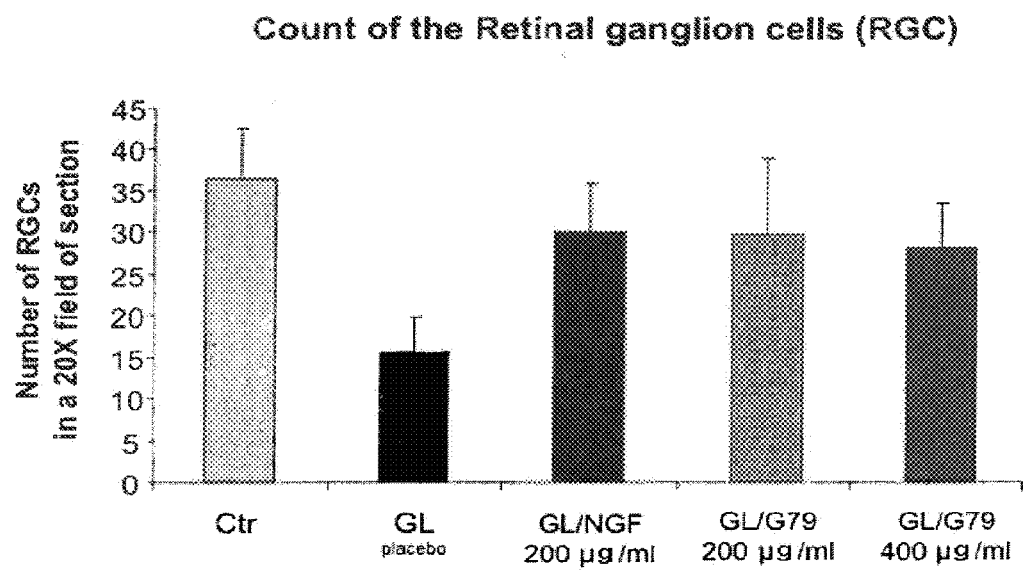
Figure 4:
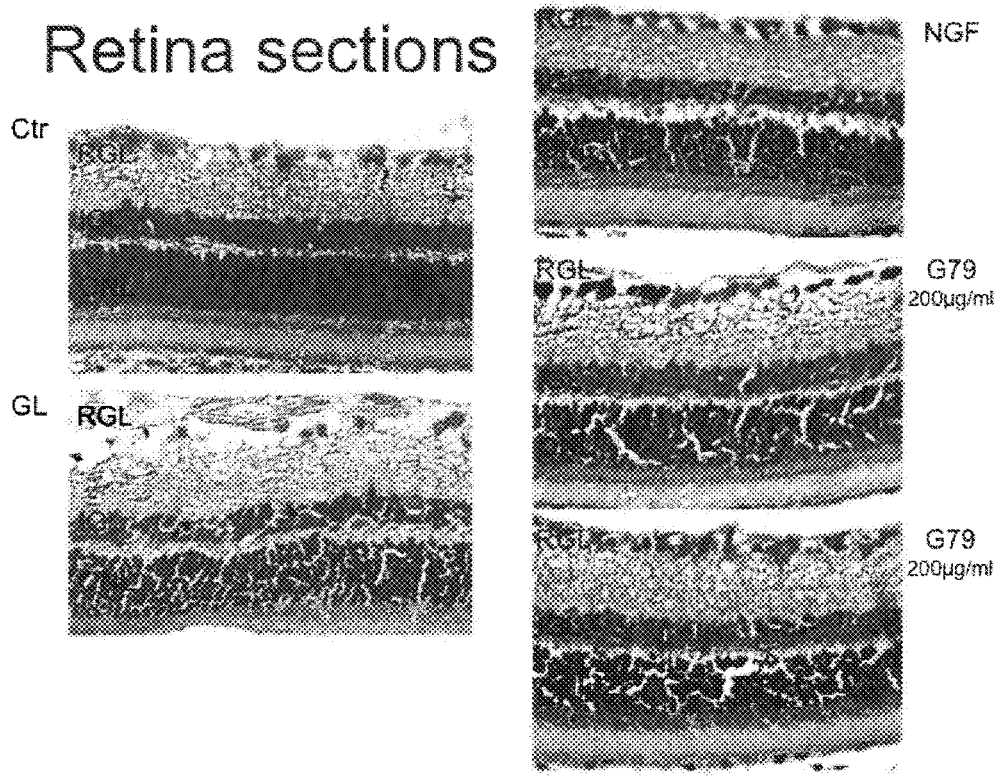

Rats were injected with a hypertonic solution in the eye that induced high intraocular pressure for five weeks. Animals were treated with eye drops of NGF (200 µM/ml), G79 (200-400 µM/ml) or placebo every day for five weeks. Animals with glaucoma and treated with placebo (saline) have a significant decrease in the number of retinal ganglion cells compared with control. By contrast, animals treated with NGF drops as well as animals treated with G79 have a significant protection of the ganglion cells (FIG. 4A). The results suggest that G79 treatment exerts neuroprotection on retinal ganglion cells (RGC).

Figure 4C:
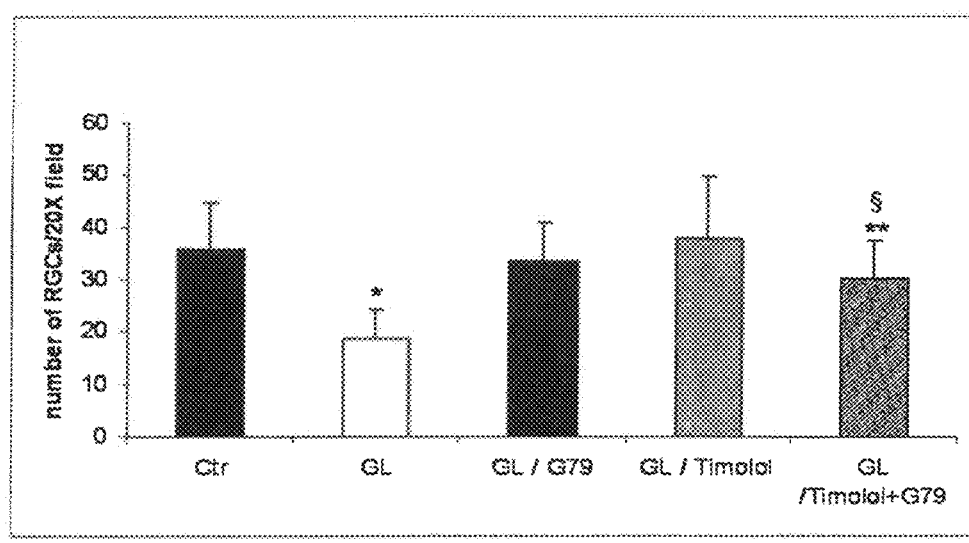

In the second experiment, G79 at the concentration of 200 µg/ml was used. The objective of this second experiment was to compare the efficacy of G79 to Timolol, the most common therapy for glaucoma that works by decreasing the intraocular pressure. Also in this experiment, a combinatory treatment with G79 and Timolol was performed. The animals were divided in 4 groups having 4 animals in each group: glaucoma-G79 (200 µg/ml) (n=4); glaucoma-Timolol (n=4); glaucoma-G79/Timolol (n=4); glaucoma-placebo (n=4). The left eye was used as the control without glaucoma. The results are shown in FIG. 4C, where G79 was compared to the current therapy for IOP in glaucoma, i.e., Timolol. IOP induction reduced significantly the number of RGC and this reduction was significant compared to the control eyes (C) ($p<0.0001$) and to all type of tested treatment ($p<0.0001$). The combination treatment did not exert additive effect in protecting RGCs (**GL/Timolol+G79 vs Ctr p=0.02; §GL/Timolol vs GL/Timolol+G79 p=0.003).

Example 10

Parkinson's Disease In Vitro Model (MPP Stress)

G79, G80, and G81 Prevent Neuronal Death in an In Vitro Model of Parkinson's Disease.

Cell Culture:

The human neuroblastoma cell line SH-SY5Y was maintained in culture with 50% Ham's F12 medium and 50% EMEM medium, supplemented with 10% FBS, 2 nM L-glutamine and 1% penicillin/streptomycin. The cell culture was maintained in a humidified atmosphere of 95% air and $CO_2$ at 37° C.

The human neuroblastoma cell line SH-SY5Y was used to study the neuroprotective effect of the small molecules in Parkinson's disease. The SH-SY5Y cells after differentiation to neuronal phenotype with retinoic acid, were pre-treated for 3 hours with the test compounds at different concentrations (20 ng/ml, 100 ng/ml, 2 µg/ml, 20 µg/ml and 50 µg/ml) or BDNF (20 ng/ml) as a positive control. Then 1-methyl-4-phenyl-1,2,3,6-tetrahydropyridine (MPTP) (100 µM) was added and incubated for 24 hrs. The number of surviving cells was determined the day after by 3-(4,5-dimethylthiazol-2-yl)-2,5-diphenyltetrazolium bromide (MTT) assay.

Figure 5:
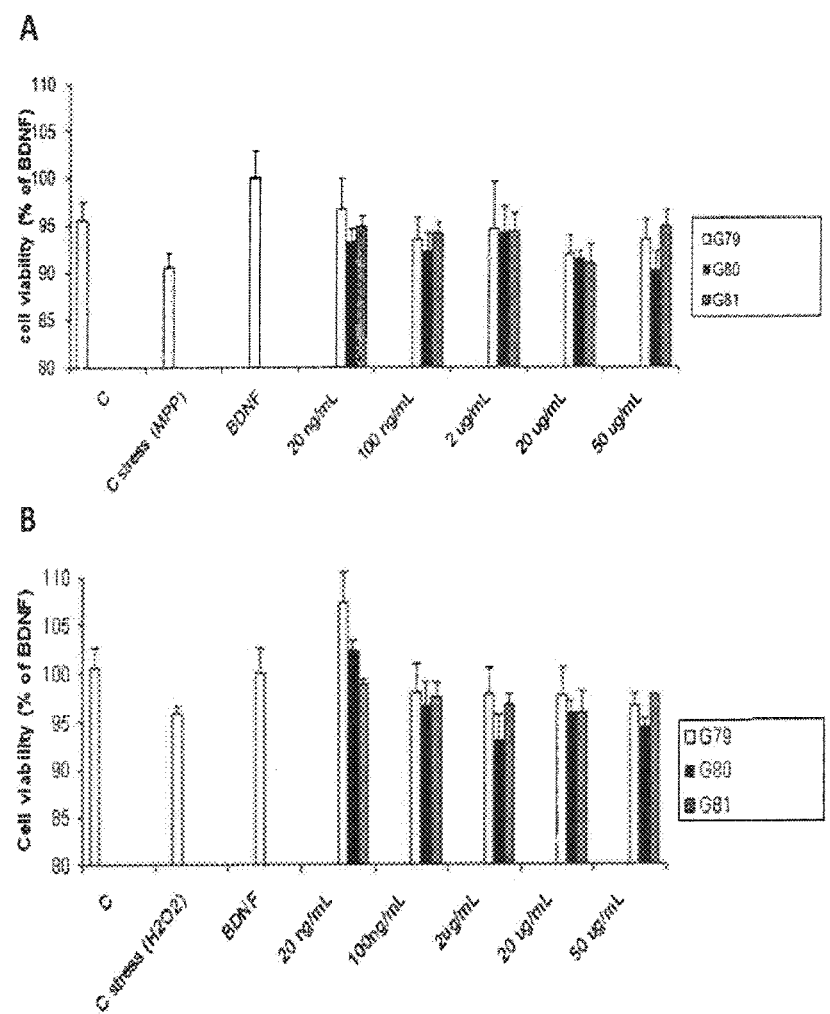
FIG. 5 depicts the results of G79, G80, and G81 in Parkinson's disease model (FIG. 5A) and in oxidative stress model (FIG. 5B).

The human neuroblastoma cell line SH-SY5Y was exposed to MPTP, which damage neurons through oxidative stress. Cells were treated with BDNF, G79, G80, G81 or placebo every day for five weeks. Cells treated with placebo (saline) have a significant loss of cells compared with control. By contrast, cells pretreated with BDNF as well as with G79 have a significant protection of neuronal cells (FIG. 5A).

Example 11

Oxidative Stress in the Human Cell Line SH-SY5Y

The human neuroblastoma cell line SH-SY5Y was used to study the neuroprotective effect of the test compounds G79, G80, and G81 in oxidative stress. The cells were pre-treated for 3 hours with the test compounds at different concentrations (20 ng/ml, 100 ng/ml, 2 µg/ml, 20 µg/ml and 50 µg/ml) or BDNF (20 ng/ml) as a positive control. Then $H_2O_2$ (100 µM) was added and incubated for 24 hrs. The number of surviving cells was determined by MTT assay. A protective effect was found of G79, G80 and G81 when using $H_2O_2$ for inducing oxidative stress in the SH-SY5Y neuronal cell line, with a more robust antioxidative effect of G79 than BDNF (FIG. 5B). In FIG. 5B, BDNF cell viability has been considered as the 100%. The $H_2O_2$ stress induced a decrease in the percentage of cell viability (no stress Ctr vs $H_2O_2$ stress=100±2% vs 95.9 f 0.5%). G79, compared to 080 and G81, is the one that exerted better protection, at the concentration of 20 ng/ml (BDNF vs G79=100±2.6 vs 107.4±5.8).

Example 12

Western Blot Analysis and Luminex Signalling Assay

G79 Activates the Neurotrophin Pathway

Figure 6:
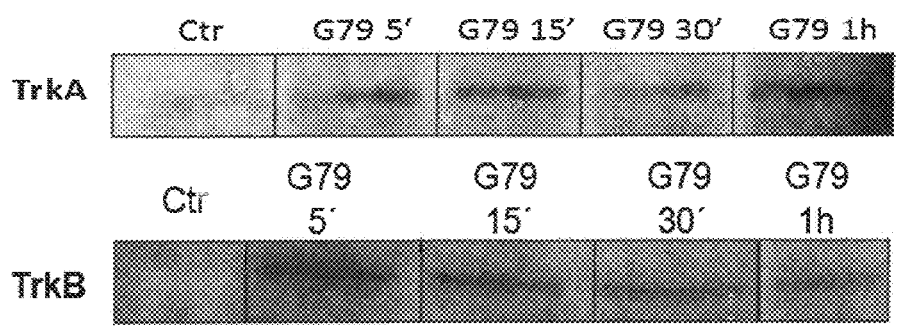
FIG. 6 depicts the fluorophoric images of the results of the Western blot analysis of PC12 cells treated with 100 ng/ml of G79.

Western Blot Analysis:

Neurotrophin receptors TrkA and TrkB activation (phosphorilation) was evaluated by Western-blot as follows: PC12 cell growing on 24-well plates were treated with low serum medium (0.5% FBS) to reduce the basal level of phosphorilation. After 24 h, the PC12 cells were treated with G79 (100 ng/ml), then recovered and lysated in 300 µl of ice-cold lysis buffer (Sigma Aldrich) at 5-15-30-60 min. After sonication, cell debris were removed by centrifugation (14000 rpm for 10 min) and equal amount of supernatant (30-35 µg/well) were loaded and separated by 10% polyacrilamide gel electrophoresis (PAGE) and then electroblotted onto PVDF membranes. Membranes were blocked by 5% nonfat milk and then sequentially incubated with the primary antibodies [phospho-TrkA, Tyr490 (Cell Signaling) or phospho-TrkB, Tyr515 (NovusBiological)]1:1000 over-night and the secondary antibodies 1:2000, for 1 h at room temperature. Blots were processed for visualization by chemiluminescence system (Amersham) and exposed to Kodak film to visualize the fluorographic image. As shown in FIG. 6, both receptors were phosphorilated already after 5 min.

Luminex Signalling Assay:

The human neuroblastoma cell line SH-SY5Y was used to perform Luminex signalling assays using the 10-Plex MAPK/SAPK Signaling Kit-Phosphoprotein (Millipore). This cell line expresses the TrkB receptor and the MAPK/SAPK signalling pathway is typically activated by the tyrosinkinase receptors. The phosphoprotein antibodies included into the kit are the following: ERK/MAP kinase (Thr185/Tyr187); STAT-1 (Tyr701); JNK (Thr183/Tyr185); MEK-1 (Ser212); ATF-2 (Thr69/71); p53 (Ser15); HSP27 (Ser78); c-Jun (Ser73); p38 (Thr180/Tyr182), p70 S6 kinase (Thr412); IkBα (Ser32) (purchased from Millipore).

The cells were propagated and then seeded into 24-well plates (30.000 cell/well). After 24 hours, the cells were treated with two different concentrations of NGF-receptor agonist G79: 100 ng/ml and 20 µg/ml. After adding G79 into the medium, the cells were collected in the lysis buffer of the kit at the following time points: 30 min, 1 h, 2 h, and 6 h. The assay was performed in this way to assess both time and dose effects comparing the treated samples with the untreated cells used as negative controls (unstimulated SH-SY5Y cells). BDNF was used as positive control at the concentration 20 ng/ml, which is the best working concentration known in literature. In the Luminex plate, each sample was added into a well in duplicate. After adding all the samples, the specific positive and negative controls of phosphorilation, included in the Luminex kit, were added. The assay buffer was also added in duplicate, as a background controls.

Figure 7:
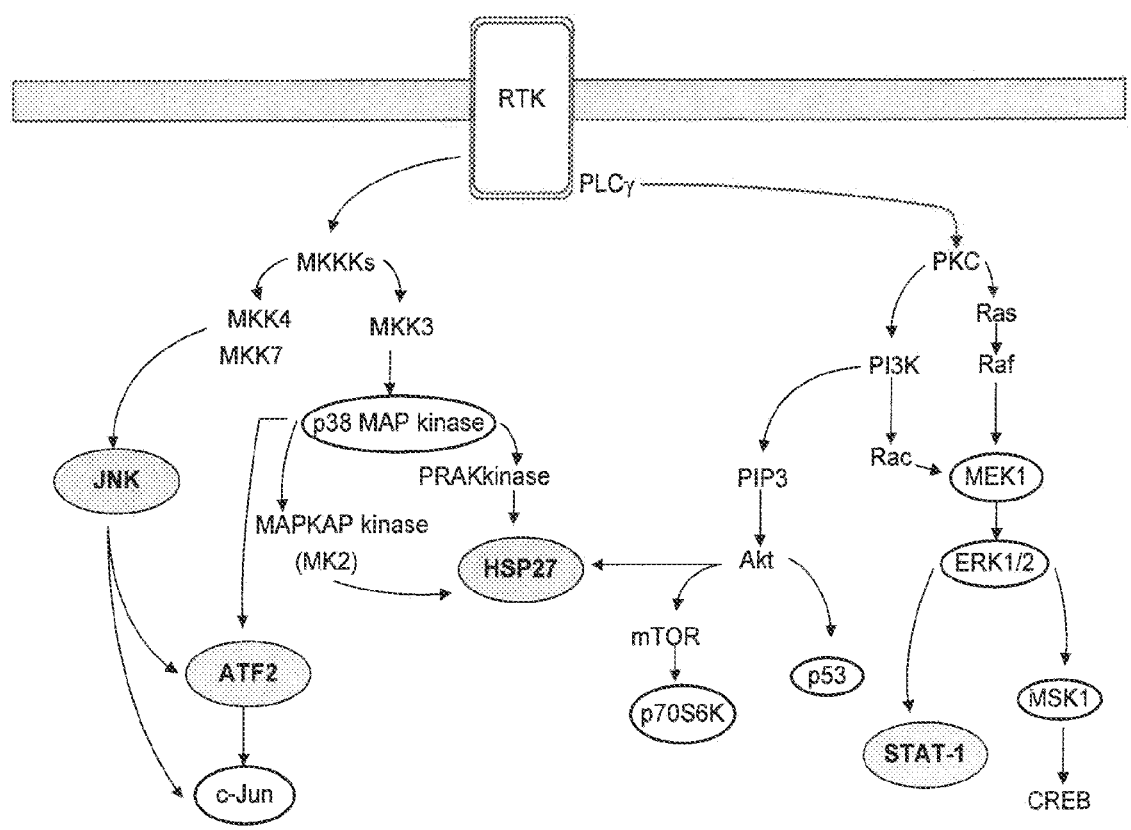
FIG. 7 shows the intracellular pathway activated by the phosphorylation of the receptor tyrosine kinase (RTK).
Figure 8:
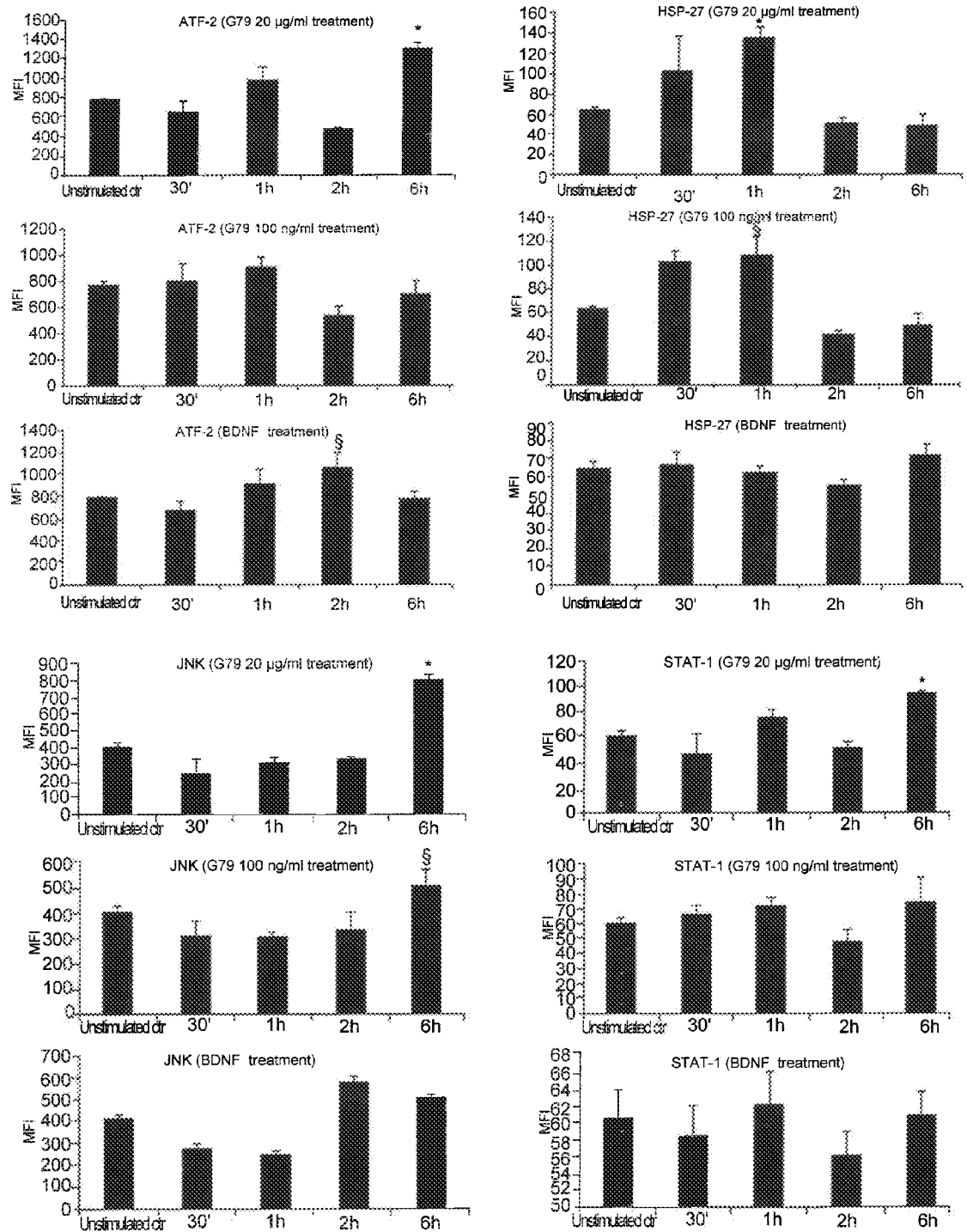
FIG. 8 depicts the effects of G79 and BDNF on the levels of activation of the phosphoproteins ATF-2, HSP-27, JNK, and STAT-1 tested by Luminex technology.

FIG. 7 shows the intracellular pathway activated by the phosphorilation of the receptor tyrosine kinase (RTK). In the circles are the activated factors, while in the grey circles are the tested factors. Its effects of the SY-SY5Y cell line in the phosphorilation of several pathways were assessed using xMAP assay from Luminex. FIG. 8 shows the levels of activation of the phosphoproteins tested by Luminex technology. The levels of activation are expressed as Median Fluorescence Intensity (MFI). As tested by Luminex technology, ATF-2, HSP-27, JNK and STAT-1 resulted to be modulated and significantly phospho-activated compared to the unstimulated control. FIG. 8 shows the graphics of the MFI for both G79 and BDNF treatments, at different timepoints.

ATF-2 was significantly activated at 6 h after G79 treatment (20 µg/ml), compared to unstimulated control (*p<0.05). The BDNF control shows significant ATF-2 activation at 2 h after treatment (§p<0.05). HSP-27 was significantly activated at 1 h after G79 treatment (both at 20 µg/ml and 100 ng/ml), compared to unstimulated control (*p<0.05). The BDNF does not activate HSP-27. JNK was significantly activated at 6 h after G79 treatment (both at 20 µg/ml and 100 ng/ml), compared to unstimulated control (* and §p<0.05). The BDNF control showed significant JNK activation at 2 h after treatment (✝p<0.05). STAT-1 was significantly activated at 6 h after G79 treatment (20 µg/ml), compared to unstimulated control (*p<0.05). The BDNF did not activate STAT-1.

Example 13

Cytometry Binding Assay

G79 Competes with NGF and BDNF for the Binding to Neurotrophin Receptors

In order to assess the binding of G79 to the TrkA (PC12 cells) and TrkB receptors (SH-SY5Y), we performed competitive binding assays by flow cytometry. In order to assess the binding competition between p75 and TrkA, PC12 cells expressing both TrkA and p75 receptors were cultivated in normal growth medium. After detaching cells by trypsin solution, 200,000 cells/well were added to tubes for the following incubations. One tube contains control untreated cells. In the other tubes, cells were pre-incubated for 45 minutes with different concentrations of NGF (0-10-20-50-100 ng/ml), that can directly bind both TrkA and p75 receptors, blocking the possible binding of G79 if it competes for the same receptors. Then, without washing the cells, G79 conjugated with FITC fluorescence (100 ng/ml) was added and so incubated the cells for 1 hour. Samples were read in a cytometer (FCAScan).

To detect the binding separately on both receptors, a prior incubation of cells (before NGF incubation) with blocking antibodies was made. The cells were preincubated for 1 hour with blocking antibody anti-p75 (1:100; Chemicon Int.), to detect the binding on TrkA, or blocking antibody anti-TrkA (1:200; AbCam) to detect the binding on p75. The same experimental protocol was repeated with SH-SY5Y cell line to detect the binding with TrkB and p75 on these cells. In this case BDNF was used as a competitor for the binding on TrkB and p75. All the results are expressed as mean channel fluorescence (MCF), which is a measure of the cell surface fluorescence produced by G79-FITC binding.

FIG. 9A shows that signal (MCF) decreases in presence of growing concentration of NGF, meaning that G79 competes for the binding on the same NGF-receptors. In order to assess the binding on p75, cells were pre-incubated with anti-TrkA antibody, wherein it was found that signal (MCF) steel decreases, which indicates that G79 could bind on p75 receptor (FIG. 9B). In order to assess the binding on TrkA, pre-incubation with the antibody anti-p75 did not change the signal (MCF), meaning that G79 apparently does not compete with NGF for the binding on TrkA (FIG. 9C). However, this result could be affected by the presence of very small amounts of TrkA on cell surface, compared to the much higher presence of p75 (~75000 receptors per cell). Similarly, the binding of G79 to TrkB was assessed using the SH-SY5Y cell line (FIG. 9D). In this case, signal (MCF) decreased in the presence of growing concentrations of BDNF, indicating that G79 competes with BDNF to one of its receptors.

Example 14

In Vitro Model of Amyotrophic Lateral Sclerosis (ALS)

G79, G80, and G81 are Neuroprotective in the In Vitro Model of ALS

Cell Culture:

Mouse motoneuron-like cells NCS-34 were cultured in DMEM (Gibco) supplemented with 10% heat inactivated FBS and 1% penicillin/streptomycin. The cell culture was maintained in a humidified atmosphere of 95% air and $CO_2$ at 37° C.

The nutritional deprivation stress in motorneurons was conducted as described previously in Masahito T. et al., *J. Neuropathol. Exp. Neurol.* 65(8):816-825 (2006). To assess the effect of trophic stress condition on ALS, the presence of apoptosis was investigated using serum deprivation. NSC-34 cells were seeded in 24-well poly-lysinated plates at 30,000 cells/well and preincubated for 24 h in DMEM plus 10% FBS with various doses of G79, G80, and G81 (20 ng/ml, 100 ng/ml, 2 µg/ml, 20 µg/ml, 50 µg/ml), and G-CSF (2 µg/ml) or BDNF (20 ng/ml) which both were used as positive controls (Masahito T. et al., ibid; Elliot J. L., *Neurobiology of Disease* 6:310-320 (1999)). Then, the medium was removed and replaced with fresh DMEM without FBS. After 48 h, cell viability was assayed by MTT assay, as described previously.

As shown in FIG. 10, G79, G80 and G81 exerted neuroprotection on motorneurons challenged with serum deprivation. Cell viability is expressed as the percentage relative to the control without stress. G79 showed the best neuroprotective effect at the concentration of 100 ng/ml, with a significant increase in cell viability compared to stress-Ctr (98.11±6.14% vs 69.64±10.12%; p=0.02). Also G79 showed increased cell viability compared to both the positive controls, G-CSF and BDNF, even if not significant (G-CSF cell viability: 76.50-8.3%; BDNF cell viability: 80.62-5.2).

Example 15

Experimental Autoimmune Encephalomyelitis (EAE) Model

G79 Ameliorates the Animal Model of Multiple Sclerosis (MS)

The effect of G79 was tested in the animal model of MS, the experimental autoimmune encephalomyelitis (EAE), by performing a preventive trial (in which the therapy starts at the time of the induction of the disease) and a curative trial (in which the therapy starts when the animals are already suffering from the disease). Female C57BL/6 mice from Harlan (8-12 weeks old) were immunized subcutaneously in both hind pads with 300 µg of myelin oligodendrocyte glycoprotein (MOG) peptide 35-55 (Spikem, Firenze) emulsified with 50 µg of *Mycobacterium tuberculosis* (H37Ra strain; Difco, Detroit, Mich.) in incomplete Freund's adjuvant (IFA) as previously described in Palacios et al., 2007. The mice were injected intraperitoneally with Pertussis toxin (Sigma) (500 ng) at the time of immunization and 2 days later. The animals were weighted and inspected for clinical signs of disease on a daily basis by a blinded observer. The severity of the disease EAE was assessed for 30 days according to the following scale: 0=normal; 0.5=mild limp tail; 1=limp tail; 2=mild paraparesis of the hind limbs, unsteady gait; 3=moderate paraparesis, voluntary movements still possible; 4=paraplegia or tetraparesis; 5=moribund state. At the end of the study, the mice were anesthetized and perfused intracardially with 4% of paraformaldehyde in 0.1 M phosphate buffer (pH 7.6). The brains, spinal cords and spleens were dissected and either fixed or frozen until use. Also serum was obtained from all the animals included in the study. This procedure was approved by the University of Barcelona Committee on Animal Care.

Two different experiments were performed to assess both the preventive effect and curative effect of G79, compared to other drugs targeting neurotrophin pathway (Gambogic amide and Xaliproden) or one of the first line therapy for the treatment of MS, i.e., Glatiramer acetate.

For the preventive trial, 10 animals were treated with intraperitoneal injection of G79 at the concentration of 40 mg/kg, 10 animals were treated with intraperitoneal injection of G79 at the concentration of 100 mg/kg, 10 animals were treated with intraperitoneal injection of Gambogic amide at the concentration of 2 mg/kg, 10 animals were treated with oral administration of Xaliproden at the concentration of 10 mg/kg. As both Gambogic amide and Xaliproden were diluted with different percentage of DMSO, 5 animals were treated with intraperitoneal injection of placebo (physiologic solution plus 1% DMSO) and other 5 animals were treated with placebo oral (physiologic solution plus 2.5% DMSO), respectively. The treatments were performed daily, starting after the immunization day.

For the curative trial, to reduce the discrepancy between the oral administration and intraperitoneal injections, as stress can deeply affect the development of the clinical scores in animals, all the treatments were performed by intraperitoneal injections. For this study, 8 animals were treated with G79 at the concentration of 40 mg/kg, 8 animals were treated with G79 at the concentration of 100 mg/kg, 8 animals were treated with Gambogic amide at the concentration of 2 mg/kg, 8 animals were treated with Xaliproden at the concentration of 10 mg/kg, 8 animals were treated with Glatiramer acetate at the concentration of 5 mg/kg, 8 animals were treated with placebo (physiologic solution plus 2.5% DMSO). The treatments were performed daily starting after the increase of the clinical score at score 2 (after the second day at this score).

FIG. 11A and FIG. 11B show the results of the preventive application of G79 in the in vivo model of MS (onset therapy in the same day of disease induction). The graphics shows the clinical score of the mice affected by EAE and treated with different drugs since the day of the immunization. In FIG. 11A, the animals treated with G79 show a delay in the presence of the disease, although not significant. In particular, the concentration of 100 mg/Kg was more effective in delaying the disease. Also the final clinical score, at day $30^{th}$, of the animals treated with G79 100 mg/Kg was lower compared to placebo treated animals.

FIG. 12 shows the results of the curative trial. G79 at the dose of 100 mg/Kg, shows the best therapeutic effect in ameliorating the clinical score. In particular G79, compared to placebo, decreased the clinical score significantly, between the day $16^{th}$ and $23^{rd}$ ($16^{th}$ day: G79 score 2.8±1.2 vs placebo score 4±0.7, p=0.01; day $19^{th}$: G79 score 1.75±1 vs placebo score 3.3±0.5, p=0.003; G79 score 1.6±0.8 vs placebo score 2.8±0.8, p=0.02). Also G79 100 mg/Kg exerted a better therapeutic effect compared to the other tested treatments (Gambogic amide, Xaliproden, Glatiramer acetate).

Example 16

Neuroinflammation In Vitro Model

G79 Reduces Neuroinflammation in an In Vitro Model of Neuroinflammation

Brain inflammation is a common process in many neurological diseases and it is prominent in the case of MS. In order to assess the effect of G79 in brain inflammation, its effect was tested in an in vitro model of neuroinflammation using organotypic cerebellar cultures challenged with endotoxin. First, the effect of G79 was tested in the induction of the enzyme iNOS, which produce nitric oxide and promoted inflammation. As shown in FIG. 13, G79 decreased the expression of iNOS. Samples pre-treated with G79 showed a decrease in the expression of iNOS 24 h after the challenge with LPS, compared to the placebo pre-treated samples.

Regarding the effect of G79 in the release of pro-inflammatory cytokines, the levels of TNFα and IL-1β were tested in the supernatants from organotypic cerebellar cultures challenged with LPS. FIG. 14A shows the production of TNFα in cerebellar organotypic culture. The production of TNFα was reduced at 6 and 12 hours in organotypic culture pre-treated with G79 compared to placebo. FIG. 14B shows the production of IL-1β in cerebellar organotypic culture. The pre-treatment with G79 did not affect the release of IL-1β.

In Vitro Model of Neuroinflammation in Cerebellar Organotypic Slice Culture:

Neonates mice (day 8 after birth (P8)) were decapitated after anaesthetic IP injection and whole brains were removed aseptically. Cerebellum was separated from the rest of the brain and placed on a metal vibratome plate. Once the cerebellum was attached to the surface of the plate, 400 μm sagittal sections were cut using the vibratome. The slices were then transferred with a plastic Pasteur pipette to a cell culture plate containing an organotypic culture medium (5% $CO_2$ in 50% basal medium with Earle's salt, 25% Hank's buffered salt solution, 25% inactivated horse serum, 5 mg/ml glucose, 0.25 mM L-glutamine and 25 μg/ml penicillin/streptomycin). After separating and isolating each slice, the cerebellar slices were then transferred to 6-well plates (3 slices for each well) containing a 30 mm culture plate insert with 0.4 μm pores (Millipore) and 1 ml full culture medium, pre-conditioned by incubation for at least 2 hours at 37° C., and 5% $CO_2$ was added into each well below the insert. The six-well plates were kept at 37° C. and under 5% $CO_2$, and half the medium was replaced every 2 days. All the experiments were performed after 1 week of culture in such conditions.

After one week of organotypic cerebellum culture, the medium of each well was replaced with fresh medium and G79 (100 ng/ml) or placebo (physiologic solution) was added to the wells and kept in incubation for 1 hour. Then lipopolysaccharide (LPS) (15 μg/ml) was added and kept in incubation. Slices and organotypic culture medium were recovered at different time points: 0 h, 1 h, 3 h, 6 h, 12 h, 24 h, and 48 h. For each time point, untreated slices of control, LPS/placebo treated slices and a LPS/G79 treated slices were obtained. Slices were collected in three different experiments for RNA extraction. For this purpose, slices were recovered directly in RNA Lysis Buffer (Qiagen) and frozen at −20° in the same buffer. In the other three different experiments, slices were recovered for immunofluorescence and fixed in 4% paraformaldehyde (PFA) for 45 minutes at room temperature. In all the experiments, organotypic culture medium was collected and stored at −20° for ELISA assay.

Real-Time Quantitative Polymerase Chain Reaction:

Organotypic slices collected from the LPS stimulation experiment were homogenized in RNA lysis buffer. Total RNA was extracted using the RNeasy Mini Kit (Qiagen, Chatwworth, Calif.) isolation system, including DNase treatment using the RNase-Free DNase Set (Quiagen). Total RNA (35 μg) was reverse transcribed using the Reverse Transcription System (High Capacity cDNA Archive Kit; Applied Biosystems, Foster City, Calif.). The real time reaction was conducted at 25° C. for 10 minutes, followed by 37° C. for 2 hours, and finally stored at 4° C. Primers and target-specific fluorescence-labeled TaqMan probes were purchased from Applied Biosystems (TaqMan Gene Expression assays). The primer for the gene of iNOS was used. The TaqMan Universal Master Mix (Applied biosystems) was used. Amplification of complementary DNA was performed on a DNA Engine Opticon 2 Real-Time System (MJ Research, Watertown, Mass.) using 0.9 μM for each primer and 0.25 μM for the probe and 20 ng complementary DNA. The reaction conditions were as follows: an initial 2 minutes at 50° C., followed by 10 minutes at 95° C., and 40 cycles of 15 seconds at 95° C., and 1 minute at 60° C. Each sample was run in triplicate, and in each plate the target and the endogenous control were amplified in the same well. The expression of the gene tested was quantified relative to the level of the housekeeping gene GAPDH.

ELISA Assay:

The supernatants from cerebellar organotypic culture medium were used to assay cytokine production such as IL-1-β and TNF-α by ELISA. For IL-1-β, Quantikine Immunoassay IL-1-13 kit (R&D System) was used, and for TNF-α the ELISA Development kit for mouse TNF-α (Peprotec) was used. All the ELISA assays were performed according the manufacture's instructions.

Example 17

Transport Through the Blood-Brain Barrier (BBB)

The ability of the compounds G79, G80 and G81 to cross the blood-brain barrier was tested using two in vitro models. The passive transport was tested using the PAMPA (Parallel Artificial Membrane Permeability Assay) model and the active transport was tested using an in vitro model of the BBB by co-culturing BBEC and astrocytes. As a result, it was found that G79 was unable to cross the BBB in the PAMPA model compared to other drugs with a good ability for crossing in the PAMPA model, such as propanolol and carbamazepine (Effective permeability (pe) propanolol=11.5; pe carbamazepine=10.3; pe G79=0×$10^{-6}$ cm/s). By contrast, in the in vitro cell model of the BBB, all three molecules displayed medium to high crossing of the BBB by active transport (pe G79=4.1; pe G80=2.8; pe G81=2.1×$10^{-6}$ cm/s).

Parallel Artificial Membrane Permeability Assay (PAMPA) Assay:

PAMPA is used as an in vitro model of passive BBB permeability. An artificial membrane immobilized on a filter is placed between a donor and acceptor compartment. At the start of the test, a drug is introduced in the donor compartment. Following the permeation period, the concentration of the drug in the donor and acceptor compartments are measured using UV spectroscopy. Therefore the permeability of any compound with a UV chromophore can be determined by this method.

The tested compound stock solutions were diluted 200-fold in universal buffer at pH 7.4 and added to the donor wells. The filter membrane was coated with PBL in dodecane and the acceptor well was filled with pH 7.4 buffer. The acceptor filter plate was carefully put on the donor plate to form a 'sandwich' (consisting of the aqueous donor with test the compound on the bottom, an artificial lipid membrane in the middle, and an aqueous acceptor on the top). The test compound diffused from the donor well through the lipid membrane and into the acceptor well. The 'sandwich' was left undisturbed for 18 hrs while the permeation occurred. The concentration of the test compound in the acceptor, the donor, and the reference wells was determined using the UV plate reader. Effective permeability (Pe) of each compound was calculated by using the pION PSR4p software. Samples were analyzed in triplicate and the average of the three runs was reported. Quality control standards were run with each sample set to monitor the consistency of the analysis set.

Cellular In Vitro Model of Transport Through the Blood-Brain Barrier (BBB):

The cellular in vitro model was established by using a co-culture of blood-brain endothelial cells (BBECs) and newborn rat astrocytes. In brief, before cell co-culture (24-well polycarbonate transwell with a surface area of 0.33 cm$^2$ and pore-size of 0.4 µm, Corning Costar), the upper surface of plate inserts was coated with collagen type IV and fibronectin. Next, the inserts were placed upside down in a large petri dish and 40 µL of a suspension (containing approximately 45,000 astrocytes) was placed on the bottom of each filter. The Petri dish was placed in an incubator for 1 hour and 40 µL of fresh DMEM+S was added to the bottom of each filter every 15 minutes. The inserts were then transferred back into the plate and incubated at 37° C., 5% $CO_2$ for three days. After this time, 2 hours before seeding the BBECs, the medium was replaced by DMEM+S supplemented with 125 µg/ml of heparin. Two hours later, cells were seeded in the inserts (45,000 cells per filter). The plate was kept in the incubator at 37° C., 5% $CO_2$ for three more days. After three days of co-culture, the medium was replaced by DMEM+S supplemented with cAMP and RO-20-1724, and kept at 37° C. and 5% $CO_2$. On day 8 of co-culture, transendothelial electrical resistance (TEER) measures showed that the system was ready for transport studies. To validate the maturity of the model, on the same day of the experiment, permeability assays were done in parallel with lucifer yellow (LY) as an integrity marker of the in vitro barrier. During the permeability assay the samples were co-incubated with LY at a concentration of 20 µM to assess the integrity of the cellular monolayer during the assay.

The TEER was determined by using an ohmmeter Millicell ERS system (MERS 000 01, Millipore). TEER measures confirm formation of a functionally intact in vitro BBB by day 8 of co-culture. The TEER values represent the tightness or integrity of the in vitro BBB. The TEER value (mean±SD) for all wells was 141±5.7 ohms/cm$^2$.

$$Papp=(dQ/dt)*(1/A)*(1/C_0) \text{(cm/s)} \quad (1)$$

In the above equation (1), (dQ/dt) is the amount of the compound present in the acceptor compartment in function of time (nmol/s), A is the area of the insert (cm$^2$) and $C_0$ is the initial concentration of the compound applied to the donor compartment (nmol/ml).

During transport studies, compounds were co-incubated with LY (20 µM) in order to ensure the integrity of the cell membrane during the transport assay.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

REFERENCES

Aloe L, Calzá L (2004) Progress in brain research. Vol 146, NGF and related molecules in health and diseases. Amsterdam: Elsevier.

Anand P. Neurotrophic factors and their receptors in human sensory neuropathies. Prog Brain Res. 2004; 146:477-92.

Apfel S (2002) Nerve growth factor for the treatment of diabetic neuropathy: what went wrong, what went right, and what does the future hold? Int Rev Neurobiol 50:393-413.

Barker P (1998) p75NTR: A study in contrasts. Cell Death Differ 5:346-356.

Bhakar A, Howell J, Paul C, Salehi A, Becker E, Said F, Bonni A, Barker P (2003) Apoptosis induced by p75NTR overexpression requires Jun kinase-dependent phosphorylation of Bad. J Neurosci 23:11373-11381.

Chao M (2003) Neurotrophins and their receptors: a convergence point for many signalling pathways. Nat Rev Neurosci 4:299-309.

Faden A I, Stoica B. Neuroprotection: challenges and opportunities. Arch Neurol. 2007 June; 64(6):794-800.

Foehr E, Lin X, O'Mahony A, Geleziunas R, Bradshaw R, Greene W (2000) NF-kappa B signaling promotes both cell survival and neurite process formation in nerve growth factor-stimulated PC12 cells. J Neurosci 20:7556-7563.

Frade J (2005) Nuclear translocation of the p75 neurotrophin receptor cytoplasmic domain in response to neurotrophin binding. J Neurosci 25:1407-1411.

Gentry J, Casaccia-Bonnefil P, Carter B (2000) Nerve growth factor activation of nuclear factor kappaB through its p75 receptor is an anti-apoptotic signal in RN22 schwannoma cells. J Biol Chem 275:7558-7565.

Ghosh S, May M, Kopp E (1998) NF-kappa B and Rel proteins: evolutionarily conserved mediators of immune responses. Annu Rev Immunol 16:225-260.

Greene L, Tischler A (1976) Establishment of a noradrenergic clonal line of rat adrenal pheochromocytoma cells which respond to nerve growth factor. Proc Natl Acad Sci USA 73:2424-2428.

Hellweg R, Ziegenhorn A, Heuser I, Deuschle M. Serum concentrations of nerve growth factor and brain-derived neurotrophic factor in depressed patients before and after antidepressant treatment. Pharmacopsychiatry. 2008 March; 41(2):66-71.

Huang E, Reichardt L (2003) Trk receptors: roles in neuronal signal transduction. Annu Rev Biochem 72:609-642. Epub 2003 March 2027.

Kaplan D, Miller F (2000) Neurotrophin signal transduction in the nervous system. Curr Opin Neurobiol 10:381-391.

Levi-Montalcini R (1987) The nerve growth factor 35 years later. Science 237:1154-1162.

Lewin G, Barde Y (1996) Physiology of the neurotrophins. Annu Rev Neurosci 19:289-317.

Longo F, Manthorpe M, Xie Y, Varon S (1997) Synthetic NGF peptide derivatives prevent neuronal death via a p75 receptor-dependent mechanism. J Neurosci Res 48:1-17.

Longo F M, Yang T, Knowles J K, Xie Y, Moore L A, Massa S M. Small molecule neurotrophin receptor ligands: novel strategies for targeting Alzheimer's disease mechanisms. Curr Alzheimer Res. 2007 December; 4(5):503-6.

Maliartchouk S, Debeir T, Beglova N, Cuello A, Gehring K, Saragovi H (2000a) Genuine monovalent ligands of TrkA nerve growth factor receptors reveal a novel pharmacological mechanism of action. J Biol Chem 275:9946-9956.

Maliartchouk S, Feng Y, Ivanisevic L, Debeir T, Cuello A, Burgess K, Saragovi H (2000b) A designed peptidomimetic agonistic ligand of TrkA nerve growth factor receptors. Mol Pharmacol 57:385-391.

Martinez-Forero I, Garcia-Munoz R, Martinez-Pasamar S, Inoges S, Lopez-Diaz de Cerio A, Palacios R, Sepulcre J, Moreno B, Gonzalez Z, Fernandez-Diez B, Melero I, Bendandi M, Villoslada P (2008) IL-10 suppressor activity and ex vivo Tr1 cell function are impaired in multiple sclerosis. Eur J Immunol 38:576-586.

Masip, I.; Cortés, N.; Abad, M.; Guardiola, M.; Pérez-Payá, E.; Ferragut, J.; Ferrer-Montiel, A.; Messeguer, A. (2005). Design and synthesis of an optimized positional scanning library of peptoids: identification of novel multidrug resistance reversal agents. Bioorg. Med. Chem. 13, 1923-1929.

Miller S, Simon R, NG S, Zuckermann R, Kerr J, Moos W (1994) Bioorg Med Chem Letter 4:2657-2662.

Moreno B, Hevia H, Santamaria M, Sepulcre J, Munoz J, Garcia-Trevijano E, Berasain C, Corrales F, Avila M, Villoslada P (2006) Methylthioadenosine reverses brain autoimmune disease. Ann Neurol 60:323-334.

Palacios, et al., PloSONE 2007; 2(11): e1222.

Palacios R, Comas D, Elorza J, Villoslada P (2008) Genomic regulation of CTLA4 and multiple sclerosis. J Neuroimmunol 203:108-115.

Peleshok J, Saragovi H (2006) Functional mimetics of neurotrophins and their receptors. Biochem Soc Trans 34:612-617.

Poduslo J, Curran G (1996) Permeability at the blood-brain and blood-nerve barriers of the neurotrophic factors: NGF, CNTF, NT-3, BDNF. Brain Res Mol Brain Res 36:280-286.

Price R D, Milne S A, Sharkey J, Matsuoka N. Advances in small molecules promoting neurotrophic function. Pharmacol Ther. 2007 August; 115(2):292-306.

Rabizadeh S, Ye X, Wang J, Bredesen D (1999) Neurotrophin dependence mediated by p75NTR: contrast between rescue by BDNF and NGF. Cell Death Differ 6:1222-1227.

Saragovi H, Zaccaro M (2002) Small molecule peptidomimetic ligands of neurotrophin receptors, identifying binding sites, activation sites and regulatory sites. Curr Pharm Des 8:2201-2216.

Schulte-Herbrüggen O, Braun A, Rochlitzer S, Jockers-Scherübl M C, Hellweg R. Neurotrophic factors—a tool for therapeutic strategies in neurological, neuropsychiatric and neuroimmunological diseases? Curr Med. Chem. 2007:14(22):2318-29.

Sen, S., Roach, S. A convenient Two-step procedure for the Synthesis of Substituted Allylic amines from Allylic Alcohols. Synthesis, 1995, 756-758.)

Shi Z, Birman E, Saragovi H U. Neurotrophic rationale in glaucoma: a TrkA agonist, but not NGF or a p75 antagonist, protects retinal ganglion cells invivo. Dev Neurobiol. 2007 June; 67(7):884-94.

Shoval G, Weizman A. The possible role of neurotrophins in the pathogenesis and therapy of schizophrenia. Eur Neuropsychopharmacol. 2005 May; 15(3):319-29.

Vajda F J. Neuroprotection and neurodegenerative disease. J Clin Neurosci. 2002 January; 9(1):4-8.

Villoslada P, Genain C (2004) Role of nerve growth factor and other trophic factors in brain inflammation. Prog Brain Res 146:403-414.

Villoslada P, Abel K, Heald N, Goertsches R, Hauser S, Genain C (2001) Frequency, heterogeneity and encephalitogenicity of T cells specific for myelin oligodendrocyte glycoprotein in naive outbred primates. Eur J Immunol 31:2942-2950.

Villoslada P, Hauser S, Bartke I, Unger J, Heald N, Rosenberg D, Cheung S, Mobley W, Fisher S, Genain C (2000) Human nerve growth factor protects common marmosets against autoimmune encephalomyelitis by switching the balance of T helper cell type 1 and 2 cytokines within the central nervous system. J Exp Med 191:1799-1806.

Williams B, Eriksdotter-Jonhagen M, Granholm A (2006) Nerve growth factor in treatment and pathogenesis of Alzheimer's disease. Prog Neurobiol 80:114-128. Epub 2006 November 2002.

Youdim M B, Buccafusco J J. Multi-functional drugs for various CNS targets in the treatment of neurodegenerative disorders. Trends Pharmacol Sci. 2005 January; 26(1):27-35.

Yoon S, Casaccia-Bonnefil P, Carter B, Chao M (1998) Competitive signaling between TrkA and p75 nerve growth factor receptors determines cell survival. J Neurosci 18:3273-3281.

Zaccaro M, Ivanisevic L, Perez P, Meakin S, Saragovi H (2001) p75 Co-receptors regulate ligand-dependent and ligand-independent Trk receptor activation, in part by altering Trk docking subdomains. J Biol Chem 276:31023-31029.

Zuckermann, R. N., Kerr, J. M., Kent, S. B. H., Moos, W. H. (1992). Efficient method for the preparation of peptoids [oligo(N-substituted glycines)] by submonomer solid phase synthesis. J. Am. Chem. Soc. 114, 10646-10647.

The invention claimed is:

1. A method of treatment of a disease, comprising administering to a subject in need thereof an effective amount of a compound of Formula III:

III or a pharmaceutically acceptable salt or prodrug thereof, wherein the disease is selected from: amyotrophic lateral sclerosis (ALS), Parkinson's disease multiple sclerosis, and glaucoma.

2. The method of claim 1, wherein the disease is multiple sclerosis.

3. The method of claim 1, wherein the disease is Parkinson's disease.

4. The method of claim 1, wherein the disease is glaucoma.

5. The method of claim 1, wherein the disease is ALS.

6. The method of claim 1, wherein the compound of Formula III, or a pharmaceutically acceptable salt or prodrug thereof, is administered to the subject by an oral, parenteral, subcutaneous, intravenous, intramuscular, intraperitoneal, transdermal, intranasal, transmucosal, rectal or buccal route.

7. The method of claim 1, wherein the compound of Formula III, or a pharmaceutically acceptable salt or prodrug thereof, is administered to the subject orally.

8. The method of claim 1, wherein the compound of Formula III, or a pharmaceutically acceptable salt or prodrug thereof, is administered to the subject by topical application.

9. The method of claim 1, wherein the compound of Formula III, or a pharmaceutically acceptable salt or prodrug thereof, is administered to the subject by injection.

10. The method of claim 1, wherein the compound of Formula III, or a pharmaceutically acceptable salt or prodrug thereof, is administered at an amount of from 10 mg to 500 mg per day.

11. The method of claim 1, wherein the subject is a human.

12. A method of treatment of Parkinson's disease, comprising administering to a subject in need thereof an effective amount of Formula IV or Formula V:

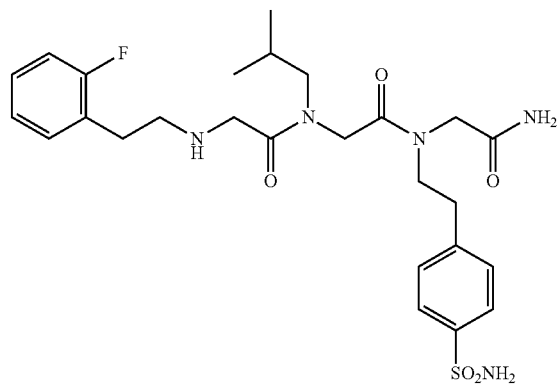

IV

-continued

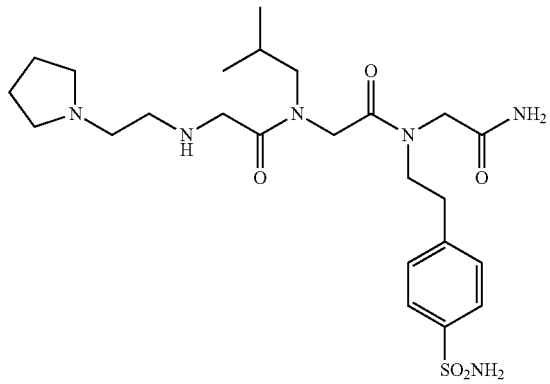

V or a pharmaceutically acceptable salt or prodrug thereof.

13. The method of claim 12, wherein the compound of Formula IV or Formula V, or a pharmaceutically acceptable salt or prodrug thereof, is administered to the subject by an oral, parenteral, subcutaneous, intravenous, intramuscular, intraperitoneal, transdermal, intranasal, transmucosal, rectal or buccal route.

14. The method of claim 12, wherein the compound of Formula IV or Formula V, or a pharmaceutically acceptable salt or prodrug thereof, is administered to the subject orally.

15. The method of claim 12, wherein the compound of Formula IV or Formula V, or a pharmaceutically acceptable salt or prodrug thereof, is administered to the subject by injection.

16. The method of claim 12, wherein the compound of Formula IV or Formula V, or a pharmaceutically acceptable salt or prodrug thereof, is administered at an amount of from 10 mg to 500 mg per day.

17. The method of claim 12, wherein the subject is a human.

* * * * *